(12) United States Patent
Sun et al.

(10) Patent No.: US 9,526,769 B2
(45) Date of Patent: *Dec. 27, 2016

(54) MACROCYLIC OXIMYL HEPATITIS C PROTEASE INHIBITORS

(75) Inventors: Ying Sun, Waltham, MA (US); Deqiang Niu, Lexington, MA (US); Guoyou Xu, Framingham, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 2348 days.

This patent is subject to a terminal disclaimer.

(21) Appl. No.: 11/759,080

(22) Filed: Jun. 6, 2007

(65) Prior Publication Data

US 2007/0281885 A1    Dec. 6, 2007

Related U.S. Application Data

(60) Provisional application No. 60/811,464, filed on Jun. 6, 2006, provisional application No. 60/999,770, filed on Aug. 11, 2006.

(51) Int. Cl.

| | | |
|---|---|---|
| *A61K 38/00* | (2006.01) | |
| *A61K 38/48* | (2006.01) | |
| *A61K 38/21* | (2006.01) | |
| *A61K 38/45* | (2006.01) | |
| *A61K 38/52* | (2006.01) | |
| *C07K 5/083* | (2006.01) | |
| *C07K 5/087* | (2006.01) | |
| *C07K 7/06* | (2006.01) | |

(52) U.S. Cl.
CPC ........... *A61K 38/4886* (2013.01); *A61K 38/21* (2013.01); *A61K 38/212* (2013.01); *A61K 38/215* (2013.01); *A61K 38/45* (2013.01); *A61K 38/52* (2013.01); *C07K 5/0804* (2013.01); *C07K 5/0812* (2013.01); *C07K 7/06* (2013.01)

(58) Field of Classification Search
None
See application file for complete search history.

(56) References Cited

U.S. PATENT DOCUMENTS

| 5,861,297 A | 1/1999 | Sardana et al. |
| 6,037,157 A | 3/2000 | Norbeck et al. |
| 6,608,027 B1 | 8/2003 | Tsantrizos et al. |
| 7,125,845 B2 | 10/2006 | Wu et al. |
| 7,173,004 B2 | 2/2007 | McPhee et al. |
| 7,176,208 B2 | 2/2007 | Nakajima et al. |
| 7,273,851 B2 | 9/2007 | Miao et al. |
| 2005/0119168 A1* | 6/2005 | Venkatraman et al. ........ 514/9 |
| 2005/0153877 A1 | 7/2005 | Miao et al. |
| 2005/0153900 A1* | 7/2005 | Velazquez et al. ........... 514/18 |
| 2005/0164921 A1* | 7/2005 | Njoroge et al. ............... 514/9 |
| 2007/0099825 A1 | 5/2007 | D'Andrea et al. |
| 2007/0281884 A1 | 12/2007 | Sun et al. |
| 2008/0125444 A1 | 5/2008 | Sun et al. |

FOREIGN PATENT DOCUMENTS

| WO | WO 99/07733 | 2/1999 |
| WO | WO 99/50230 | 10/1999 |
| WO | WO 00/09543 | 2/2000 |
| WO | WO 00/59929 | 12/2000 |
| WO | 2004072243 A2 | 8/2004 |
| WO | WO 2004072243 | 8/2004 |

(Continued)

OTHER PUBLICATIONS

Ettmayer P. et al. J. Med. Chem. (2004) 47(10), pp. 2393-2404.*
Testa. B., Biochem. Pharm. (2004) 68, pp. 2097-2106.*
Beaumont, K., et al, "Design of Ester Prodrugs to Enhance Oral Absorption of Poorly Permeable," Current Drug Metabolism, 2003, 4, 461-485.*
Herr, J.R., "A Whirlwind Tour of Current Mitsunobu Chemistry", Albany Molecular Research, Inc., Technical Report, 1999, Vol. 3, No. 19, pp. 1-36 (Particularly 11-12).

(Continued)

*Primary Examiner* — Thomas S Heard

(74) *Attorney, Agent, or Firm* — Edgar W. Harlan; Carolyn S. Elmore; Elmore Patent Law Group, P.C.

(57) ABSTRACT

The present invention discloses compounds of formula I, or pharmaceutically acceptable salts, esters, or prodrugs thereof:

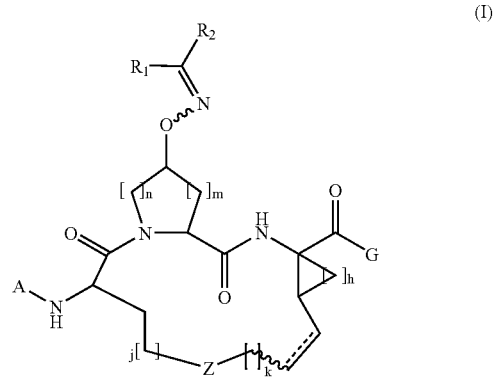

which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

29 Claims, No Drawings

(56) References Cited

FOREIGN PATENT DOCUMENTS

| WO | 2004093915 A1 | 11/2004 |
| WO | WO 2004093915 | 11/2004 |
| WO | 2005010029 A1 | 2/2005 |
| WO | WO 2005010029 | 2/2005 |

OTHER PUBLICATIONS

United States Patent and Trademark Office, Before the Board of Patent Appeals and Interferences, Decision on Appeal, Appeal 2009-015302, pp. 1-15, 2010.
R.C. Griffith, et al., "HCV Anti-viral Agents", Annual Reports in Medicinal Chemistry, vol. 39, p. 223-237. (2004 Elsevier Inc.).
Wangsell F. Design and Synthesis of Serine and Aspartic Protease Inhibitors, (Linkopings Studies in Science and Technology), Thesis No. 1264, 2006.
Llinas-Brunet, et. al., Bioorganic & Medicinal Chemistry Letters, 8, 1998, 1713-1718.
Prongay, A J. et. al., Discovery of the HCV NS3/4A protease inhibitor., J. Med. Chem. 2007 (50) 2310-2318.
Tsantrizos, et al., "Macrocyclic Inhibitors of the NS3 Protease as Potential Therapeutic Agents of Hepatitis C Virus Infection", Angewandte Chem. Int. Ed., 2003, 42, pp. 1356-1360.

\* cited by examiner

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
```

```
<223> OTHER INFORMATION: Synthetic

<400> SEQUENCE: 1 gctgcggcc tgtcgagct                                              18

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2 caaggtcgt ctccgcatac                                             19

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3 cgaagctcc aggactgcac gatgct                                      25
```

MACROCYLIC OXIMYL HEPATITIS C PROTEASE INHIBITORS

RELATED APPLICATION

This application claims the benefit of U.S. Provisional Application No. 60/811,464, filed on Jun. 6, 2006, and U.S. Provisional Application No. 60/999,770, which was converted from U.S. application Ser. No. 11/502,740 filed Aug. 11, 2006. The entire teachings of the above applications are incorporated herein by reference.

TECHNICAL FIELD

The present invention relates to novel hepatitis C virus (HCV) protease inhibitor compounds having antiviral activity against HCV and useful in the treatment of HCV infections. More particularly, the invention relates to HCV protease inhibitor compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-alpha (IFN-α), while a new approved second-generation treatment involves co-treatment with IFN-α and the general antiviral nucleoside mimics like ribavirin. Both of these treatments suffer from interferon-related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug preferably possesses significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3-NS4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, Nature Rev. Drug Discov., 1, 867-881 (2002). More relevant patent disclosures describing the synthesis of HCV protease inhibitors are: WO 00/59929 (2000); WO 99/07733 (1999); WO 00/09543 (2000); WO 99/50230 (1999); U.S. Pat. No. 5,861,297 (1999); US publications 20050153877, 20050261200 and 20050065073.

SUMMARY OF THE INVENTION

The present invention relates to novel HCV protease inhibitor compounds including pharmaceutically acceptable salts, esters, or prodrugs thereof which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds, salts, esters or prodrugs for administration to a subject suffering from HCV infection. The present invention further features pharmaceutical compositions comprising a compound of the present invention (or a pharmaceutically acceptable salt, ester or prodrug thereof) and another anti-HCV agent, such as alpha-interferon, beta-interferon, ribavirin, amantadine, another HCV protease inhibitor, or an HCV polymerase, helicase or internal ribosome entry site inhibitor. The invention also relates to methods of treating an HCV infection in a subject by administering a pharmaceutical composition of the present invention.

In one embodiment of the present invention, there are disclosed compounds of formula I:

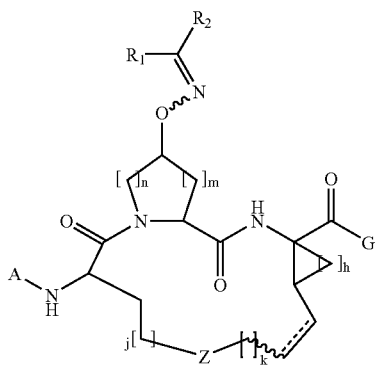

as well as the pharmaceutically acceptable salts, esters and prodrugs thereof, wherein:

$R_1$ and $R_2$ are independently selected from the group consisting of:
a) hydrogen;
b) aryl;
c) substituted aryl;
d) heteroaryl;
e) substituted heteroaryl;
f) heterocyclic or substituted heterocyclic;
g) —$C_1$-$C_8$ alkyl, —$C_2$-$C_8$ alkenyl, or —$C_2$-$C_8$ alkynyl each containing 0, 1, 2, or 3 heteroatoms selected from O, S or N;
h) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
i) —$C_3$-$C_{12}$ cycloalkyl, or substituted —$C_3$-$C_{12}$ cycloalkyl;
j) —$C_3$-$C_{12}$ cycloalkenyl, or substituted —$C_3$-$C_{12}$ cycloalkenyl;
k) —B—$R_3$, where B is (CO), (CO)O, (CO)$NR_4$, (SO), ($SO_2$), ($SO_2$)$NR_4$; and $R_3$ and $R_4$ are independently selected from the group consisting of:
  (i) Hydrogen;
  (ii) aryl;
  (iii) substituted aryl;
  (iv) heteroaryl;
  (v) substituted heteroaryl;
  (vi) heterocyclic;
  (vii) substituted heterocyclic;
  (viii) —$C_1$-$C_8$ alkyl; —$C_2$-$C_8$ alkenyl, —$C_2$-$C_8$ alkynyl each containing 0, 1, 2, or 3 heteroatoms selected from O, S or N;
  (xi) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
  (x) —$C_3$-$C_{12}$ cycloalkyl; substituted —$C_3$-$C_{12}$ cycloalkyl;
  (xvi) —$C_3$-$C_{12}$ cycloalkenyl, and substituted —$C_3$-$C_{12}$ cycloalkenyl;
alternatively, $R_1$ and $R_2$ taken together with the carbon atom to which they are attached form cyclic moiety consisting of: substituted or unsubstituted cycloalkyl, cycloalkenyl, or heterocyclic; substituted or unsubstituted cycloalkyl, cycloalkenyl, or heterocyclic each fused with one or more $R_3$; where $R_3$ is as previously defined;

G is -E-$R_3$ where E is absent, or E is O, CO, (CO)O, (CO)NH, NH, NH(CO), NH(CO)NH, NH($SO_2$)NH or NH$SO_2$; where $R_3$ is as previously defined;

Z is selected from the group consisting of $CH_2$, O, S, SO, or $SO_2$;

A is selected from the group consisting of $R_5$, (CO)$R_5$, (CO)O$R_5$, (CO)NH$R_5$, $SO_2R_5$, ($SO_2$)O$R_5$ and $SO_2$NH$R_5$;

$R_5$ is selected from the group consisting of:
1) aryl;
2) substituted aryl;
3) heteroaryl;
4) substituted heteroaryl;
5) heterocyclic;
6) substituted heterocyclic;
7) —$C_1$-$C_8$ alkyl; —$C_2$-$C_8$ alkenyl; —$C_2$-$C_8$ alkynyl each containing 0, 1, 2, or 3 heteroatoms selected from O, S or N;
8) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
9) —$C_3$-$C_{12}$ cycloalkyl;
10) substituted —$C_3$-$C_{12}$ cycloalkyl;
11) —$C_3$-$C_{12}$ cycloalkenyl; and
12) substituted —$C_3$-$C_{12}$ cycloalkenyl;

j=0, 1, 2, or 3;
k=0, 1, 2, or 3; and
m=0, 1, 2 or 3;
n=1, 2 or 3; and
h=0, 1, 2, or 3.

In another embodiment, the present invention features pharmaceutical compositions comprising a compound of the invention, or a pharmaceutically acceptable salt, ester or prodrug thereof. In still another embodiment of the present invention there are disclosed pharmaceutical compositions comprising a therapeutically effective amount of a compound of the invention, or a pharmaceutically acceptable salt, ester or prodrug thereof, in combination with a pharmaceutically acceptable carrier or excipient. In yet another embodiment of the invention are methods of treating a hepatitis C infection in a subject in need of such treatment with said pharmaceutical compositions.

DETAILED DESCRIPTION OF THE INVENTION

In a first embodiment, the present invention is a compound of formula I as illustrated above, or a pharmaceutically acceptable salt, ester or prodrug thereof.

In another embodiment, the present invention relates to a compound of formula II, or a pharmaceutically acceptable salt, ester or prodrug thereof:

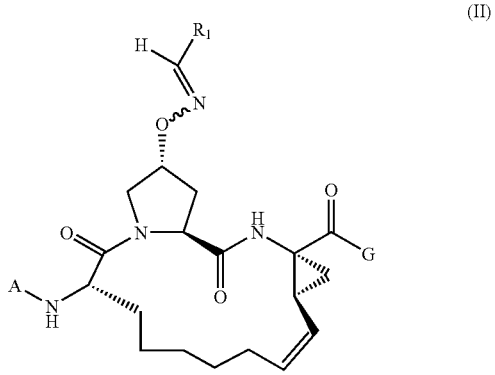

where A, G and $R_1$ are as previously defined. In a preferred example, $R_1$ is not hydrogen.

In another example, $R_1$ is selected from the group consisting of aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of $R_5$, —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$, —NH—C(O)—$R_3$, —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_1$ is selected from the group consisting of aryl, substituted aryl, heteroaryl, substituted heteroaryl, heterocyclic, and substituted heterocyclic. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still yet another example, $R_1$ is selected from the group consisting of aryl, substituted aryl, heteroaryl, substituted heteroaryl, heterocyclic, and substituted heterocyclic. A is —C(O)—O—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is selected from —$C_3$-$C_{12}$ cycloalkyl or substituted —$C_3$-$C_{12}$ cycloalkyl.

In another example, $R_1$ is selected from the group consisting of aryl, substituted aryl, heteroaryl, substituted heteroaryl, heterocyclic, and substituted heterocyclic. A is —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is selected from —$C_3$-$C_{12}$ cycloalkyl or substituted —$C_3$-$C_{12}$ cycloalkyl.

In yet another example, $R_1$ is selected from the group consisting of aryl, substituted aryl, heteroaryl, substituted heteroaryl, heterocyclic, and substituted heterocyclic. A is —C(O)—$R_5$, where $R_5$ is substituted —$C_1$-$C_8$ alkyl (e.g., substituted methyl or ethyl) and is substituted with (1) aryl or heteroaryl, (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl, and optionally (3) one or more other substituents. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_1$ is selected from the group consisting of aryl, substituted aryl, heteroaryl, substituted heteroaryl, heterocyclic, and substituted heterocyclic. A is —C(O)—$R_5$, where $R_5$ is substituted methyl and is substituted at least with (1) aryl or heteroaryl and (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl. G is —$NHSO_2$—$R_3$, where $R_3$ is —$C_3$-$C_{12}$ cycloalkyl or substituted —$C_3$-$C_{12}$ cycloalkyl.

In another example, $R_1$ is selected from the group consisting of aryl, substituted aryl, heteroaryl, substituted heteroaryl, heterocyclic, and substituted heterocyclic. A is —$R_5$, where $R_5$ is —$C_1$-$C_8$ alkyl or substituted —$C_1$-$C_8$ alkyl. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In one embodiment, the present invention relates to a compound of formula III, or a pharmaceutically acceptable salt, ester or prodrug thereof:

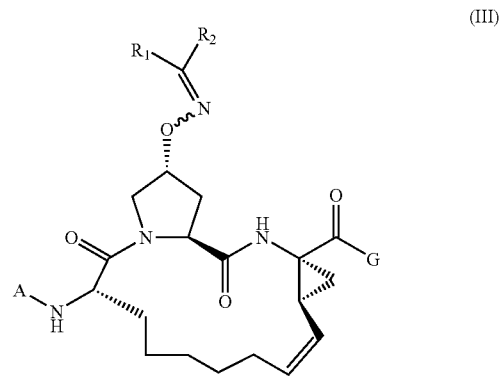

(III)

where A, G, $R_1$ and $R_2$ are as previously defined in the first embodiment. In a preferred example, $R_1$ and $R_2$ are not both hydrogen.

In another example, $R_1$ and $R_2$ are independently selected from the group consisting of aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; or $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from aryl, substituted aryl, heteroaryl, substituted heteroaryl, heterocyclic or substituted heterocyclic. A can be selected from the group consisting of —$R_5$, —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$, —NH—C(O)—$R_3$, —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In a preferred example, $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from aryl, substituted aryl, heteroaryl, substituted heteroaryl, heterocyclic or substituted heterocyclic. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In another preferred example, $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from aryl, substituted aryl, heteroaryl, substituted heteroaryl, heterocyclic or substituted heterocyclic. A is —C(O)—O—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$, where $R_3$ is selected from —$C_3$-$C_{12}$ cycloalkyl or substituted —$C_3$-$C_{12}$ cycloalkyl.

In still another preferred example, $R_1$ and $R_2$ taken together with the carbon atom to which they are attached form

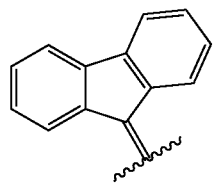 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl. A is —C(O)—O—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$, where $R_3$ is selected from —$C_3$-$C_{12}$ cycloalkyl or substituted —$C_3$-$C_{12}$ cycloalkyl.

In yet another preferred example, $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from aryl, substituted aryl, heteroaryl, substituted heteroaryl, heterocyclic or substituted heterocyclic. A is —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$, where $R_3$ is selected from —$C_3$-$C_{12}$ cycloalkyl or substituted —$C_3$-$C_{12}$ cycloalkyl. Preferably, $R_1$ and $R_2$ taken together with the carbon atom to which they are attached form

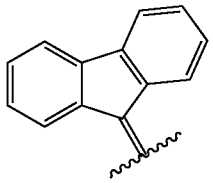 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl.

In another preferred example, $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from aryl, substituted aryl, heteroaryl, substituted heteroaryl, heterocyclic or substituted heterocyclic. A is —C(O)—$R_5$, where $R_5$ is substituted —$C_1$-$C_8$ alkyl (e.g., substituted methyl or ethyl) and is substituted with (1) aryl or heteroaryl, (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl, and optionally (3) one or more other substituents. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In yet another preferred example, $R_1$ and $R_2$ taken together with the carbon atom to which they are attached form

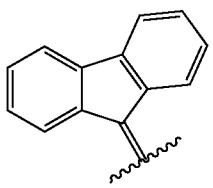 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl. A is —C(O)—$R_5$, where $R_5$ is substituted methyl and is substituted at least with (1) aryl or heteroaryl and (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl. G is —NHSO$_2$—$R_3$, where $R_3$ is —$C_3$-$C_{12}$ cycloalkyl or substituted —$C_3$-$C_{12}$ cycloalkyl.

In another preferred example, $R_1$ and $R_2$ taken together with the carbon atom to which they are attached form

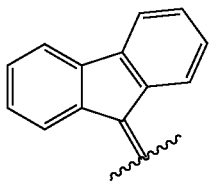 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl. A is —$R_5$, where $R_5$ is —$C_1$-$C_8$ alkyl or substituted —$C_1$-$C_8$ alkyl. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In further embodiment, the present invention relates to a compound of formula IV, or a pharmaceutically acceptable salt, ester or prodrug thereof:

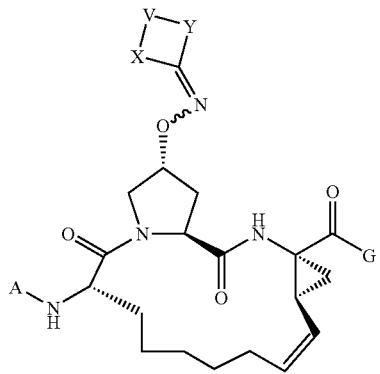

(IV)

wherein V is absent, or V is CO, O, S, SO, $SO_2$, NH or $NCH_3$, or $(CH_2)_q$; where q is 1, 2, 3 or 4; and where X and Y are independently selected from the group consisting of: (i) aryl; substituted aryl; (ii) heteroaryl; substituted heteroaryl; (iii) heterocyclic; substituted heterocyclic; where A and G are as previously defined in the first embodiment.

In one example,

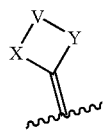

is selected from

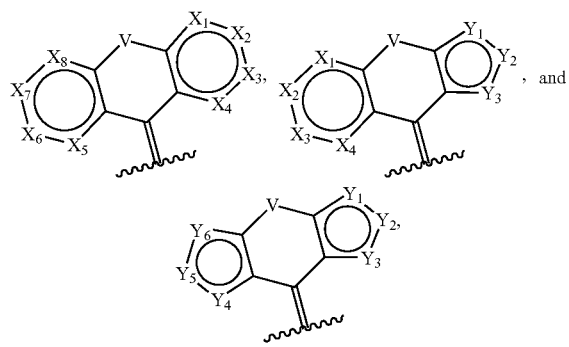

, and wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A can be selected from the group consisting of $R_5$, —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$, —NH—C(O)—$R_3$, —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example,

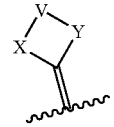

is selected from

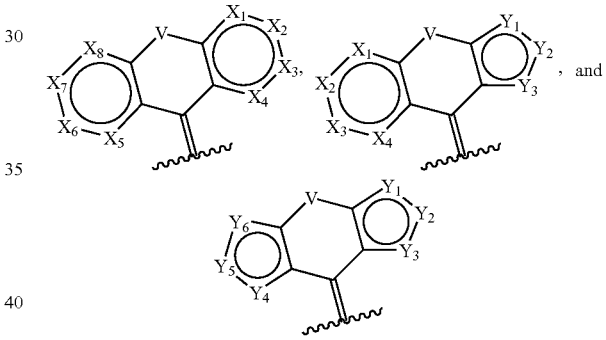

, and and wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still yet another example,

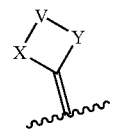

is selected from

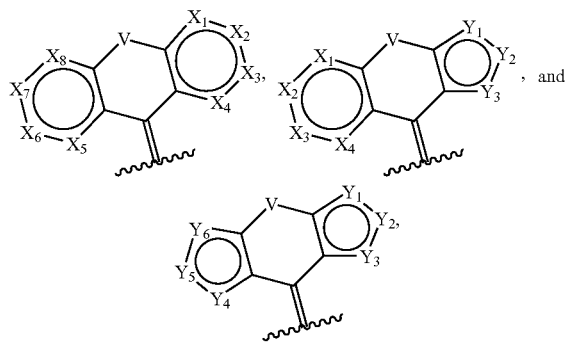

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —NHSO$_2$—$R_3$, where $R_3$ is selected from —$C_3$-$C_{12}$ cycloalkyl or substituted —$C_3$-$C_{12}$ cycloalkyl.

In another example,

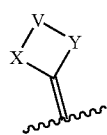

is selected from

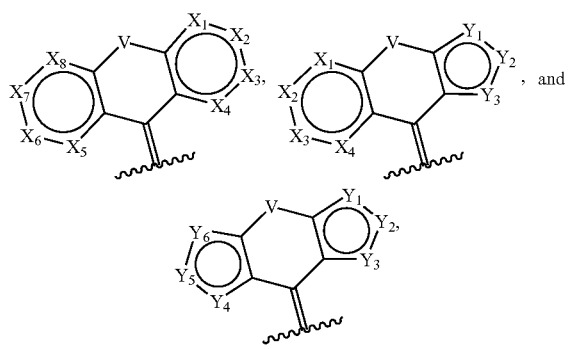

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A is —C(O)—$R_5$, where $R_5$ is substituted —$C_1$-$C_8$ alkyl (e.g., substituted methyl or ethyl) and is substituted with (1) aryl or heteroaryl, (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl, and optionally (3) one or more other substituents. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In a preferred example, $R_1$ and $R_2$ taken together with the carbon atom to which they are attached form

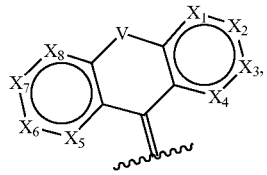

wherein $X_1$-$X_8$ are independently selected from CH and N and $X_1$-$X_8$ can be further substituted when it is a CH; V is absent, CO, O, S, NH, or $(CH_2)_q$, where q is 1, 2 or 3. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —NHSO$_2$—$R_3$, where $R_3$ is selected from —$C_3$-$C_{12}$ cycloalkyl or substituted —$C_3$-$C_{12}$ cycloalkyl.

In a preferred example, $R_1$ and $R_2$ taken together with the carbon atom to which they are attached form

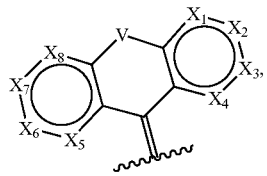

wherein $X_1$-$X_8$ are independently selected from CH and N and $X_1$-$X_8$ can be further substituted when it is a CH; V is absent, CO, O, S, NH, or $(CH_2)_q$, where q is 1, 2 or 3. A is —C(O)—$R_5$, where $R_5$ is substituted —$C_1$-$C_8$ alkyl (e.g., substituted methyl or ethyl) and is substituted with (1) aryl or heteroaryl, (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl, and optionally (3) one or more other substituents. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In a most preferred example, $R_1$ and $R_2$ taken together with the carbon atom to which they are attached form

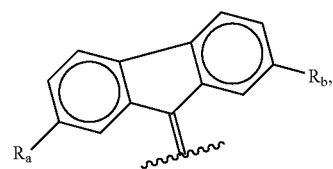

wherein Ra and Rb is independently selected from hydrogen or halogen. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is selected from —$C_3$-$C_{12}$ cycloalkyl or substituted —$C_3$-$C_{12}$ cycloalkyl.

In a most preferred example, $R_1$ and $R_2$ taken together with the carbon atom to which they are attached form

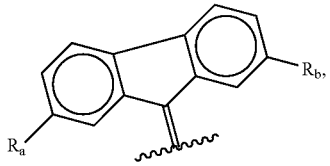

wherein Ra and Rb is independently selected from hydrogen or halogen. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is selected from —$C_3$-$C_{12}$ cycloalkyl or substituted —$C_3$-$C_{12}$ cycloalkyl.

In another preferred example, $R_1$ and $R_2$ taken together with the carbon atom to which they are attached form

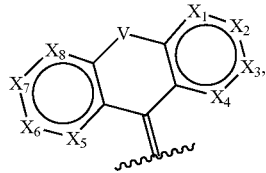

wherein $X_1$-$X_8$ are independently selected from CH and N and $X_1$-$X_8$ can be further substituted when it is a CH; V is absent, CO, O, S, NH, or $(CH_2)_q$, where q is 1, 2 or 3. A is —$R_5$, where $R_5$ is —$C_1$-$C_8$ alkyl or substituted —$C_1$-$C_8$ alkyl. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In one embodiment, the present invention relates to a compound of formula V, or a pharmaceutically acceptable salt, ester or prodrug thereof:

(V)

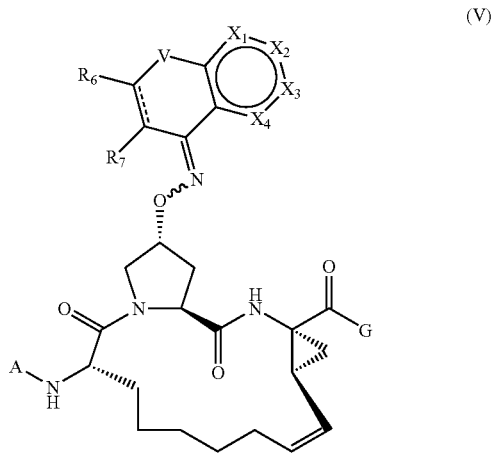

Where $X_1$-$X_4$ are independently selected from CO, CH, NH, O and N; and wherein $X_1$-$X_4$ can be further substituted when any one of $X_1$-$X_4$ is CH or NH; where $R_6$ and $R_7$ are independently $R_3$; where $R_3$ is independently selected from the group consisting of:

(i) hydrogen;
(ii) aryl;
(iii) substituted aryl;
(iv) heteroaryl;
(v) substituted heteroaryl;
(vi) heterocyclic;
(vii) substituted heterocyclic;
(viii) —$C_1$-$C_8$ alkyl, —$C_2$-$C_8$ alkenyl, or —$C_2$-$C_8$ alkynyl each containing 0, 1, 2, or 3 heteroatoms selected from O, S or N;
(ix) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
(x) —$C_3$-$C_{12}$ cycloalkyl, or —$C_3$-$C_{12}$ cycloalkenyl;
(xi) substituted —$C_3$-$C_{12}$ cycloalkyl, or substituted —$C_3$-$C_{12}$ cycloalkenyl; and where A, G and V are as previously defined in the embodiment immediately above. Alternatively, $R_6$ and $R_7$ can be independently selected from halogen, oxo, thioxo, nitro, cyano, —$OR_3$, —$SR_3$, —$NR_3R_4$, —$SOR_3$, —$SO_2R_3$, —$NHSO_2R_3$, —$SO_2NHR_3$, —$COR_3$, —$CO_2R_3$, $(CO)NHR_3$, —$OCOR_3$, $OCONHR_3$, $NHCO_2R_3$, —$NH(CO)R_3$, —$NH(CO)NHR_3$, and —$NH(SO_2)NHR_3$.

In one example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of $R_5$, —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$', —NH—C(O)—$R_3$', —NH—$SO_2$—NH—$R_3$' or —$NHSO_2$—$R_3$', where $R_3$' is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$', where $R_3$' is selected from aryl, substituted aryl, heteroaryl, substituted heteroaryl, heterocyclic, substituted heterocyclic, —$C_3$-$C_{12}$ cycloalkyl, —$C_3$-

$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$', where $R_3$' is selected from —$C_3$-$C_{12}$ cycloalkyl or substituted —$C_3$-$C_{12}$ cycloalkyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$, where $R_3$ is selected from —$C_3$-$C_{12}$ cycloalkyl or substituted —$C_3$-$C_{12}$ cycloalkyl.

In yet another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted —$C_1$-$C_8$ alkyl (e.g., substituted methyl or ethyl) and is substituted with (1) aryl or heteroaryl, (2) —NHCO$_2$—$C_1$-$C_{12}$-alkyl, —NHCO$_2$—$C_2$-$C_{12}$-alkenyl, —NHCO$_2$—$C_2$-$C_{12}$-alkynyl, —NHC(O)-aryl or —NHC(O)-heteroaryl, and optionally (3) one or more other substituents. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted methyl and is substituted at least with (1) aryl or heteroaryl and (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl. G is —NHSO$_2$—$R_3$, where $R_3$ is —$C_3$-$C_{12}$ cycloalkyl or substituted —$C_3$-$C_{12}$ cycloalkyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —$R_5$, where $R_5$ is —$C_1$-$C_8$ alkyl or substituted —$C_1$-$C_8$ alkyl. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In one embodiment, the present invention relates to a compound of formula VI, or a pharmaceutically acceptable salt, ester or prodrug thereof:

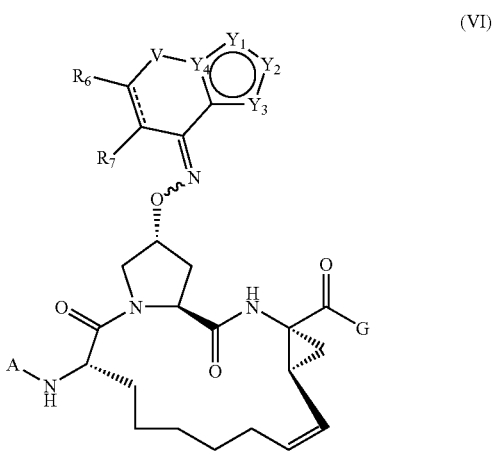

(VI)

Where $Y_1$-$Y_3$ are independently selected from CO, CH, NH, N, S and O; and where $Y_1$-$Y_3$ can be further substituted when any one of $Y_1$-$Y_3$ is CH or NH; $Y_4$ is selected from C, CH and N; and where A, G, $R_6$, $R_7$ and V are as previously defined.

In one example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of —$R_5$, —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$', —NH—C(O)—$R_3$', —NH—SO$_2$—NH—$R_3$' or —NHSO$_2$—$R_3$', where $R_3$' is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. G is —NHSO$_2$—R$_3$', where R$_3$' is selected from aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl.

In still another example, R$_6$ and R$_7$ are independently selected from the group consisting of hydrogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl. A is —C(O)—O—R$_5$, where R$_5$ is —C$_1$-C$_8$ alkyl, substituted —C$_1$-C$_8$ alkyl, —C$_3$-C$_{12}$ cycloalkyl or substituted —C$_3$-C$_{12}$ cycloalkyl. G is —NHSO$_2$—R$_3$', where R$_3$' is selected from —C$_3$-C$_{12}$ cycloalkyl or substituted —C$_3$-C$_{12}$ cycloalkyl.

In another example, R$_6$ and R$_7$ are independently selected from the group consisting of hydrogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl. A is —C(O)—NH—R$_5$, where R$_5$ is —C$_1$-C$_8$ alkyl, substituted —C$_1$-C$_8$ alkyl, —C$_3$-C$_{12}$ cycloalkyl or substituted —C$_3$-C$_{12}$ cycloalkyl. G is —NHSO$_2$—R$_3$, where R$_3$ is selected from —C$_3$-C$_{12}$ cycloalkyl or substituted —C$_3$-C$_{12}$ cycloalkyl.

In yet another example, R$_6$ and R$_7$ are independently selected from the group consisting of hydrogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl. A is —C(O)—R$_5$, where R$_5$ is substituted —C$_1$-C$_8$ alkyl (e.g., substituted methyl or ethyl) and is substituted with (1) aryl or heteroaryl, (2) —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHC(O)-aryl or —NHC(O)-heteroaryl, and optionally (3) one or more other substituents. G is —NHSO$_2$—R$_3$, where R$_3$ is selected from aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkyl.

In still another example, R$_6$ and R$_7$ are independently selected from the group consisting of hydrogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl. A is —C(O)—R$_5$, where R$_5$ is substituted methyl and is substituted at least with (1) aryl or heteroaryl and (2) —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHC(O)-aryl or —NHC(O)-heteroaryl. G is —NHSO$_2$—R$_3$, where R$_3$ is —C$_3$-C$_{12}$ cycloalkyl or substituted —C$_3$-C$_{12}$ cycloalkyl.

In another example, R$_6$ and R$_7$ are independently selected from the group consisting of hydrogen, aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl. A is —R$_5$, where R$_5$ is —C$_1$-C$_8$ alkyl or substituted —C$_1$-C$_8$ alkyl. G is —NHSO$_2$—R$_3$, where R$_3$ is selected from aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl.

In another embodiment, the present invention relates to a compound of formula VII, or a pharmaceutically acceptable salt, ester or prodrug thereof:

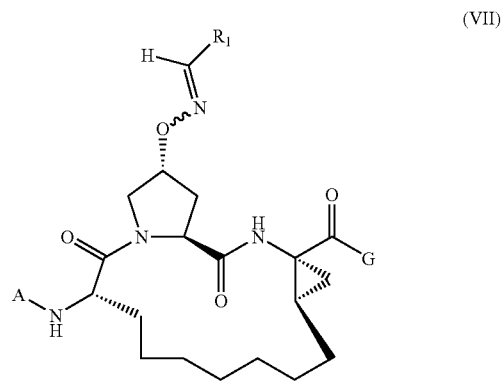

(VII)

where A, G and R$_1$ are as previously defined. In a preferred example, R$_1$ is not hydrogen.

In another example, R$_1$ is selected from the group consisting of aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl. A is selected from the group consisting of —R$_5$, —C(O)—R$_5$, —C(O)—O—R$_5$ and —C(O)—NH—R$_5$, where R$_5$ is selected from aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. G can be —O—R$_3$, —NH—C(O)—R$_3$, —NH—SO$_2$—NH—R$_3$ or —NHSO$_2$—R$_3$, where R$_3$ is selected from hydrogen, aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl.

In still another example, R$_1$ is selected from the group consisting of aryl, substituted aryl, heteroaryl, substituted heteroaryl, heterocyclic, and substituted heterocyclic. A is —C(O)—O—R$_5$ or —C(O)—NH—R$_5$, where R$_5$ is —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. G is —NHSO$_2$—R$_3$, where R$_3$ is selected from aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl.

In still yet another example, R₁ is selected from the group consisting of aryl, substituted aryl, heteroaryl, substituted heteroaryl, heterocyclic, and substituted heterocyclic. A is —C(O)—O—R₅, where R₅ is —C₁-C₈ alkyl, substituted —C₁-C₈ alkyl, —C₃-C₁₂ cycloalkyl or substituted —C₃-C₁₂ cycloalkyl. G is —NHSO₂—R₃, where R₃ is selected from —C₃-C₁₂ cycloalkyl or substituted —C₃-C₁₂ cycloalkyl.

In another example, R₁ is selected from the group consisting of aryl, substituted aryl, heteroaryl, substituted heteroaryl, heterocyclic, and substituted heterocyclic. A is —C(O)—NH—R₅, where R₅ is —C₁-C₈ alkyl, substituted —C₁-C₈ alkyl, —C₃-C₁₂ cycloalkyl or substituted —C₃-C₁₂ cycloalkyl. G is —NHSO₂—R₃, where R₃ is selected from —C₃-C₁₂ cycloalkyl or substituted —C₃-C₁₂ cycloalkyl.

In still yet another example, R₁ is selected from the group consisting of aryl, substituted aryl, heteroaryl, substituted heteroaryl, heterocyclic, and substituted heterocyclic. A is —C(O)—R₅, where R₅ is substituted —C₁-C₈ alkyl (e.g., substituted methyl or ethyl) and is substituted with (1) aryl or heteroaryl, (2)) —NHCO₂—C₁-C₁₂-alkyl, —NHCO₂—C₂-C₁₂-alkenyl, —NHCO₂—C₂-C₁₂-alkenyl, —NHC(O)-aryl or —NHC(O)-heteroaryl, and optionally (3) one or more other substituents. G is —NHSO₂—R₃, where R₃ is selected from aryl, substituted aryl, heteroaryl, substituted heteroaryl, heterocyclic, substituted heterocyclic, —C₃-C₁₂ cycloalkyl, —C₃-C₁₂ cycloalkenyl, substituted —C₃-C₁₂ cycloalkyl, or substituted —C₃-C₁₂ cycloalkenyl.

In another example, R₁ is selected from the group consisting of aryl, substituted aryl, heteroaryl, substituted heteroaryl, heterocyclic, and substituted heterocyclic. A is —R₅, where R₅ is —C₁-C₈ alkyl or substituted —C₁-C₈ alkyl. G is —NHSO₂—R₃, where R₃ is selected from aryl, substituted aryl, heteroaryl, substituted heteroaryl, heterocyclic, substituted heterocyclic, —C₃-C₁₂ cycloalkyl, —C₃-C₁₂ cycloalkenyl, substituted —C₃-C₁₂ cycloalkyl, or substituted —C₃-C₁₂ cycloalkenyl.

In another embodiment, the present invention relates to a compound of formula VIII, or a pharmaceutically acceptable salt, ester or prodrug thereof:

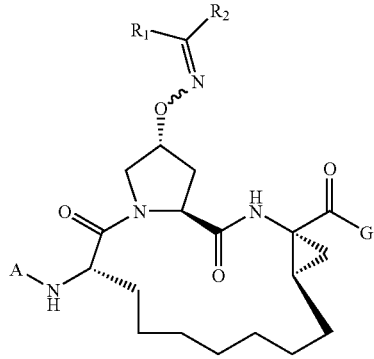

(VIII)

where A, G, R₁ and R₂ are as previously defined in the first embodiment. In a preferred example, R₁ and R₂ are not both hydrogen.

In another example, R₁ and R₂ are independently selected from the group consisting of aryl, substituted aryl, heteroaryl, substituted heteroaryl, heterocyclic, substituted heterocyclic, —C₃-C₁₂ cycloalkyl, —C₃-C₁₂ cycloalkenyl, substituted —C₃-C₁₂ cycloalkyl, and substituted —C₃-C₁₂ cycloalkenyl; or R₁ and R₂ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more R₃, where each R₃ is independently selected from aryl, substituted aryl, heteroaryl, substituted heteroaryl, heterocyclic or substituted heterocyclic. A can be selected from the group consisting of —R₅, —C(O)—R₅, —C(O)—O—R₅ and —C(O)—NH—R₅, where R₅ is selected from aryl, substituted aryl, heteroaryl, substituted heteroaryl, heterocyclic, substituted heterocyclic, —C₁-C₈ alkyl, —C₂-C₈ alkenyl, —C₂-C₈ alkynyl, substituted —C₁-C₈ alkyl, substituted —C₂-C₈ alkenyl, substituted —C₂-C₈ alkynyl, —C₃-C₁₂ cycloalkyl, —C₃-C₁₂ cycloalkenyl, substituted —C₃-C₁₂ cycloalkyl, or substituted —C₃-C₁₂ cycloalkenyl. G can be —O—R₃, —NH—C(O)—R₃, —NH—SO₂—NH—R₃ or —NHSO₂—R₃, where R₃ is selected from hydrogen, aryl, substituted aryl, heteroaryl, substituted heteroaryl, heterocyclic, substituted heterocyclic, —C₃-C₁₂ cycloalkyl, —C₃-C₁₂ cycloalkenyl, substituted —C₃-C₁₂ cycloalkyl, or substituted —C₃-C₁₂ cycloalkenyl.

In a preferred example, R₁ and R₂ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more R₃, where each R₃ is independently selected from aryl, substituted aryl, heteroaryl, substituted heteroaryl, heterocyclic or substituted heterocyclic. A is —C(O)—O—R₅ or —C(O)—NH—R₅, where R₅ is —C₁-C₈ alkyl, —C₂-C₈ alkenyl, —C₂-C₈ alkynyl, substituted —C₁-C₈ alkyl, substituted —C₂-C₈ alkenyl, substituted —C₂-C₈ alkynyl, —C₃-C₁₂ cycloalkyl, —C₃-C₁₂ cycloalkenyl, substituted —C₃-C₁₂ cycloalkyl, or substituted —C₃-C₁₂ cycloalkenyl. G is —NHSO₂—R₃, where R₃ is selected from aryl, substituted aryl, heteroaryl, substituted heteroaryl, heterocyclic, substituted heterocyclic, —C₃-C₁₂ cycloalkyl, —C₃-C₁₂ cycloalkenyl, substituted —C₃-C₁₂ cycloalkyl, or substituted —C₃-C₁₂ cycloalkenyl.

In another preferred example, R₁ and R₂ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more R₃, where each R₃ is independently selected from aryl, substituted aryl, heteroaryl, substituted heteroaryl, heterocyclic or substituted heterocyclic. A is —C(O)—O—R₅, where R₅ is —C₁-C₈ alkyl, substituted —C₁-C₈ alkyl, —C₃-C₁₂ cycloalkyl or substituted —C₃-C₁₂ cycloalkyl. G is —NHSO₂—R₃, where R₃ is selected from —C₃-C₁₂ cycloalkyl or substituted —C₃-C₁₂ cycloalkyl.

In still another preferred example, R₁ and R₂ taken together with the carbon atom to which they are attached form

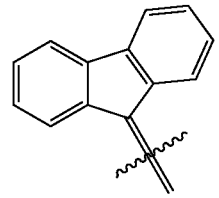 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl. A is —C(O)—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is selected from —$C_3$-$C_{12}$ cycloalkyl or substituted —$C_3$-$C_{12}$ cycloalkyl.

In yet another preferred example, $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from aryl, substituted aryl, heteroaryl, substituted heteroaryl, heterocyclic or substituted heterocyclic. A is —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is selected from —$C_3$-$C_{12}$ cycloalkyl or substituted —$C_3$-$C_{12}$ cycloalkyl. Preferably, $R_1$ and $R_2$ taken together with the carbon atom to which they are attached form

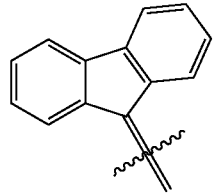 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl.

In another preferred example, $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from aryl, substituted aryl, heteroaryl, substituted heteroaryl, heterocyclic or substituted heterocyclic. A is —C(O)—$R_5$, where $R_5$ is substituted —$C_1$-$C_8$ alkyl (e.g., substituted methyl or ethyl) and is substituted with (1) aryl or heteroaryl, (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl, and optionally (3) one or more other substituents. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In yet another preferred example, $R_1$ and $R_2$ taken together with the carbon atom to which they are attached form

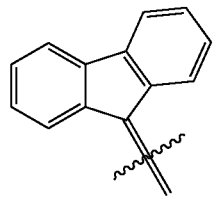 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl. A is —C(O)—$R_5$, where $R_5$ is substituted methyl and is substituted at least with (1) aryl or heteroaryl and (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl. G is —$NHSO_2$—$R_3$, where $R_3$ is —$C_3$-$C_{12}$ cycloalkyl or substituted —$C_3$-$C_{12}$ cycloalkyl.

In another preferred example, $R_1$ and $R_2$ taken together with the carbon atom to which they are attached form

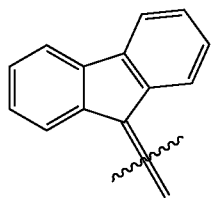 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl. A is —$R_5$, where $R_5$ is —$C_1$-$C_8$ alkyl or substituted —$C_1$-$C_8$ alkyl. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In one embodiment, the present invention relates to a compound of formula IX, or a pharmaceutically acceptable salt, ester or prodrug thereof:

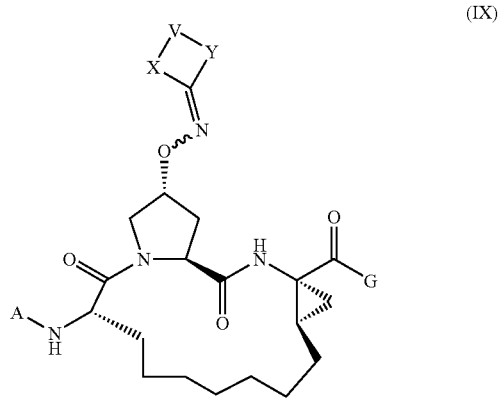

wherein V is absent, or V is CO, O, S, SO, $SO_2$, NH or $NCH_3$, or $(CH_2)_q$; where q is 1, 2, 3 or 4; and where X and Y are independently selected from the group consisting of: (i) aryl; substituted aryl; (ii) heteroaryl; substituted heteroaryl; (iii) heterocyclic; substituted heterocyclic; where A and G are as previously defined in the first embodiment.

In one example,

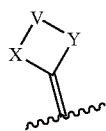

is selected from

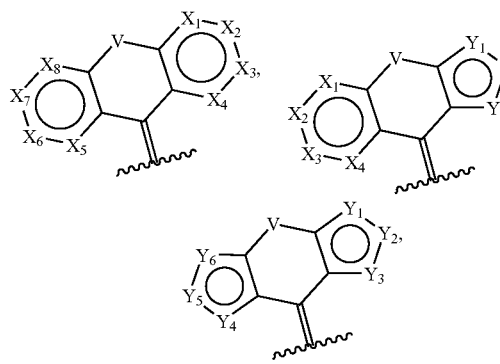

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A can be selected from the group consisting of —$R_5$, —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$, —NH—C(O)—$R_3$, —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example,

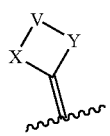

is selected from

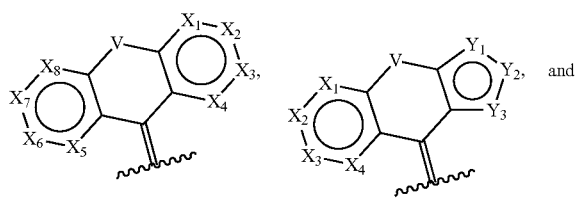

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still yet another example,

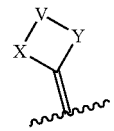

is selected from

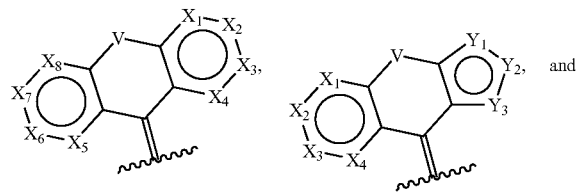

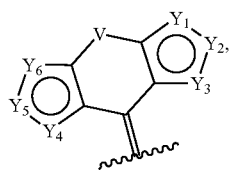

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S. NH, or $(CH_2)_q$, where q is 1, 2 or 3. A is —C(O)—O—$R_5$ or —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is selected from —$C_3$-$C_{12}$ cycloalkyl or substituted —$C_3$-$C_{12}$ cycloalkyl.

In another example,

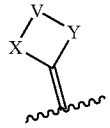

is selected from

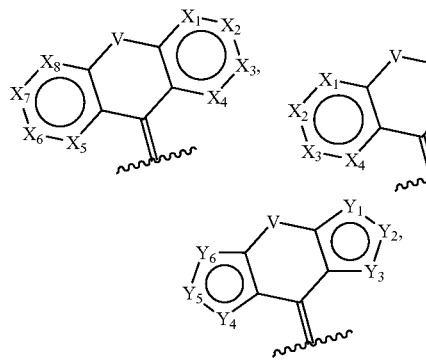

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A is —C(O)—$R_5$, where $R_5$ is substituted —$C_1$-$C_8$ alkyl (e.g., substituted methyl or ethyl) and is substituted with (1) aryl or heteroaryl, (2) —NHCO$_2$—$C_1$-$C_{12}$-alkyl, —NHCO$_2$—$C_2$-$C_{12}$-alkenyl, —NHC(O)-aryl or —NHC(O)-heteroaryl, and optionally (3) one or more other substituents. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In a preferred example, $R_1$ and $R_2$ taken together with the carbon atom to which they are attached form

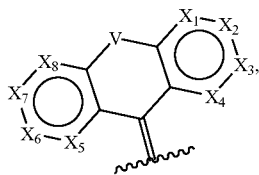

wherein $X_1$-$X_8$ are independently selected from CH and N and $X_1$-$X_8$ can be further substituted when it is a CH; V is absent, CO, O, S, NH, or $(CH_2)_q$, where q is 1, 2 or 3. A is —C(O)—O—$R_5$ or —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$, where $R_3$ is selected from —$C_3$-$C_{12}$ cycloalkyl or substituted —$C_3$-$C_{12}$ cycloalkyl.

In a preferred example, $R_1$ and $R_2$ taken together with the carbon atom to which they are attached form

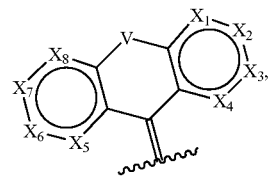

wherein $X_1$-$X_8$ are independently selected from CH and N and $X_1$-$X_8$ can be further substituted when it is a CH; V is absent, CO, O, S, NH, or $(CH_2)_q$, where q is 1, 2 or 3. A is —C(O)—$R_5$, where $R_5$ is substituted —$C_1$-$C_8$ alkyl (e.g., substituted methyl or ethyl) and is substituted with (1) aryl or heteroaryl, (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl, and optionally (3) one or more other substituents. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In a most preferred example, $R_1$ and $R_2$ taken together with the carbon atom to which they are attached form

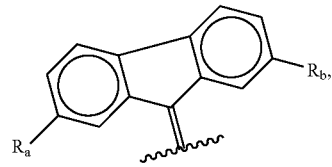

wherein Ra and Rb is independently selected from hydrogen or halogen. A is —C(O)—O—$R_5$ or —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$, where $R_3$ is selected from —$C_3$-$C_{12}$ cycloalkyl or substituted —$C_3$-$C_{12}$ cycloalkyl.

In another most preferred example, $R_1$ and $R_2$ taken together with the carbon atom to which they are attached form

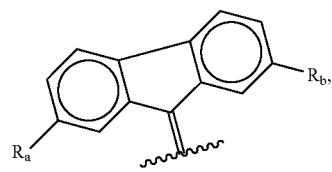

wherein Ra and Rb is independently selected from hydrogen or halogen. A is —C(O)—$R_5$, where $R_5$ is substituted —$C_1$-$C_8$ alkyl (e.g., substituted methyl or ethyl) and is substituted with (1) aryl or heteroaryl, (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl, and optionally (3) one or more other substituents. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In another preferred example, $R_1$ and $R_2$ taken together with the carbon atom to which they are attached form

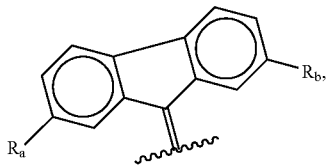

wherein Ra and Rb is independently selected from hydrogen or halogen. A is —$R_5$, where $R_5$ is —$C_1$-$C_8$ alkyl or substituted —$C_1$-$C_8$ alkyl. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In one embodiment, the present invention relates to a compound of formula X, or a pharmaceutically acceptable salt, ester or prodrug thereof:

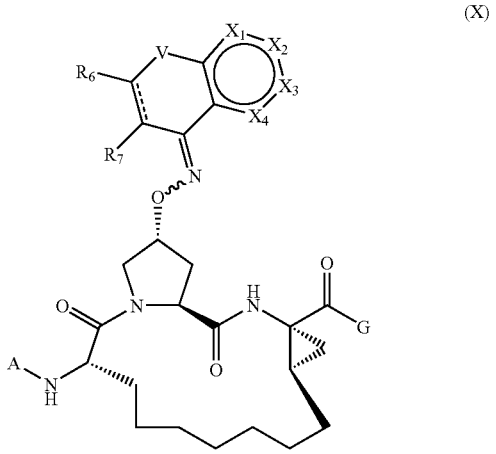

(X)

Where $X_1$-$X_4$ are independently selected from CO, CH, NH, O and N; and wherein $X_1$-$X_4$ can be further substituted when any one of $X_1$-$X_4$ is CH or NH; where $R_6$ and $R_7$ are independently $R_3$; where $R_3$ is independently selected from the group consisting of:
(i) hydrogen;
(ii) aryl;
(iii) substituted aryl;
(iv) heteroaryl;
(v) substituted heteroaryl;
(vi) heterocyclic;
(vii) substituted heterocyclic;
(viii) —$C_1$-$C_8$ alkyl, —$C_2$-$C_8$ alkenyl, or —$C_2$-$C_8$ alkynyl each containing 0, 1, 2, or 3 heteroatoms selected from O, S or N;
(ix) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
(x) —$C_3$-$C_{12}$ cycloalkyl, or —$C_3$-$C_{12}$ cycloalkenyl;
(xi) substituted —$C_3$-$C_{12}$ cycloalkyl, or substituted —$C_3$-$C_{12}$ cycloalkenyl;
and where A, G and V are as previously defined in the embodiment immediately above. Alternatively, $R_6$ and $R_7$ can be independently selected from halogen, oxo, thioxo, nitro, cyano, —$OR_3$, —$SR_3$, —$NR_3R_4$, —$SOR_3$, —$SO_2R_3$, —$NHSO_2R_3$, —$SO_2NHR_3$, —$COR_3$, —$CO_2R_3$, (CO)$NHR_3$, —$OCOR_3$, $OCONHR_3$, $NHCO_2R_3$, —$NH(CO)R_3$, —$NH(CO)NHR_3$, and —$NH(SO_2)NHR_3$.

In one example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of —$R_5$, —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$', —NH—C(O)—$R_3$', —NH—$SO_2$—NH—$R_3$' or —$NHSO_2$—$R_3$', where $R_3$' is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$', where $R_3$' is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$', where $R_3$' is selected from —$C_3$-$C_{12}$ cycloalkyl or substituted —$C_3$-$C_{12}$ cycloalkyl.

In yet another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted —$C_1$-$C_8$ alkyl (e.g., substituted methyl or ethyl) and is substituted with (1) aryl or heteroaryl, (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl, and optionally (3) one or more other substituents. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted methyl and is substituted at least with (1) aryl or heteroaryl and (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl. G is —NHSO$_2$—$R_3$, where $R_3$ is —$C_3$-$C_{12}$ cycloalkyl or substituted —$C_3$-$C_{12}$ cycloalkyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —$R_5$, where $R_5$ is —$C_1$-$C_8$ alkyl or substituted —$C_1$-$C_8$ alkyl. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In one embodiment, the present invention relates to a compound of formula XI, or a pharmaceutically acceptable salt, ester or prodrug thereof:

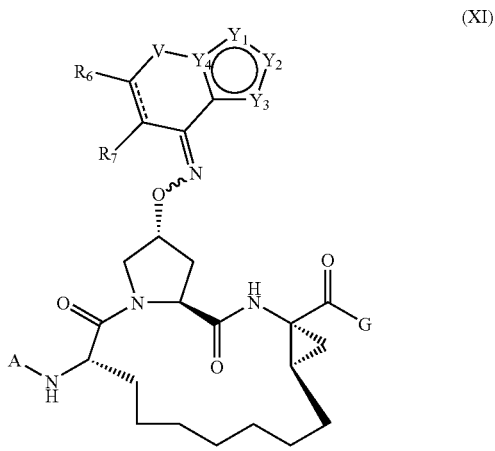

(XI)

Where $Y_1$-$Y_3$ are independently selected from CO, CH, NH, N, S and O; and where $Y_1$-$Y_3$ can be further substituted when any one of $Y_1$-$Y_3$ is CH or NH; $Y_4$ is selected from C, CH and N; and where A, G, $R_6$, $R_7$ and V are as previously defined.

In one example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of —$R_5$, —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$', —NH—C(O)—$R_3$', —NH—SO$_2$—NH—$R_3$' or —NHSO$_2$—$R_3$', where $R_3$' is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —NHSO$_2$—$R_3$', where $R_3$' is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$', where $R_3$' is selected from —$C_3$-$C_{12}$ cycloalkyl or substituted —$C_3$-$C_{12}$ cycloalkyl.

In yet another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted —$C_1$-$C_8$ alkyl (e.g., substituted methyl or ethyl) and is substituted with (1) aryl or heteroaryl, (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl, and optionally (3) one or more other substituents. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted methyl and is substituted at least with (1) aryl or heteroaryl and (2) —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHC(O)-aryl or —NHC(O)-heteroaryl. G is —NHSO$_2$—$R_3$, where $R_3$ is —$C_3$-$C_{12}$ cycloalkyl or substituted —$C_3$-$C_{12}$ cycloalkyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —$R_5$, where $R_5$ is —$C_1$-$C_8$ alkyl or substituted —$C_1$-$C_8$ alkyl. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In one embodiment of the present invention, there are disclosed compounds of formula XII:

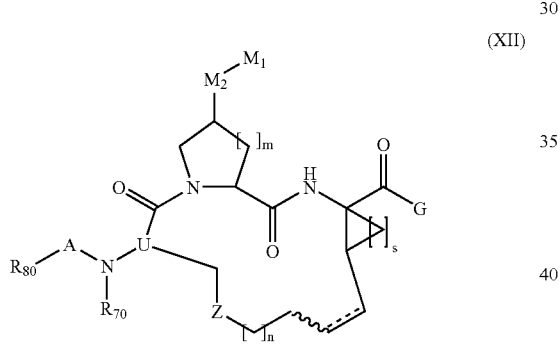

as well as the pharmaceutically acceptable salts, esters and prodrugs thereof, wherein:

$M_1$ is selected from the group consisting of:
(1) —N=CR$_{31}$R$_{32}$;
wherein $R_3$, and $R_{32}$ are independently selected from the group consisting of:
a) hydrogen;
b) aryl; substituted aryl;
c) heteroaryl; substituted heteroaryl;
d) —$C_1$-$C_8$ alkyl, —$C_2$-$C_8$ alkenyl, or —$C_2$-$C_8$ alkynyl containing 0, 1, 2, or 3 heteroatoms selected from O, S or N; optionally substituted with one or more substituents selected from halogen, aryl, substituted aryl, heteroaryl, or substituted heteroaryl;
e) —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic or substituted heterocyclic;
f) -A-$R_{30}$, where A is (CO), (CO)O, (CO)NR$_{40}$, (SO), (SO$_2$), (SO$_2$)NR$_{40}$; and $R_{30}$ and $R_{40}$ are independently selected from the group consisting of:

(i) Hydrogen;
(ii) aryl; substituted aryl; heteroaryl; substituted heteroaryl
(iii) —$C_1$-$C_8$ alkyl, —$C_2$-$C_8$ alkenyl, or —$C_2$-$C_8$ alkynyl containing 0, 1, 2, or 3 heteroatoms selected from O, S or N, optionally substituted with one or more substituents selected from halogen, aryl, substituted aryl, heteroaryl, or substituted heteroaryl; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic or substituted heterocyclic;

with added proviso that when A=CO, (CO)O, (SO), (SO$_2$), $R_{30}$ is not hydrogen; with added proviso that when $R_{31}$=hydrogen, $R_{32}$ is not hydrogen;

alternatively, $R_{31}$ and $R_{32}$ are taken together with the carbon atom to which they are attached to form the group consisting of:
a) —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl heterocyclic or substituted heterocyclic;
b) —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl; heterocyclic or substituted heterocyclic fused with one or more substituents selected from aryl, substituted aryl, heteroaryl, substituted heteroaryl, —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl; heterocyclic or substituted heterocyclic;
c)

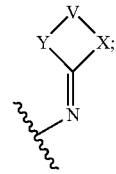

wherein V is absent, or V is O, S, SO, SO$_2$, NR$_{50}$, or (CH$_2$)$_q$; where $R_{50}$ is selected from H, OH, OCH$_3$, —O—$C_1$-$C_8$ alkyl, —$C_1$-$C_8$ alkyl, —O—$C_3$-$C_8$ cycloalkyl, —$C_3$-$C_8$ cycloalkyl, —O—$C_3$-$C_8$ cycloalkenyl; —$C_3$-$C_8$ cycloalkenyl; where q is 1, 2, 3 or 4; and where X and Y are independently selected from the group consisting of:
(i) aryl; substituted aryl;
(ii) heteroaryl; substituted heteroaryl;
(iii) heterocyclic; substituted heterocyclic;
(2) NR$_{30}$R$_{40}$; NR$_5$(CO)R$_{30}$; NR$_{50}$(CO)OR$_{30}$; NR$_{50}$(CO)NR$_{30}$R$_{40}$; NR$_{50}$(SO$_2$)OR$_{30}$; NR$_{50}$(SO$_2$)NR$_{30}$R$_{40}$; where $R_{30}$, $R_{40}$ and $R_{50}$ are as previously defined; alternatively, for formula (I), $R_{30}$ and $R_{40}$ are taken together with the nitrogen atom to which they are attached to form the group consisting of: heterocyclic, or substituted heterocyclic; heteroaryl, or substituted heteroaryl;

$M_2$ is selected from the group consisting of:
(1) oxygen;
(2) sulfur;
(3) NR$_{60}$; where $R_{60}$ is selected from H, OH, OCH$_3$, —O—$C_1$-$C_8$ alkyl, —$C_1$-$C_8$ alkyl;

G is -E-$R_{30}$; and where E is absent, or E is O, CO, (CO)O, (CO)NH, NH, NH(CO), NH(CO)NH, NH(CNR$_{50}$)NH, NH(SO$_2$)NH or NHSO$_2$; where $R_{30}$ and $R_{50}$ are as previously defined;

Z is selected from the group consisting of $CH_2$, O, CO, (CO)O, (CO)NH, S, SO, $SO_2$, CF, $CF_2$, aryl, substituted aryl, heteroaryl and substituted heteroaryl;

n=0, 1, 2, 3 or 4;

U is CH, CF or N;

$R_{70}$ is selected from the group consisting of H, OH, $OCH_3$, —O—$C_1$-$C_8$ alkyl, —$C_1$-$C_8$ alkyl;

J is selected from the group consisting of CO, (CO)O, (CO)$NR_{50}$, $SO_2$, ($SO_2$)O or $SO_2NR_{50}$;

$R_{80}$ is selected from the group consisting of:
(1) hydrogen;
(2) aryl; substituted aryl; heteroaryl; substituted heteroaryl;
(3) —$C_1$-$C_8$ alkyl, —$C_2$-$C_8$ alkenyl, or —$C_2$-$C_8$ alkynyl containing 0, 1, 2, or 3 heteroatoms selected from O, S or N, optionally substituted with one or more substituents selected from halogen, aryl, substituted aryl, heteroaryl, or substituted heteroaryl; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic or substituted heterocyclic;

with added proviso that when J=CO, (CO)O, (SO), ($SO_2$), $R_{80}$ is not hydrogen;

m=0, 1, 2 or 3; and s=0, 1, 2 or 3.

In another embodiment of the present invention relates to compound of formula XIII, or a pharmaceutically acceptable salt, ester or prodrug thereof:

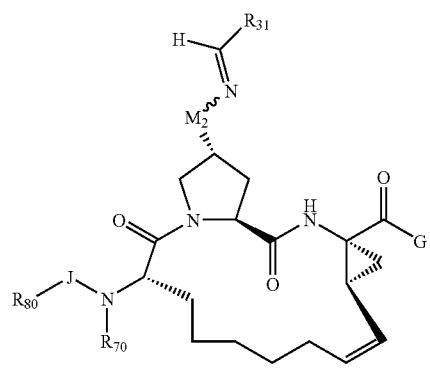

(XIII)

where G, J, $M_2$, $R_{31}$, $R_{70}$, and $R_{80}$ are as previously defined in the embodiment immediately above, with added proviso $R_{31}$ is not hydrogen.

Yet another embodiment of the present invention relates to compound of formula XIV, or a pharmaceutically acceptable salt, ester or prodrug thereof:

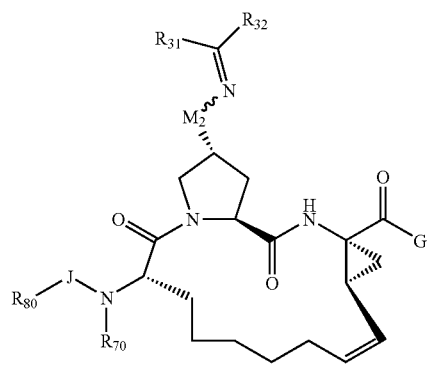

(XIV)

where G, J, $M_2$, $R_{31}$, $R_{32}$, $R_{70}$, and $R_{80}$ are as previously defined in the embodiment above.

In another embodiment of the present invention relates to compound of formula XV, or a pharmaceutically acceptable salt, ester or prodrug thereof:

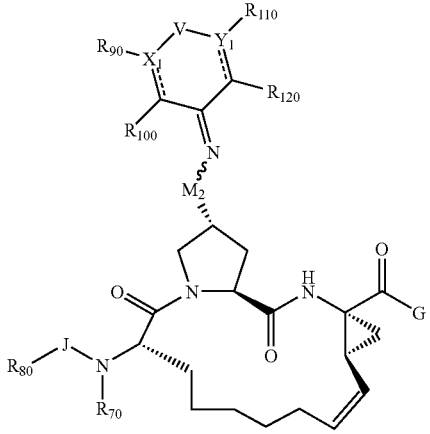

(XV)

Where $X_1$ and $Y_1$ are independently selected from CH and N; $R_{90}$, $R_{100}$, $R_{110}$, and $R_{120}$ are independently $R_{30}$; G, J, $M_2$, $R_{70}$, and $R_{80}$ are as previously defined in the embodiment above.

In one embodiment of the present invention relates to compound of formulae XVI, or a pharmaceutically acceptable salt, ester or prodrug thereof:

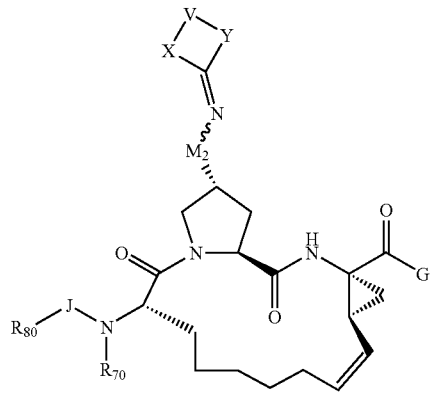

(XVI)

where G, J, $M_2$, $R_{70}$, $R_{80}$, V, X and Y are as previously defined in the embodiment above.

In another embodiment of the present invention relates to compound of formula XVII, or a pharmaceutically acceptable salt, ester or prodrug thereof:

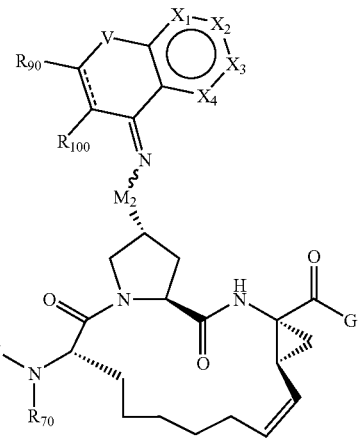

(XVII)

Where $X_1$-$X_4$ are independently selected from CH and N; $X_1$-$X_4$ can be further substituted when it is a CH; where G, J, $M_2$, $R_{70}$, $R_{80}$, $R_{90}$, $R_{100}$ and V are as previously defined in the embodiment above.

In another embodiment of the present invention relates to compound of formula XVIII, or a pharmaceutically acceptable salt, ester or prodrug thereof:

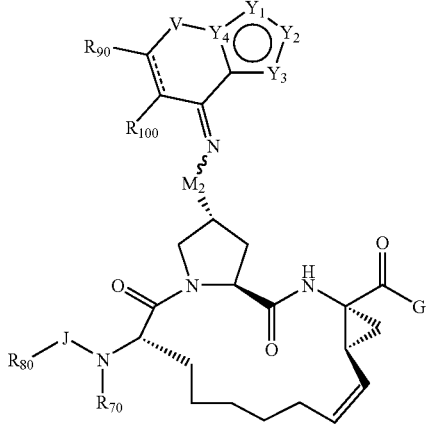

(XVIII)

Where $Y_1$-$Y_3$ are independently selected from CH, N, NH, S and O; and $Y_1$-$Y_3$ can be further substituted when it is CH or NH; $Y_4$ is selected from CH and N; where G, J, $M_2$, $R_{70}$, $R_{80}$, $R_{90}$, $R_{100}$ and V are as previously defined.

In one embodiment of the present invention relates to compound of formula XIX or a pharmaceutically acceptable salt, ester or prodrug thereof:

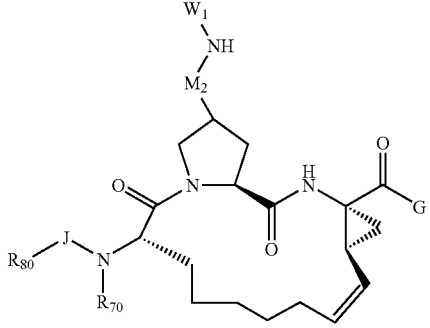

(XIX)

where $W_1$ is hydrogen, $R_{30}$, $COR_{30}$, $CONR_{30}R_{40}$, $SOR_{30}$, $SO_2NR_{30}R_{40}$; G, J, $M_2$, $R_{70}$ and $R_{80}$ are as previously defined.

In one embodiment of the present invention relates to compound of formula XX, or a pharmaceutically acceptable salt, ester or prodrug thereof:

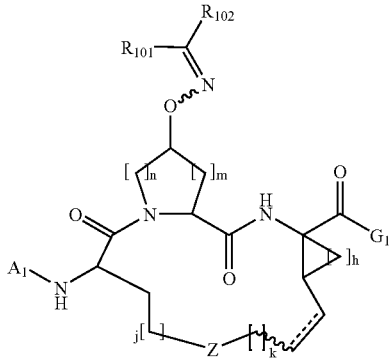

(XX)

as well as the pharmaceutically acceptable salts, esters and prodrugs thereof, wherein:

$R_{101}$ and $R_{102}$ are independently selected from the group consisting of:
a) hydrogen;
b) aryl;
c) substituted aryl;
d) heteroaryl fused with 0, 1, 2, or 3 more group selected from heteroaryl and aryl;
e) substituted heteroaryl fused with 0, 1, 2 or 3 more group selected from heteroaryl, substituted heteroaryl, aryl and substituted aryl;
f) heterocyclic, substituted heterocyclic, or oxo substituted heterocyclic; wherein oxo refer to substituted by independent replacement of two of the hydrogen atoms thereon with =O;
g) —$C_1$-$C_8$ alkyl, —$C_2$-$C_8$ alkenyl, or —$C_2$-$C_8$ alkynyl each containing 0, 1, 2, or 3 heteroatoms selected from O, S or N;
h) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
i) —$C_3$-$C_{12}$ cycloalkyl, or —$C_3$-$C_{12}$ cycloalkenyl;
j) substituted —$C_3$-$C_{12}$ cycloalkyl, or substituted —$C_3$-$C_{12}$ cycloalkenyl;
k) oxo substituted —$C_3$-$C_{12}$ cycloalkyl, or oxo substituted —$C_3$-$C_{12}$ cycloalkenyl;
l) —B—$R_{103}$, where B is (CO), (CO)O, (CO)$NR_{104}$, (SO), (SO$_2$), (SO$_2$)$NR_{104}$; and $R_{103}$ and $R_{104}$ are independently selected from the group consisting of:
(i) hydrogen;
(ii) aryl;
(iii) substituted aryl;
(iv) heteroaryl fused with 0, 1, 2, or 3 more group selected from aryl and heteroaryl;
(v) substituted heteroaryl fused with 0, 1, 2 or 3 more group selected from heteroaryl, substituted heteroaryl, aryl and substituted aryl;
(vi) heterocyclic;
(vii) substituted heterocyclic;
(viii) oxo substituted heterocyclic;
(ix) —$C_1$-$C_8$ alkyl, —$C_2$-$C_8$ alkenyl, or —$C_2$-$C_8$ alkynyl each containing 0, 1, 2, or 3 heteroatoms selected from O, S or N;
(x) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
(xi) —$C_3$-$C_{12}$ cycloalkyl, or —$C_3$-$C_{12}$ cycloalkenyl;
(xii) substituted —$C_3$-$C_{12}$ cycloalkyl, substituted —$C_3$-$C_{12}$ cycloalkenyl, oxo substituted —$C_3$-$C_{12}$ cycloalkyl, or oxo substituted —$C_3$-$C_{12}$ cycloalkenyl;

or $R_{101}$ and $R_{102}$ taken together with the carbon atom to which they are attached form a cyclic moiety selected from: substituted or unsubstituted cycloalkyl, cycloalkenyl, or heterocyclic; substituted or unsubstituted cycloalkyl, cycloalkenyl, or heterocyclic each substituted with an oxo; substituted or unsubstituted cycloalkyl, cycloalkenyl, or heterocyclic each fused with one or more $R_{103}$; or oxo substituted or unsubstituted cycloalkyl, cycloalkenyl, or heterocyclic each fused with one or more $R_{103}$;

$G_1$ is -E-$R_{103}$, where E is absent or E is O, CO, (CO)O, (CO)NH, NH, NH(CO), NH(CO)NH, NH(SO$_2$)NH or NHSO$_2$;

Z is selected from the group consisting of CH$_2$, O, S, SO, or SO$_2$;

A is selected from the group consisting of $R_{105}$, $(CO)R_{105}$, $(CO)OR_{105}$, $(CO)NHR_{105}$, $SO_2R105_5$, $(SO_2)OR_{105}$ and $SO_2NHR_{105}$;

$R_{105}$ is selected from the group consisting of: aryl;
  a) hydrogen
  b) substituted aryl;
  c) heteroaryl fused with 0, 1, 2, or 3 more group selected from heteroaryl and aryl;
  d) substituted heteroaryl fused with 0, 1, 2 or 3 more group selected from heteroaryl, substituted heteroaryl, aryl and substituted aryl;
  e) heterocyclic;
  f) substituted heterocyclic;
  g) oxo substituted heterocyclic;
  h) —$C_1$-$C_8$ alkyl, —$C_2$-$C_8$ alkenyl, or —$C_2$-$C_8$ alkynyl each containing 0, 1, 2, or 3 heteroatoms selected from O, S or N;
  i) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
  j) —$C_3$-$C_{12}$ cycloalkyl, or —$C_3$-$C_{12}$ cycloalkenyl;
  k) substituted —$C_3$-$C_{12}$ cycloalkyl, substituted —$C_3$-$C_{12}$ cycloalkenyl, oxo substituted —$C_3$-$C_{12}$ cycloalkyl, or oxo substituted —$C_3$-$C_{12}$ cycloalkenyl;

j=0, 1, 2, or 3;
k=0, 1, 2, or 3; and
m=0, 1, 2 or 3;
n=1, 2 or 3 and
h=0, 1, 2, or 3.

Representative compounds according to the invention are those selected from the group consisting of:

Compounds (1)-(2) of the Formula A:

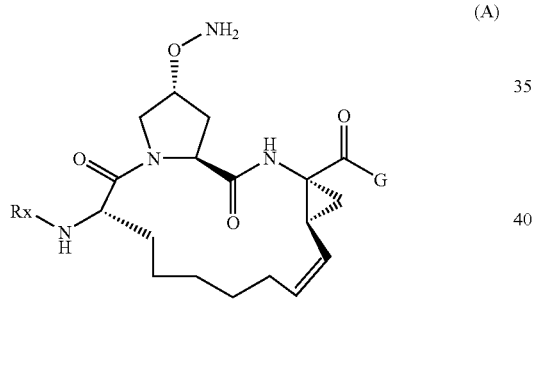

(A)

Rx and G are Delineated for Each Example in TABLE 1:

TABLE 1

| Compound | Rx | G |
|---|---|---|
| (1) | *t*-butyl-O-C(O)-CH(CH$_3$)- | OEt |
| (2) | cyclopentyl-O-C(O)-CH(CH$_3$)- | OEt |

Compounds (3)-(113) of the Formula B:

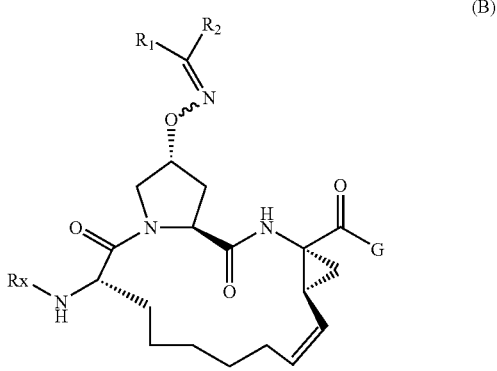

(B)

$R_1$, $R_2$, Rx and G are Delineated for each Example in TABLE 2:

TABLE 2

| Compound | Rx | $R_1$ | $R_2$ | G |
|---|---|---|---|---|
| (3) | cyclopentyl-O-C(O)-CH(CH$_3$)- | —CH$_3$ | —Ph | —OH |
| (4) | cyclopentyl-O-C(O)-CH(CH$_3$)- | —CH$_2$CH$_3$ | —Ph | —OH |
| (5) | cyclopentyl-O-C(O)-CH(CH$_3$)- | —CH$_2$CH$_2$CH$_3$ | —Ph | —OH |

TABLE 2-continued
| Compound | Rx | R₁ | R₂ | G |
|---|---|---|---|---|
| (6) | 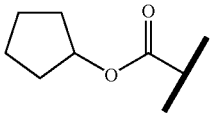 | —CH₂OCH₃ | —Ph | —OH |
| (7) | 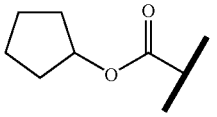 | —Ph | —Ph | —OH |
| (8) | 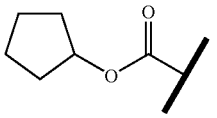 | —Ph | 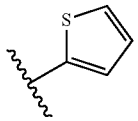 | —OH |
| (9) | 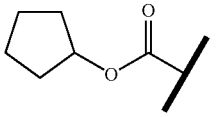 | 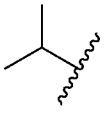 [SMILES: *C(C)C] | —Ph | —OH |
| (10) | 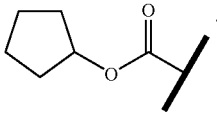 | 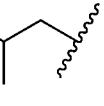 | —Ph | —OH |
| (11) | 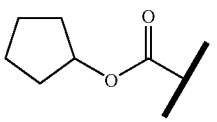 | 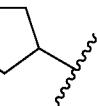 | —Ph | —OH |
| (12) | 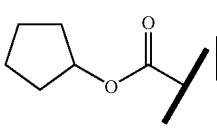 | 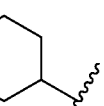 | —Ph | —OH |
| (13) | 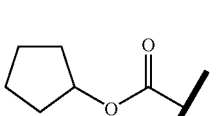 | —H | —Ph | —OH |
| (14) | 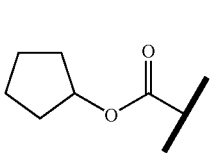 | —H | 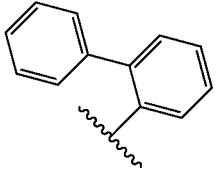 [SMILES: *c1ccccc1-c1ccccc1] | —OH |
| (15) | 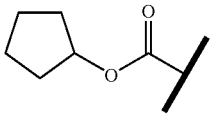 | —H | 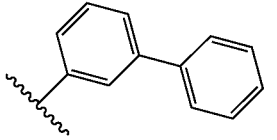 [SMILES: *c1cccc(-c2ccccc2)c1] | —OH |

TABLE 2-continued
| Compound | Rx | R$_1$ | R$_2$ | G |
|---|---|---|---|---|
| (16) | 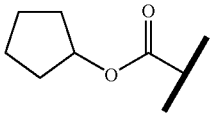 | —H | 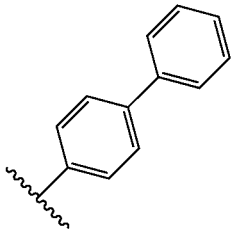 [SMILES: *c1ccc(-c2ccccc2)cc1] | —OH |
| (17) | 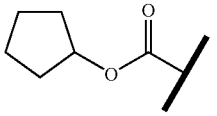 | —H |  | —OH |
| (18) | 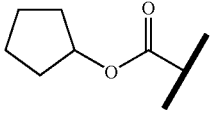 | —H | 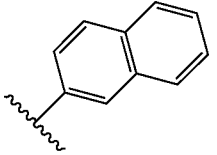 [SMILES: *c1ccc2ccccc2c1] | —OH |
| (19) | 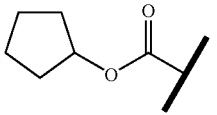 | —CH$_2$CH$_3$ | 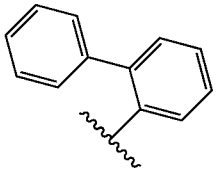 [SMILES: *c1ccccc1-c1ccccc1] | —OH |
| (20) | 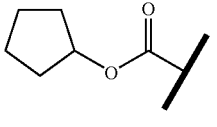 | —H | 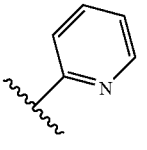 [SMILES: *c1ccccn1] | —OH |
| (21) | 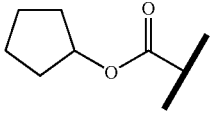 | —H | 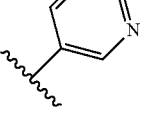 | —OH |
| (22) | 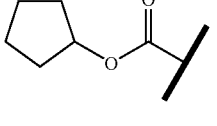 | —H | 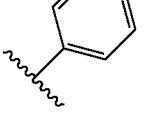 | —OH |
| (23) | 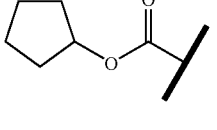 | —H | 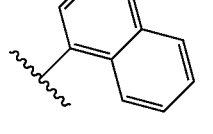 | —OH |
| (24) | 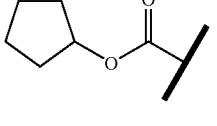 | —H | 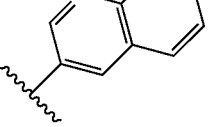 | —OH |

TABLE 2-continued

| Compound | Rx | R₁ | R₂ | G |
|---|---|---|---|---|
| (25) | cyclopentyl-O-C(=O)-CH< | —H | 2-methoxyphenyl | —OH |
| (26) | cyclopentyl-O-C(=O)-CH< | —H | 3-methoxyphenyl | —OH |
| (27) | cyclopentyl-O-C(=O)-CH< | —H | 4-methoxyphenyl | —OH |
| (28) | cyclopentyl-O-C(=O)-CH< | —H | 2-fluorophenyl | —OH |
| (29) | cyclopentyl-O-C(=O)-CH< | —H | 3-fluorophenyl | —OH |
| (30) | cyclopentyl-O-C(=O)-CH< | —H | 4-fluorophenyl | —OH |
| (31) | cyclopentyl-O-C(=O)-CH< | —H | 2-(thiophen-2-yl)phenyl | —OH |
| (32) | cyclopentyl-O-C(=O)-CH< | —H | 2-(1H-pyrazol-1-yl)phenyl | —OH |
| (33) | cyclopentyl-O-C(=O)-CH< | —H | 2-(1H-1,2,4-triazol-1-yl)phenyl | —OH |

TABLE 2-continued
| Compound | Rx | R₁ | R₂ | G |
|---|---|---|---|---|
| (34) | 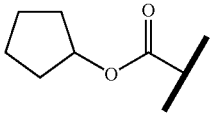 | —H | 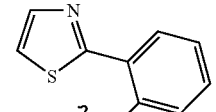 | —OH |
| (35) | 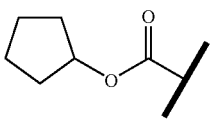 | —H | 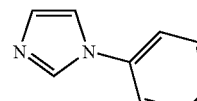 | —OH |
| (36) | 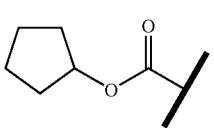 | —H | 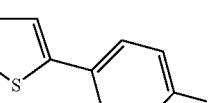 | —OH |
| (37) | 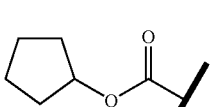 | —H | 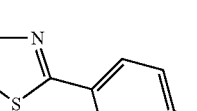 | —OH |
| (38) | 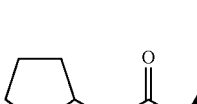 | —H | 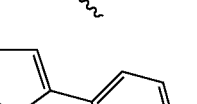 | 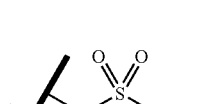 |
| (39) | 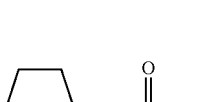 | —H |  | 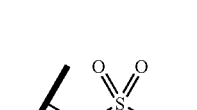 |
| (40) | 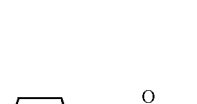 | —H |  | 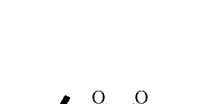 |
| (41) |  | —H |  | —OH |
| (42) | 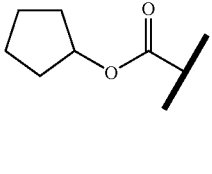 | —H | 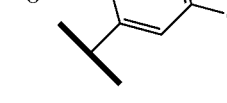 |  |

TABLE 2-continued

| Compound | Rx | R₁ | R₂ | G |
|---|---|---|---|---|
| (43) | tert-butyl ester group | —Ph | —Ph | —OH |
| (44) | tert-butyl ester group | —CH₃ | —Ph | —OH |
| (45) | tert-butyl ester group | —H | —Ph | —OH |
| (46) | cyclopentyl ester group | —CH₃ | —Ph | —NHSO₂-cyclopropyl |
| (47) | cyclopentyl ester group | —CH₂CH₃ | —Ph | —NHSO₂-cyclopropyl |
| (48) | cyclopentyl ester group | —CH₂CH₂CH₃ | —Ph | —NHSO₂-cyclopropyl |
| (49) | cyclopentyl ester group | —CH₂OCH₃ | —Ph | —NHSO₂-cyclopropyl |
| (50) | cyclopentyl ester group | —Ph | —Ph | —NHSO₂-cyclopropyl |
| (51) | cyclopentyl ester group | —Ph | 2-thienyl | —NHSO₂-cyclopropyl |
| (52) | cyclopentyl ester group | isopropyl | —Ph | —NHSO₂-cyclopropyl |
| (53) | cyclopentyl ester group | isobutyl | —Ph | —NHSO₂-cyclopropyl |

TABLE 2-continued

| Compound | Rx | R₁ | R₂ | G |
|---|---|---|---|---|
| (54) | cyclopentyl ester | cyclopentyl | —Ph | —NH-S(O)₂-cyclopropyl |
| (55) | cyclopentyl ester | cyclohexyl | —Ph | —NH-S(O)₂-cyclopropyl |
| (56) | cyclopentyl ester | —H | —Ph | —NH-S(O)₂-cyclopropyl |
| (57) | cyclopentyl ester | —H | 3-biphenyl | —NH-S(O)₂-cyclopropyl |
| (58) | cyclopentyl ester | —H | 4-biphenyl | —NH-S(O)₂-cyclopropyl |
| (59) | cyclopentyl ester | —H | 1-naphthyl | —NH-S(O)₂-cyclopropyl |
| (60) | cyclopentyl ester | —H | 2-naphthyl | —NH-S(O)₂-cyclopropyl |
| (61) | cyclopentyl ester | —CH₂CH₃ | 2-biphenyl | —NH-S(O)₂-cyclopropyl |
| (62) | cyclopentyl ester | —H | 2-pyridyl | —NH-S(O)₂-cyclopropyl |

TABLE 2-continued

| Compound | Rx | R₁ | R₂ | G |
|---|---|---|---|---|
| (63) | cyclopentyl-O-C(=O)- | —H | pyridin-3-yl | —NH-S(=O)₂-cyclopropyl |
| (64) | cyclopentyl-O-C(=O)- | —H | pyridin-4-yl | —NH-S(=O)₂-cyclopropyl |
| (65) | cyclopentyl-O-C(=O)- | —H | quinolin-4-yl | —NH-S(=O)₂-cyclopropyl |
| (66) | cyclopentyl-O-C(=O)- | —H | quinolin-3-yl | —NH-S(=O)₂-cyclopropyl |
| (67) | cyclopentyl-O-C(=O)- | —H | 2-methoxyphenyl | —NH-S(=O)₂-cyclopropyl |
| (68) | cyclopentyl-O-C(=O)- | —H | 3-methoxyphenyl | —NH-S(=O)₂-cyclopropyl |
| (69) | cyclopentyl-O-C(=O)- | —H | 4-methoxyphenyl | —NH-S(=O)₂-cyclopropyl |
| (70) | cyclopentyl-O-C(=O)- | —H | 2-fluoropyridin-3-yl | —NH-S(=O)₂-cyclopropyl |
| (71) | cyclopentyl-O-C(=O)- | —H | 3-fluorophenyl | —NH-S(=O)₂-cyclopropyl |
| (72) | cyclopentyl-O-C(=O)- | —H | 4-fluorophenyl | —NH-S(=O)₂-cyclopropyl |

TABLE 2-continued
| Compound | Rx | R₁ | R₂ | G |
|---|---|---|---|---|
| (73) | 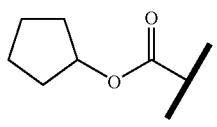 | —H | 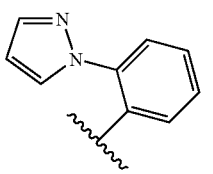 | 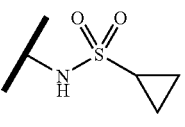 |
| (74) | 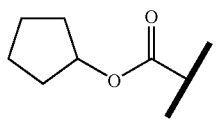 | —H | 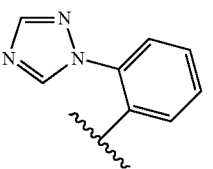 [SMILES: *c1ccccc1-n1cncn1] | 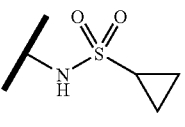 |
| (75) | 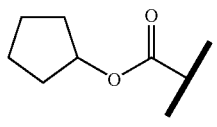 | —H | 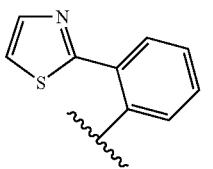 [SMILES: *c1ccccc1-c1nccs1] | 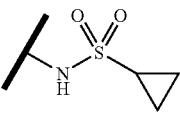 |
| (76) | 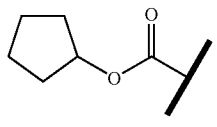 | —H | 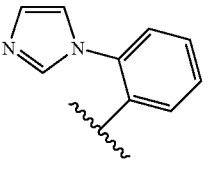 [SMILES: *c1ccccc1-n1ccnc1] | 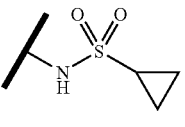 |
| (77) | 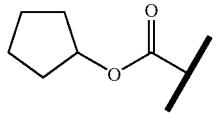 | —H | 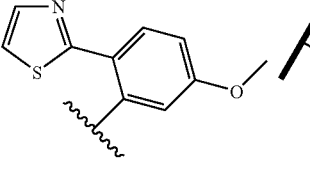 | 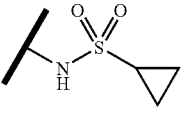 |
| (78) | 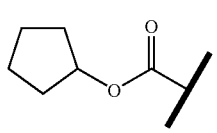 | —Ph | —Ph | 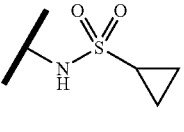 |
| (79) | 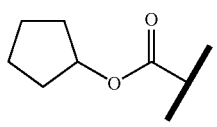 | —CH₃ | —Ph | 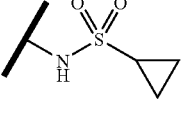 |
| (80) | 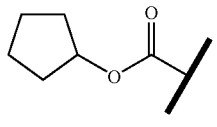 | —H | —Ph | 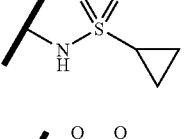 |
| (81) | 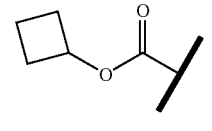 | —CH₃ | —Ph | 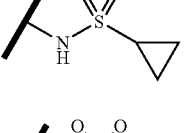 |
| (82) | 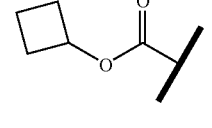 | —CH₂CH₃ | —Ph | 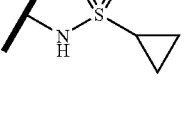 |

TABLE 2-continued

| Compound | Rx | R₁ | R₂ | G |
|---|---|---|---|---|
| (83) | cyclobutyl-O-C(=O)- | —CH₂CH₂CH₃ | —Ph | —NH-S(O)₂-cyclopropyl |
| (84) | cyclobutyl-O-C(=O)- | —CH₂OCH₃ | —Ph | —NH-S(O)₂-cyclopropyl |
| (85) | cyclobutyl-O-C(=O)- | —Ph | —Ph | —NH-S(O)₂-cyclopropyl |
| (86) | cyclobutyl-O-C(=O)- | —Ph | 2-thienyl | —NH-S(O)₂-cyclopropyl |
| (87) | cyclobutyl-O-C(=O)- | isobutyl | —Ph | —NH-S(O)₂-cyclopropyl |
| (88) | cyclobutyl-O-C(=O)- | isopentyl | —Ph | —NH-S(O)₂-cyclopropyl |
| (89) | cyclobutyl-O-C(=O)- | cyclopentyl | —Ph | —NH-S(O)₂-cyclopropyl |
| (90) | cyclobutyl-O-C(=O)- | cyclohexyl | —Ph | —NH-S(O)₂-cyclopropyl |
| (91) | cyclobutyl-O-C(=O)- | —H | —Ph | —NH-S(O)₂-cyclopropyl |
| (92) | cyclobutyl-O-C(=O)- | —H | 2-biphenyl | —NH-S(O)₂-cyclopropyl |
| (93) | cyclobutyl-O-C(=O)- | —H | 3-biphenyl | —NH-S(O)₂-cyclopropyl |

TABLE 2-continued
| Compound | Rx | R₁ | R₂ | G |
|---|---|---|---|---|
| (94) | 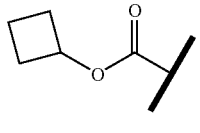 | —H | 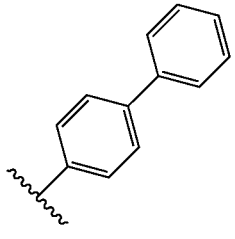 [SMILES: *c1ccc(-c2ccccc2)cc1] | 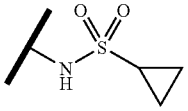 |
| (95) | 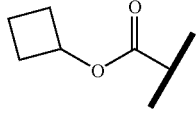 | —H | 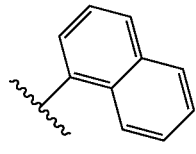 | 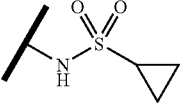 |
| (96) | 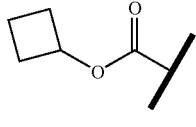 | —H | 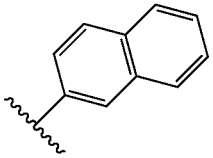 [SMILES: *c1ccc2ccccc2c1] | 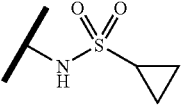 |
| (97) | 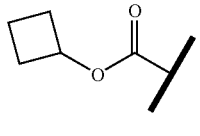 | —CH₂CH₃ | 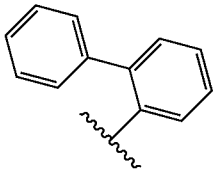 [SMILES: *c1ccccc1-c1ccccc1] | 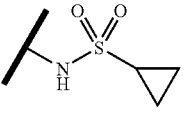 |
| (98) | 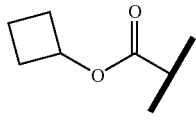 | —H | 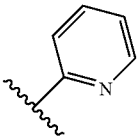 [SMILES: *c1ccccn1] | 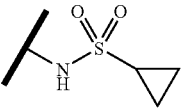 |
| (99) | 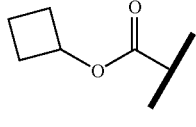 | —H | 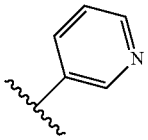 [SMILES: *c1cccnc1] | 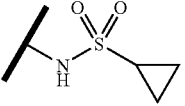 |
| (100) | 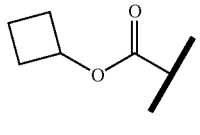 | —H | 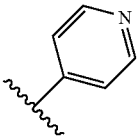 [SMILES: *c1ccncc1] | 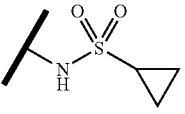 |
| (101) | 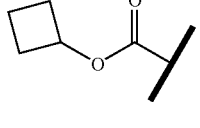 | —H | 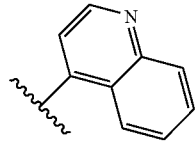 [SMILES: *c1ccnc2ccccc12] | 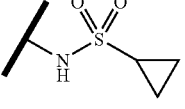 |
| (102) | 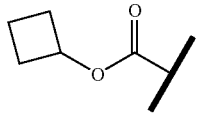 | —H | 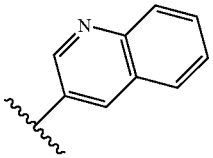 [SMILES: *c1cnc2ccccc2c1] | 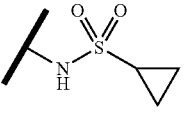 |

TABLE 2-continued

| Compound | Rx | R₁ | R₂ | G |
|---|---|---|---|---|
| (103) | cyclobutyl-O-C(=O)-CH< | —H | 2-methoxyphenyl | -NH-S(=O)₂-cyclopropyl |
| (104) | cyclobutyl-O-C(=O)-CH< | —H | 3-methoxyphenyl | -NH-S(=O)₂-cyclopropyl |
| (105) | cyclobutyl-O-C(=O)-CH< | —H | 4-methoxyphenyl | -NH-S(=O)₂-cyclopropyl |
| (106) | cyclobutyl-O-C(=O)-CH< | —H | 2-fluorophenyl | -NH-S(=O)₂-cyclopropyl |
| (107) | cyclobutyl-O-C(=O)-CH< | —H | 3-fluorophenyl | -NH-S(=O)₂-cyclopropyl |
| (108) | cyclobutyl-O-C(=O)-CH< | —H | 4-fluorophenyl | -NH-S(=O)₂-cyclopropyl |
| (109) | cyclobutyl-O-C(=O)-CH< | —H | 2-(thiophen-2-yl)phenyl | -NH-S(=O)₂-cyclopropyl |
| (110) | cyclobutyl-O-C(=O)-CH< | —H | 2-(1H-pyrazol-1-yl)phenyl | -NH-S(=O)₂-cyclopropyl |
| (111) | cyclobutyl-O-C(=O)-CH< | —H | 2-(1H-1,2,4-triazol-1-yl)phenyl | -NH-S(=O)₂-cyclopropyl |

TABLE 2-continued

| Compound | Rx | R₁ | R₂ | G |
|---|---|---|---|---|
| (112) | cyclobutyl-O-C(=O)-CH< | —H | 2-(thiazol-2-yl)phenyl | —NH-S(=O)₂-cyclopropyl |
| (113) | cyclobutyl-O-C(=O)-CH< | —H | 2-(imidazol-1-yl)phenyl | —NH-S(=O)₂-cyclopropyl |
| (114) | cyclobutyl-O-C(=O)-CH< | —H | 2-(thiophen-2-yl)-4-methoxyphenyl | —NH-S(=O)₂-cyclopropyl |
| (115) | cyclobutyl-O-C(=O)-CH< | —H | 2-(thiazol-2-yl)-4-methoxyphenyl | —NH-S(=O)₂-cyclopropyl |

Further representative species of the present invention are:

Compounds (116)-(204) of the Formula B: where R₁ and R₂ taken together to form R₁R₂, Rx and G are delineated for each example in TABLE 3:

TABLE 3

| Compound | Rx | R₁R₂ | G |
|---|---|---|---|
| (116) | cyclopentyl-O-C(=O)-CH< | fluorenylidene | —OH |
| (117) | cyclopentyl-O-C(=O)-CH< | 4,5-diaza-fluorenylidene | —OH |
| (118) | cyclopentyl-O-C(=O)-CH< | 1,8-diaza-fluorenylidene | —OH |

TABLE 3-continued

| Compound | Rx | R₁R₂ | G |
|---|---|---|---|
| (119) | cyclopentyl ester | N-methyl acridine | —OH |
| (120) | cyclopentyl ester | anthracen-9(10H)-one | —OH |
| (121) | cyclopentyl ester | 10,11-dihydro-5H-dibenzo[a,d][7]annulene | —OH |
| (122) | cyclopentyl ester | indane | —OH |
| (123) | cyclopentyl ester | tetrahydronaphthalene | —OH |
| (124) | cyclopentyl ester | methoxy-tetrahydronaphthalene | —OH |
| (125) | cyclopentyl ester | methoxy-tetrahydronaphthalene | —OH |
| (126) | cyclopentyl ester | dimethoxy-tetrahydronaphthalene | —OH |
| (127) | cyclopentyl ester | tetrahydroquinoline | —OH |

TABLE 3-continued
| Compound | Rx | R₁R₂ | G |
|---|---|---|---|
| (128) | 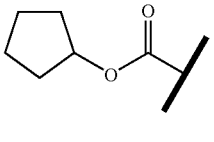 | 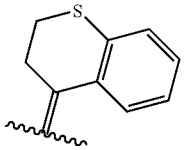 [SMILES: *=C1CCSc2ccccc21] | —OH |
| (129) | 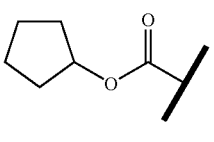 | 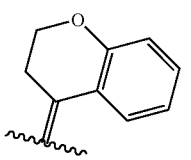 [SMILES: *=C1CCOc2ccccc21] | —OH |
| (130) | 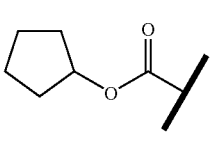 | 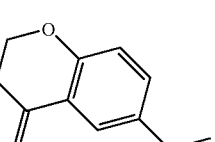 | —OH |
| (131) | 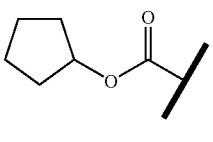 | 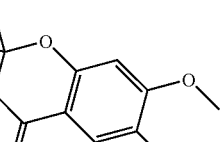 | —OH |
| (132) | 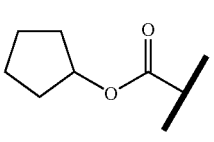 | 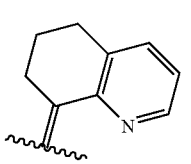 | —OH |
| (133) | 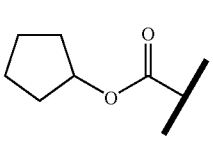 | 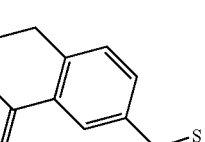 | —OH |
| (134) | 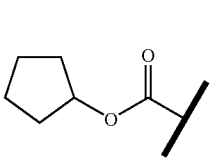 | 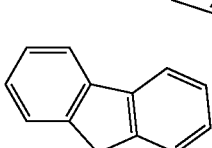 | 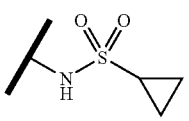 |
| (135) | 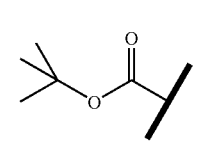 | 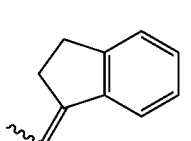 | —OH |
| (136) | 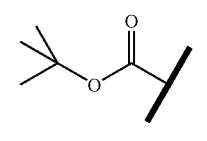 | 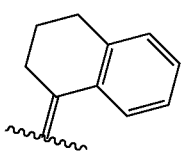 | —OH |

TABLE 3-continued

| Compound | Rx | R₁R₂ | G |
|---|---|---|---|
| (137) | cyclopentyl ester | diazafluorene | -NHS(O)₂-cyclopropyl |
| (138) | cyclopentyl ester | fluorene | -NH-tetrazole |
| (139) | tert-butyl ester | xanthene | -OH |
| (140) | tert-butyl ester | xanthene | -NHS(O)₂-cyclopropyl |
| (141) | cyclopentyl ester | xanthene | -NHS(O)₂-cyclopropyl |
| (142) | tert-butyl ester | 2-phenyl-4H-chromene | -OH |
| (143) | tert-butyl ester | 2-phenyl-4H-chromene | -NHS(O)₂-cyclopropyl |
| (144) | cyclopentyl ester | 2-phenyl-4H-chromene | -NHS(O)₂-cyclopropyl |

TABLE 3-continued
| Compound | Rx | R₁R₂ | G |
|---|---|---|---|
| (145) | 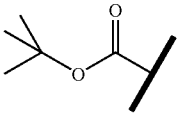 | 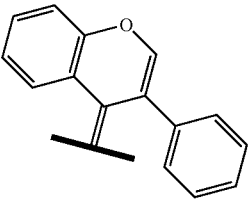 | —OH |
| (146) | 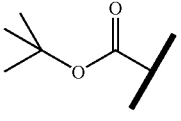 | 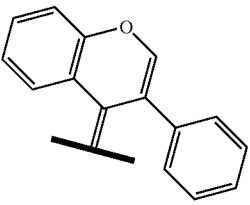 | 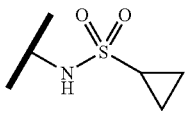 |
| (147) | 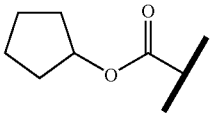 | 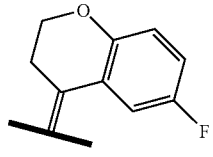 | —OH |
| (148) | 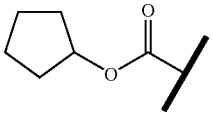 | 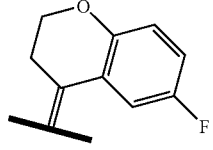 | 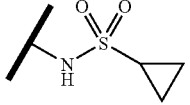 |
| (149) | 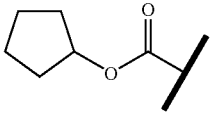 | 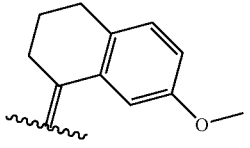 [SMILES: *=C1CCCc2ccc(OC)cc21] | 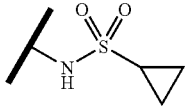 |
| (150) | 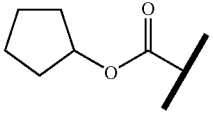 | 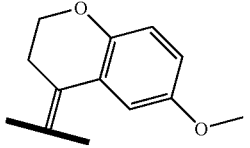 | 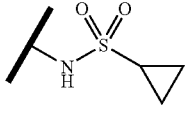 |
| (151) | 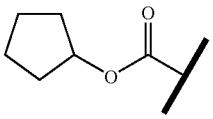 | 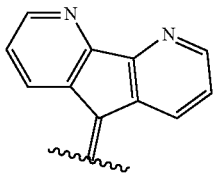 [SMILES: *=C1c2cccnc2-c2ncccc21] | 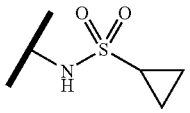 |
| (152) | 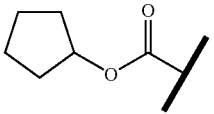 | 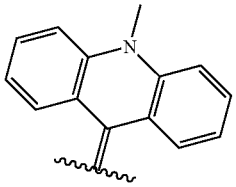 [SMILES: *=C1c2ccccc2N(C)c2ccccc21] | 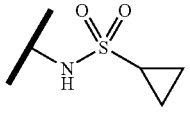 |

TABLE 3-continued
| Compound | Rx | R₁R₂ | G |
|---|---|---|---|
| (153) | 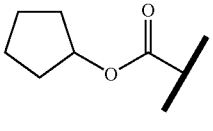 | 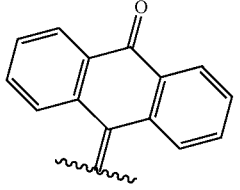 [SMILES: *=C1c2ccccc2C(=O)c2ccccc21] | 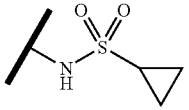 |
| (154) | 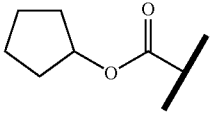 | 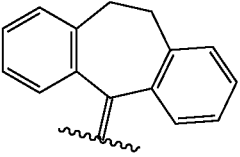 [SMILES: *=C1c2ccccc2CCc2ccccc21] | 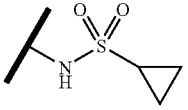 |
| (155) | 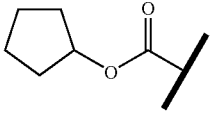 | 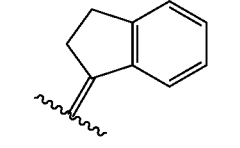 [SMILES: *=C1CCc2ccccc21] | 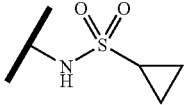 |
| (156) | 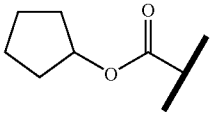 | 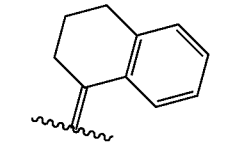 | 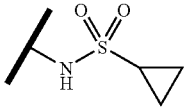 |
| (157) | 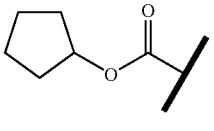 | 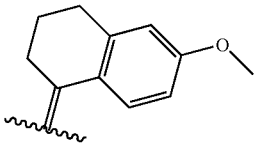 [SMILES: *=C1CCCc2cc(OC)ccc21] | 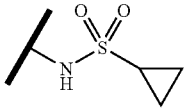 |
| (158) | 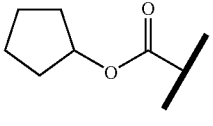 | 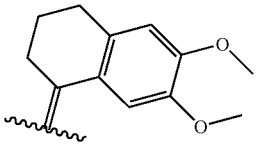 [SMILES: *=C1CCCc2cc(OC)c(OC)cc21] | 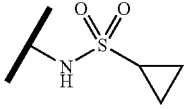 |
| (159) | 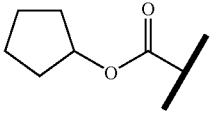 | 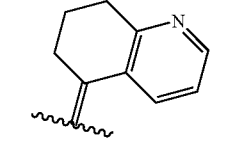 [SMILES: *=C1CCCc2ncccc21] | 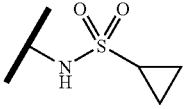 |
| (160) | 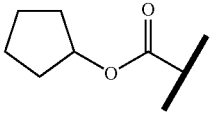 | 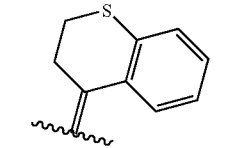 [SMILES: *=C1CCSc2ccccc21] | 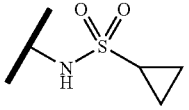 |
| (161) | 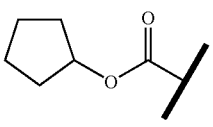 | 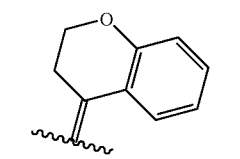 [SMILES: *=C1CCOc2ccccc21] | 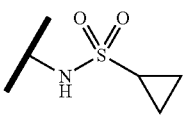 |

TABLE 3-continued

| Compound | Rx | R₁R₂ | G |
| --- | --- | --- | --- |
| (162) | cyclopentyl ester | 2,2-dimethyl-7,8-dimethoxy-chromen-4-ylidene | cyclopropanesulfonamide |
| (163) | cyclopentyl ester | 5,6-dihydroquinolin-8(7H)-ylidene | cyclopropanesulfonamide |
| (164) | cyclopentyl ester | 7-(thiophen-2-yl)-3,4-dihydronaphthalen-1(2H)-ylidene | cyclopropanesulfonamide |
| (165) | cyclobutyl ester | 5H-cyclopenta[2,1-b:3,4-b']dipyridin-5-ylidene | cyclopropanesulfonamide |
| (166) | cyclobutyl ester | 10-methylacridin-9(10H)-ylidene | cyclopropanesulfonamide |
| (167) | cyclobutyl ester | 10-oxoanthracen-9(10H)-ylidene | cyclopropanesulfonamide |
| (168) | cyclobutyl ester | 10,11-dihydro-5H-dibenzo[a,d][7]annulen-5-ylidene | cyclopropanesulfonamide |
| (169) | cyclobutyl ester | 2,3-dihydro-1H-inden-1-ylidene | cyclopropanesulfonamide |

TABLE 3-continued

| Compound | Rx | R₁R₂ | G |
|---|---|---|---|
| (170) | cyclobutyl-O-C(=O)- | tetrahydronaphthalene-ylidene | -NH-S(=O)₂-cyclopropyl |
| (171) | cyclobutyl-O-C(=O)- | methoxy-tetrahydronaphthalene-ylidene | -NH-S(=O)₂-cyclopropyl |
| (172) | cyclobutyl-O-C(=O)- | dimethoxy-tetrahydronaphthalene-ylidene | -NH-S(=O)₂-cyclopropyl |
| (173) | cyclobutyl-O-C(=O)- | tetrahydroquinoline-ylidene | -NH-S(=O)₂-cyclopropyl |
| (174) | cyclobutyl-O-C(=O)- | thiochromane-ylidene | -NH-S(=O)₂-cyclopropyl |
| (175) | cyclobutyl-O-C(=O)- | chromane-ylidene | -NH-S(=O)₂-cyclopropyl |
| (176) | cyclobutyl-O-C(=O)- | 2,2-dimethyl-6,7-dimethoxy-chromane-ylidene | -NH-S(=O)₂-cyclopropyl |
| (177) | cyclobutyl-O-C(=O)- | tetrahydroquinoline-ylidene | -NH-S(=O)₂-cyclopropyl |
| (178) | cyclobutyl-O-C(=O)- | thienyl-tetrahydronaphthalene-ylidene | -NH-S(=O)₂-cyclopropyl |

TABLE 3-continued
| Compound | Rx | R₁R₂ | G |
|---|---|---|---|
| (179) | 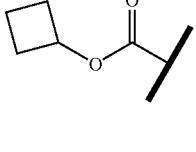 | 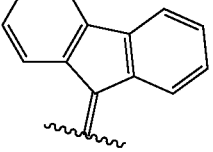 | 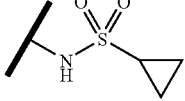 |
| (180) | 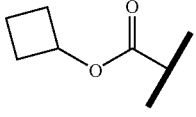 | 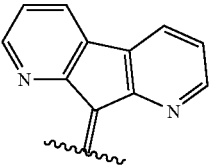 [SMILES: *=C1c2ncccc2-c2cccnc21] | 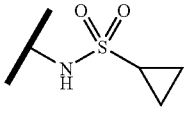 |
| (181) | 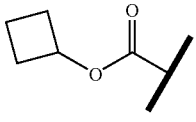 | 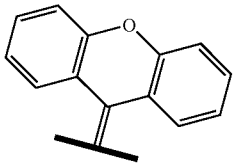 | 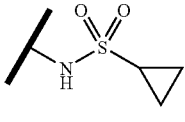 |
| (182) | 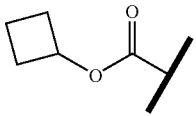 | 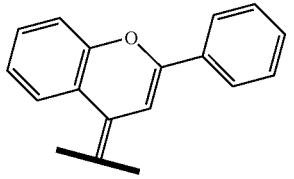 | 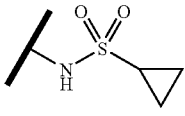 |
| (183) | 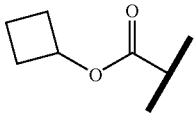 | 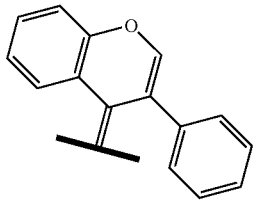 | 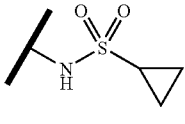 |
| (184) | 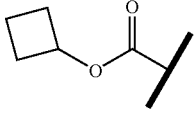 | 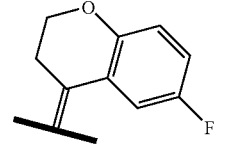 | 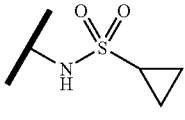 |
| (185) | 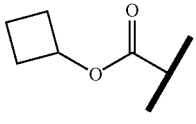 | 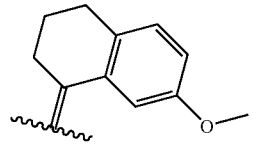 [SMILES: *=C1CCCc2ccc(OC)cc21] | 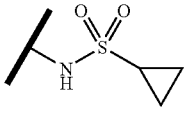 |
| (186) | 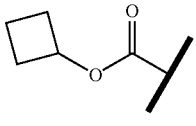 | 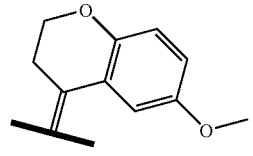 | 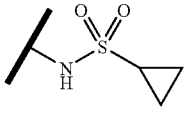 |
| (187) | 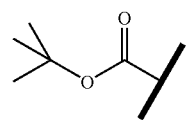 | 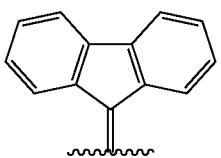 [SMILES: *=C1c2ccccc2-c2ccccc21] | 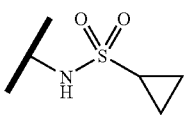 |

TABLE 3-continued

| Compound | Rx | R₁R₂ | G |
|---|---|---|---|
| (188) | | | |
| (189) | | | |
| (190) | | | |
| (191) | | | |
| (192) | | | |
| (193) | | | |
| (194) | | | |
| (195) | | | |

TABLE 3-continued
| Compound | Rx | R₁R₂ | G |
|---|---|---|---|
| (196) | 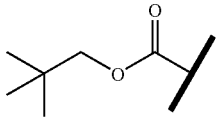 | 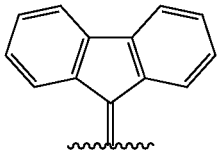 | 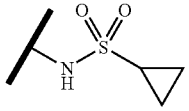 |
| (197) | 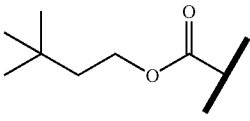 | 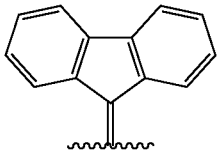 [SMILES: *=C1c2ccccc2-c2ccccc21] | 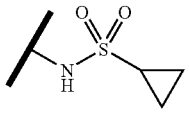 |
| (198) | 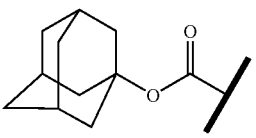 | 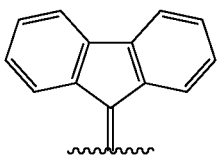 [SMILES: *=C1c2ccccc2-c2ccccc21] | 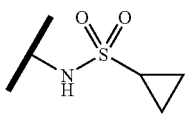 |
| (199) | 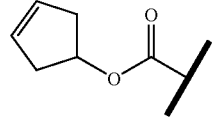 | 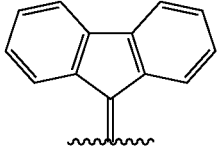 [SMILES: *=C1c2ccccc2-c2ccccc21] | 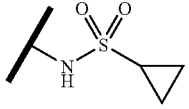 |
| (200) | 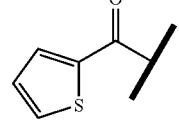 | 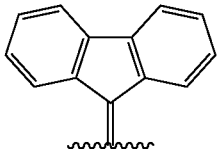 [SMILES: *=C1c2ccccc2-c2ccccc21] | 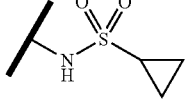 |
| (201) | 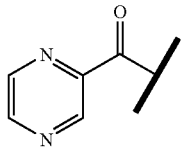 | 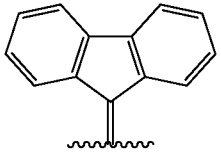 [SMILES: *=C1c2ccccc2-c2ccccc21] | 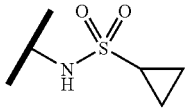 |
| (202) | 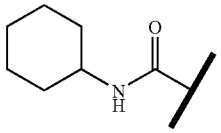 | 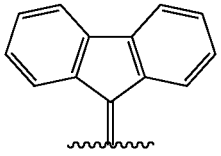 [SMILES: *=C1c2ccccc2-c2ccccc21] | 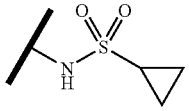 |
| (203) | 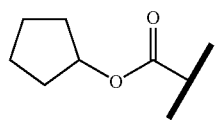 | 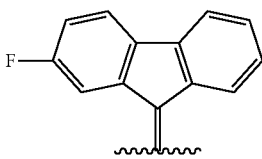 | 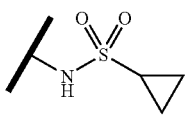 |
| (204) | 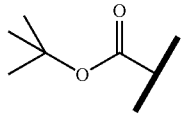 | 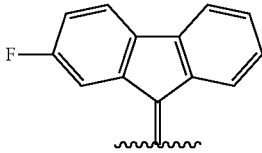 | 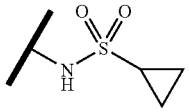 |

Further representative species of the present invention are:

Compounds (205)-(208) of the Formula D:

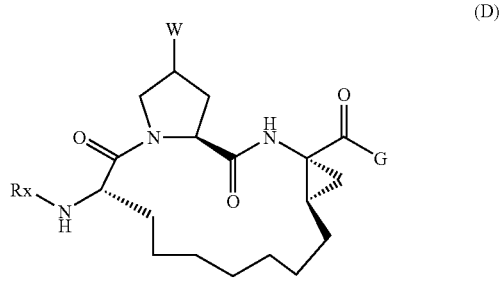

W, Rx and G are delineated for each example in TABLE 4:

TABLE 4

| Compound | Rx | W | G |
|---|---|---|---|
| (205) | tert-butyl ester group | fluorenyl | N-cyclopropylsulfonyl amide |
| (206) | cyclopentyl ester group | fluorenyl | N-cyclopropylsulfonyl amide |
| (207) | tert-butyl ester group | difluorofluorenyl | N-cyclopropylsulfonyl amide |
| (208) | cyclopentyl ester group | difluorofluorenyl | N-cyclopropylsulfonyl amide |

In one embodiment, the present invention features pharmaceutical compositions comprising a compound of the present invention, or a pharmaceutically acceptable salt, ester or prodrug thereof.

A further embodiment of the present invention includes pharmaceutical compositions comprising a compound of the present invention, or a pharmaceutically acceptable salt, ester, or prodrug thereof, with a pharmaceutically acceptable carrier or excipient.

Yet another embodiment of the present invention is a pharmaceutical composition comprising a combination of two or more compounds of the present invention, or a pharmaceutically acceptable salt, ester, or prodrug thereof, with a pharmaceutically acceptable carrier or excipient.

In another embodiment, the pharmaceutical compositions of the present invention may further contain other anti-HCV agents. Examples of anti-HCV agents include, but are not limited to, .alpha.-interferon, .beta.-interferon, ribavirin, and amantadine.

In another embodiment, the pharmaceutical compositions of the present invention may further contain other HCV protease inhibitors.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to another embodiment, the present invention includes methods of treating hepatitis C infections in a subject in need of such treatment by administering to said subject a therapeutically effective amount of the pharmaceutical compounds or compositions of the present invention. The methods can further include administration of an additional therapeutic agent, including another antiviral agent or an anti-HCV agent. The additional agent can be co-administered, concurrently administered or sequentially administered with a compound (a pharmaceutically acceptable salt, ester or prodrug thereof) or a pharmaceutical composition of the present invention. The methods herein can further include the step of identifying that the subject is in need of treatment for hepatitis C infection. The identification can be by subjective (e.g., health care provider determination) or objective (e.g., diagnostic test) means.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system having one or more aromatic rings, fused or non-fused, including, but not limited to, phenyl, naphthyl, tetrahydronaphthyl, indanyl, idenyl and the like.

The term "heteroaryl," as used herein, refers to a mono- or polycyclic (e.g. bi-, or tri-cyclic or more), fused or non-fused, aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "$C_1$-$C_8$ alkyl," or "$C_1$-$C_{12}$ alkyl," as used herein, refer to saturated, straight- or branched-chain hydrocarbon radicals containing from one to eight, or from one to twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, methyl, ethyl, propyl, isopropyl, n-butyl, tert-butyl, neopentyl, n-hexyl, heptyl, octyl, decyl, dodecyl radicals.

The term "$C_2$-$C_8$ alkenyl," as used herein, denotes a monovalent group derived from a hydrocarbon moiety containing from two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl and the like.

The term "$C_2$-$C_8$ alkynyl," as used herein, denotes a monovalent group derived from a hydrocarbon moiety containing from two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom wherein said carbocyclic ring contains from 3 to 8, or from 3 to 12, carbon atoms, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound by the removal of a single hydrogen atom wherein said carbocyclic ring contains from 3 to 8, or from 3 to 12, carbon atoms, respectively, and has at least one carbon-carbon double bond. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The terms "substituted" refer to independent replacement of one, two, or three or more of the hydrogen atoms thereon with substituents including, but not limited to, —F, —Cl, —Br, —I, —OH, protected hydroxy, —NO$_2$, —CN, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)— heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$— heteroaryl, —NHCO$_2$— heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can be replaced with an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be divalent or trivalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The terms "halo" and "halogen," as used herein, refers to an atom selected from fluorine, chlorine, bromine and iodine.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —NH(C$_1$-C$_{12}$ alkyl) where C$_1$-C$_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al, Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately, by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters.

Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, viral infections are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

An additional method of the present invention is the treatment of biological samples with an inhibitory amount of a compound of the present invention in such amounts and for such time as is necessary to inhibit viral replication and/or reduce viral load. The term "inhibitory amount" means a sufficient amount to inhibit viral replication and/or decrease the hepatitis C viral load in a biological sample. The term "biological sample(s)" as used herein means a substance of biological origin intended for administration to a subject. Examples of biological samples include, but are not limited to blood and components thereof such as plasma, platelets, subpopulations of blood cells and the like; organs such as kidney, liver, heart, lung, and the like; sperm and ova; bone marrow and components thereof, or stem cells. Thus another embodiment of the present invention is a method of treating a biological sample by contacting said biological sample with an inhibitory amount of a compound or pharmaceutical composition of the present invention.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which may appear in the following synthetic schemes and examples are:

Ac for acetyl;
Boc for tert-butoxycarbonyl;
Bz for benzoyl;
Bn for benzyl;
CDI for carbonyldiimidazole;
dba for dibenzylidene acetone;
DBU for 1,8-diazabicyclo[5.4.0]undec-7-ene;
DIAD for diisopropylazodicarboxylate;
DMAP for dimethylaminopyridine;
DMF for dimethyl formamide;
DMSO for dimethyl sulfoxide;
dppb for diphenylphosphino butane;
EtOAc for ethyl acetate;
HATU for 2-(7-Aza-1H-benzotriazole-1-yl)-1,1,3,3-tetramethyluronium hexafluorophosphate;
iPrOH for isopropanol;
NaHMDS for sodium bis(trimethylsilyl)amide;
NMO for N-methylmorpho line N-oxide;
MeOH for methanol;
Ph for phenyl;
POPd for dihydrogen dichlorobis(di-tert-butylphosphino) palladium(II);
TBAHS for tetrabutyl ammonium hydrogen sulfate;
TEA for triethylamine;
THF for tetrahydrofuran;
TPP for triphenylphosphine;
Tris for Tris(hydroxymethyl)aminomethane;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino) azobenzene)-aminohexyl-1-O-(2-cyanoethyl)-(N,N-diisopropyl)-phosphoramidite;
DCM for dichloromethane;
DIBAL-H for diisobutylaluminum hydride;
DIEA for diisopropyl ethylamine;
DME for ethylene glycol dimethyl ether;
DMEM for Dulbecco's Modified Eagles Media;
EDANS for 5-(2-Amino-ethylamino)-naphthalene-1-sulfonic acid;
EDCl or EDC for 1-(3-diethylaminopropyl)-3-ethylcarbodiimide hydrochloride;
Hoveyda's Cat. for Dichloro(o-isopropoxyphenylmethylene) (tricyclohexylphosphine)ruthenium(II);
KHMDS is potassium bis(trimethylsilyl) amide;
Ms for mesyl;
NMM for N-4-methylmorpholine;
PyBrOP for Bromo-tri-pyrolidino-phosphonium hexafluorophosphate;
RCM for ring-closing metathesis;
RT for reverse transcription;
RT-PCR for reverse transcription-polymerase chain reaction;
TEA for triethyl amine;
TFA for trifluoroacetic acid;
THF for tetrahydrofuran; and
TLC for thin layer chromatography.

Synthetic Methods

The compounds and processes of the present invention will be better understood in connection with the following synthetic schemes that illustrate the methods by which the compounds of the invention may be prepared.

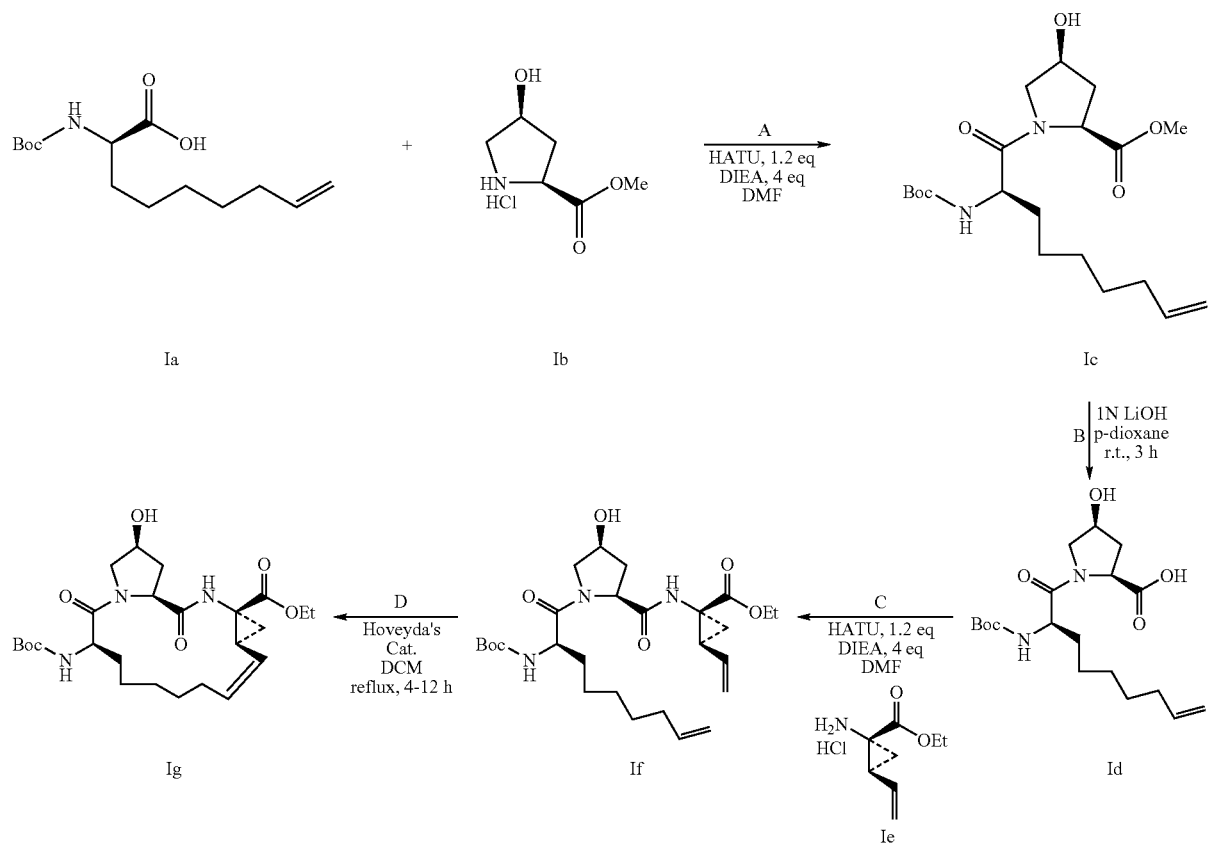

Scheme 1 describes the synthesis of intermediate Ig. The cyclic peptide precursor Ig was synthesized from Boc-L-2-amino-8-nonenoic acid Ia and cis-L-hydroxyproline methyl ester Ib via steps A-D set forth generally in Scheme 1. For further details of the synthetic methods employed to produce the cyclic peptide precursor Ig, see U.S. Pat. No. 6,608,027, which is herein incorporated by reference in its entirety. Other amino acid derivatives containing a terminal alkene may be used in place of Ia in order to create varied macrocyclic structures (for further details see WO/0059929). Ring closure methathesis with a Ruthenium-based catalyst gave the desired key intermediate Ig (for further details on ring closing metathesis see recent reviews: Grubbs et al., Acc. Chem. Res., 1995, 28, 446; Shrock et al., Tetrahedron 1999, 55, 8141; Furstner, A. Angew. Chem. Int. Ed. 2000, 39, 3012; Tmka et al., Acc. Chem. Res. 2001, 34, 18; and Hoveyda et al., Chem. Eur. J. 2001, 7, 945).

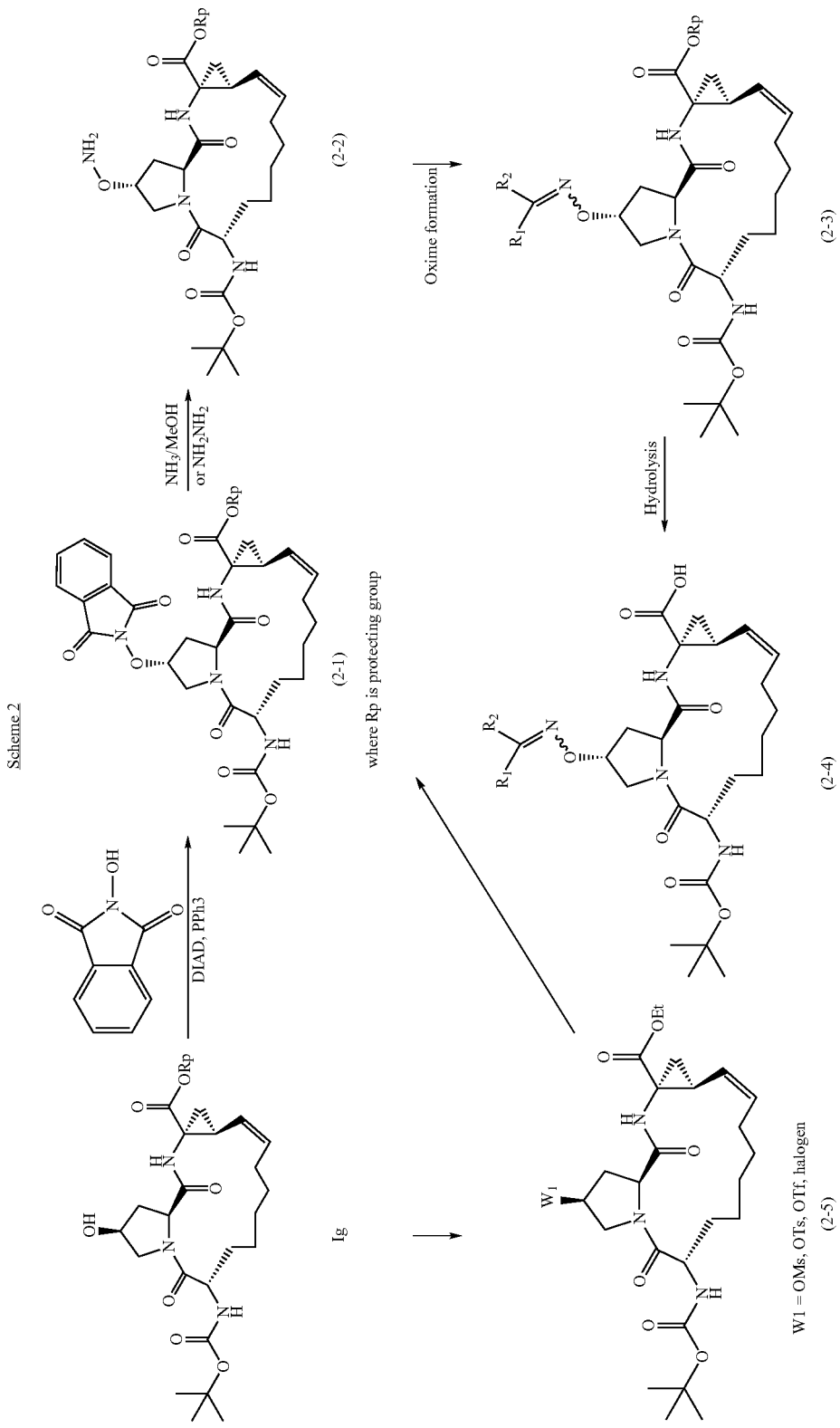

The analogs of the present invention were prepared via several different synthetic routes. The simplest method, shown in Scheme 2, is to condense commercially available hydroxyphthalimide using Mitsunobu conditions followed by deprotection of the phthalimide moiety with ammonia or hydrazine to provide hydroxy amine (2-2). For further details on the Mitsunobu reaction, see O. Mitsunobu, Synthesis 1981, 1-28; D. L. Hughes, Org. React. 29, 1-162 (1983); D. L. Hughes, Organic Preparations and Procedures Int. 28, 127-164 (1996); and J. A. Dodge, S. A. Jones, Recent Res. Dev. Org. Chem. 1, 273-283 (1997). Alternatively, intermediate (2-2) can also be made by converting hydroxy intermediate Ig to a suitable leaving group such as, but not limited to OMs, OTs, OTf, bromide, or iodide; followed with the deprotection of the phthalimide moiety with ammonia or hydrazine. Oximes (2-3) can be prepared by treating hydroxy amine with appropriate aldehyde or ketone optionally in the presence of an acid. Subsequent removal of the acid protecting group furnishes compounds of formula (2-4). A thorough discussion of solvents and conditions for protecting the acid group can be found in T. W. Greene and P. G. M. Wuts, *Protective Groups in Organic Synthesis*, 3$^{rd}$ ed., John Wiley & Son, Inc, 1999.

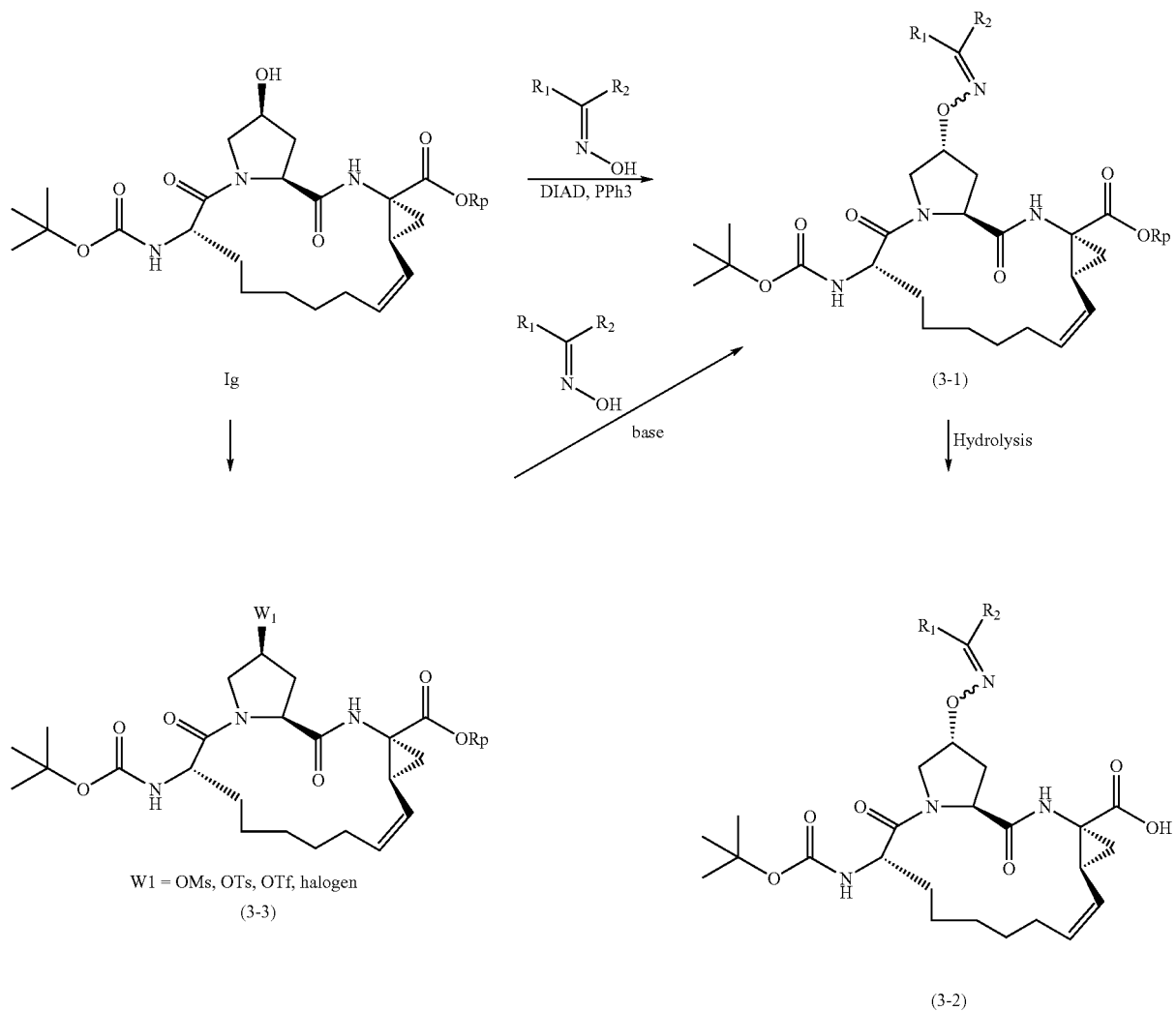

Scheme 3 where Rp is protecting group

The Scheme 3 describes the alternative methods to synthesize formula (3-2). The intermediates (3-1) can be made directly through Ig and oximes using Mitsunobu conditions. Or, intermediate (3-1) can also be made through SN2 replacement of activated hydroxyl group by converting hydroxy intermediate Ig to a suitable leaving group such as, but not limited to OMs, OTs, OTf, bromide, or iodide. Subsequent removal of the acid protecting group furnishes compounds of formula (3-2).

Scheme 4

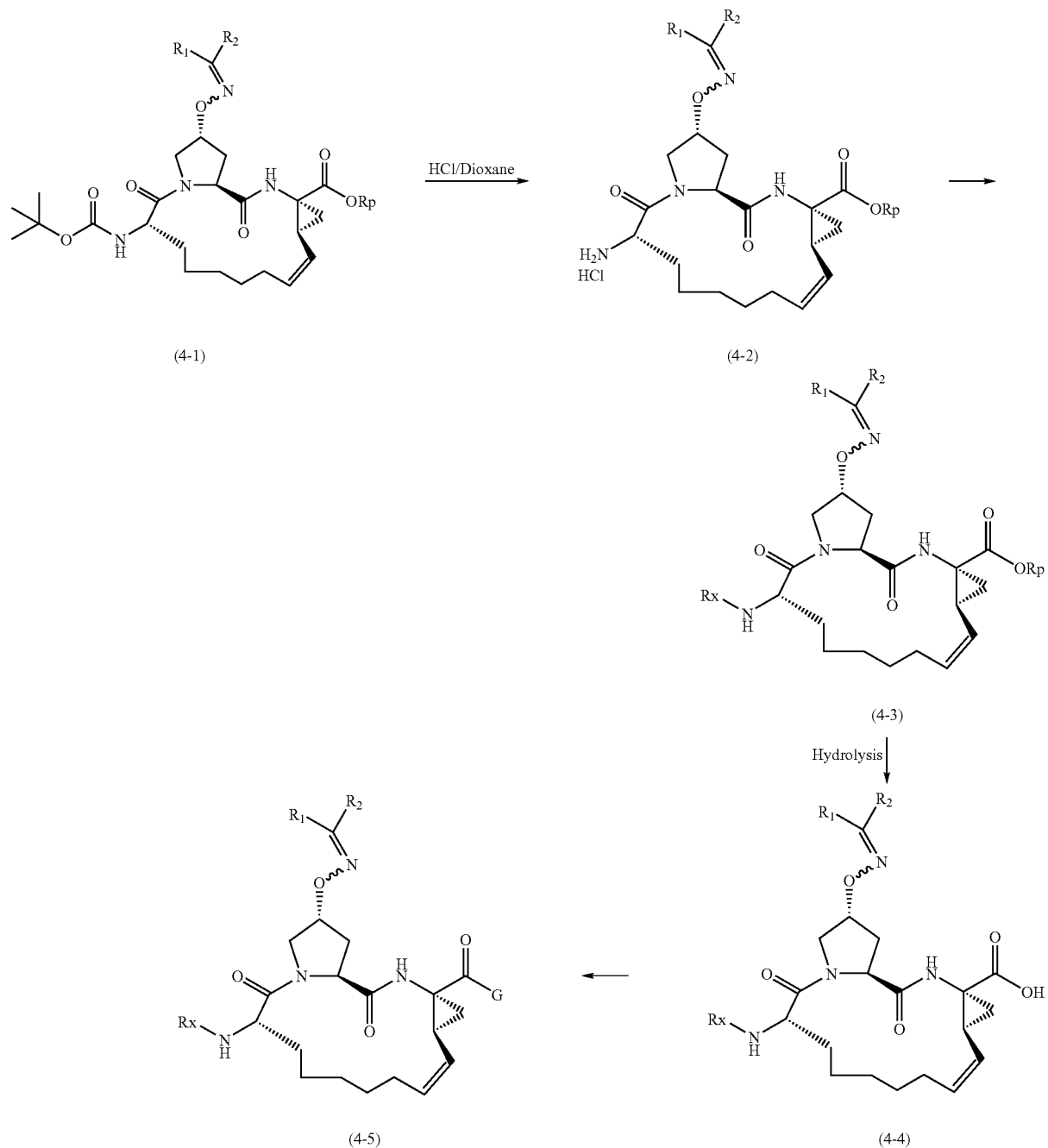

Scheme 4 illustrates the modification of the N-terminal and C-terminal of the macrocycle. Deprotection of the Boc moiety with an acid, such as, but not limited to hydrochloric acid yields compounds of formula (4-2). The amino moiety of formula (4-2) can be alkylated or acylated with appropriate alkyl halide or acyl groups to give compounds of formula (4-3). Compounds of formula (4-3) can be hydrolyzed with base such as lithium hydroxide to free up the acid moiety of formula (4-4). Subsequent activation of the acid moiety followed by treatment with appropriate acyl or sulfonyl groups to provide compounds of formula (4-5).

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

Compound of Formula A, Wherein Rx=Boc and G=OEt

Step 1a.

To a solution of Boc-L-2-amino-8-nonenoic acid (1.36 g, 5 mol) and the commercially available cis-L-hydroxyproline methyl ester (1.09 g, 6 mmol) in 15 ml DMF, was added DIEA (4 ml, 4 eq.) and HATU (4 g, 2 eq). The coupling was carried out at 0° C. over a period of 1 hour. The reaction mixture was diluted with 100 mL EtOAc, and followed by washing with 5% citric acid 2×20 ml, water 2×20 ml, 1M NaHCO$_3$ 4×20 ml and brine 2×10 ml, respectively. The organic phase was dried over anhydrous Na$_2$SO$_4$ and then was evaporated, affording the desired dipeptide (1.91 g, 95.8%) that was identified by HPLC (Retention time=8.9 min, 30-70%, 90% B), and MS.

MS (ESI): m/z=421.37 [M+Na].

Step 1b.

The dipeptide from step 1a (1.91 g) was dissolved in 15 mL of dioxane and 15 mL of 1 N LiOH aqueous solution and the hydrolysis reaction was carried out at RT for 4 hours. The reaction mixture was acidified by 5% citric acid and extracted with 100 mL EtOAc, and followed by washing with water 2×20 ml, and brine 2×20 ml, respectively. The organic phase was dried over anhydrous Na$_2$SO$_4$ and then removed in vacuum, yielding the free carboxylic acid compound (1.79 g, 97%), which was used for next step synthesis without need for further purification.

Step 1c.

To a solution of the free acid obtained from step 1b (1.77, 4.64 mmol) in 5 ml DMF, D-β-vinyl cyclopropane amino acid ethyl ester 1e (0.95 g, 5 mmol), DIEA (4 ml, 4 eq.) and HATU (4 g, 2 eq) were added. The coupling was carried out at 0° C. over a period of 5 hours. The reaction mixture was diluted with 80 mL EtOAc, and followed by washing with 5% citric acid 2×20 ml, water 2×20 ml, 1M NaHCO$_3$ 4×20 ml and brine 2×10 ml, respectively. The organic phase was dried over anhydrous Na$_2$SO$_4$ and then evaporated. The residue was purified by silica gel flash chromatography using different ratios of hexanes:EtOAc as elution phase (5:1→3:1→1:1→1:2→1:5). The desired linear tripeptide was isolated as an oil after removal of the elution solvents (1.59 g, 65.4%).

MS (ESI): m/z=544.84 [M+Na].

Step 1d.

A solution of the linear tripeptide from step 1c (1.51 g, 2.89 mmol) in 200 ml dry DCM was deoxygenated by bubbling N$_2$. Hoveyda's 1$^{st}$ generation catalyst (5 mol % eq.) was then added as solid. The reaction was refluxed under N$_2$ atmosphere 12 hours. The solvent was evaporated and the residue was purified by silica gel flash chromatography using different ratios of hexanes:EtOAc as elution phase (9:1→5:1→3:1→1:1→1:2→1:5). The cyclic peptide precursor 1 was isolated as a white powder after removal of the elution solvents (1.24 g, 87%). For further details of the synthetic methods employed to produce the cyclic peptide precursor 1, see U.S. Pat. No. 6,608,027, which is herein incorporated by reference in its entirety.

MS (ESI): m/z=516.28 [M+Na].

Step 1e.

To a solution of the cyclic precursor from step 1d 200 mg, N-hydroxylphthalamide (80 mg) and PPh$_3$ (163 mg) in THF was added DIAD (102 µL) at 0° C. The reaction mixture was stirred for overnight at room temperature. The mixture was then concentrated and purified by silica gel chromatography to give 325 mg of desired product.

MS (ESI): m/z=639.29 [M+H].

Step 1f.

To a solution of compound from step 1e (50 mg) in 1 ml EtOH was added NH$_2$NH$_2$ (5 eq) The reaction mixture was stirred for 30 min at room temperature. The mixture was then concentrated and extracted with DCM. The organic extracts were washed with 1M NaHCO$_3$, brine, dried over Na$_2$SO$_4$, filtered and concentrated. The residue was carried directly for the next step without further purification.

MS (ESI): m/z=509.37 [M+H].

Example 2

Compound of Formula A, Wherein Rx=Cyclopentyloxycarbonyl and G=OEt

Step 2a.

To a flask containing the compound from step 1e (1.22 mmol) was added 4N HCl/dioxane (10 ml). The resulting mixture was stirred for 1 hr at room temperature. The mixture was then concentrated. The residue was precipitated with MTBE. The precipitates was filtered and washed with MTBE to give desired product.

MS (ESI): m/z=539.14 [M+H].

Step 2b.

To a solution of the compound from step 2a (1.22 mmol) in DCM was added DIEA (2.2 ml) and cyclopentylchloroformate (3 eq) at 0° C. The mixture was stirred for 1.5 h at room temperature. The reaction mixture was extracted with EtOAc. The organic extracts were washed with NaHCO$_3$, brine, dried over Na$_2$SO$_4$, filtered and concentrated. The crude product was purified by silica gel chromatography to give 850 mg of desired product.

MS (ESI): m/z=651.21 [M+H].

Step 2c.

To a solution of compound from step 2b of Example 2 (0.41 mmol)) in EtOH was added NH$_2$NH$_2$ (80 µL)). The reaction mixture was stirred for 45 min at room temperature. The mixture was then concentrated and extracted with DCM. The organic extracts were washed with 1M NaHCO$_3$, brine, dried over Na$_2$SO$_4$, filtered and concentrated. The residue was carried directly for the next step without further purification.

MS (ESI): m/z=521.23 [M+H].

Example 3

Compound of Formula B, Wherein Rx=Cyclopentyloxycarbonyl, R$_1$=Methyl, R$_2$=Phenyl and G=OH Step 3a.

The mixture of compound from step 2c of Example 2 (0.05 mmol), acetophenone (0.1 mmol), HOAc (0.2 mmol)

and pyridine (0.1 mmol) in EtOH was stirred at 60° C. overnight. The reaction mixture was extracted with EtOAc. The organic extracts were washed with 1M NaHCO3, brine, dried over $Na_2SO_4$, filtered and concentrated. The residue was purified by silica gel chromatography to give desired product.

Step 3b.

To a solution of the compound from step 3a in THF/MeOH was added 1N LiOH. The reaction mixture was stirred overnight at room temperature. After acidified with 1N HCl, the resulting mixture was extracted with EtOAc. The organic extracts were washed with water and concentrated. The residue was purified by preparative HPLC to give desired product.

MS (ESI): m/z=595.24 [M+H].

Example 4

Compound of Formula B, Wherein Rx=Cyclopentyloxycarbonyl, $R_1$=Ethyl, $R_2$=Phenyl and G=OH Step 4a.

The title compound was prepared with compound from step 2c of Example 2 and propiophenone via the similar conditions described in step 3a of Example-3.

MS (ESI): m/z=637.27 [M+H].

Step 4b.

The title compound was prepared with compound from step 4a via the similar conditions described in step 3b of Example 3.

MS (ESI): m/z=609.26 [M+H].

Example 5

Compound of Formula B, Wherein Rx=Cyclopentyloxycarbonyl, $R_1$=Propyl, Rz=Phenyl and G=OH Step 5a.

The title compound was prepared with compound from step 2c of Example 2 and n-Butylphenone via the similar conditions described in step 3a of Example-3.

MS (ESI): m/z=651.36 [M+H].

Step 5b.

The title compound was prepared with compound from step 5a via the similar conditions described in step 3b of Example 3.

MS (ESI): m/z=623.32 [M+H].

Example 6

Compound of Formula B, Wherein Rx=Cyclopentyloxycarbonyl, $R_1$=$CH_3OCH_2$, $R_2$=Phenyl and G=OH Step 6a.

The title compound was prepared with compound from step 2c of Example 2 and 2-Methoxy-acetophenone via the similar conditions described in step 3a of Example-3.

MS (ESI): m/z=653.33[M+H].

Step 6b.

The title compound was prepared with compound from step 6a via the similar conditions described in step 3b of Example 3.

MS (ESI): m/z=625.24 [M+H].

Example 7

Compound of Formula B, Wherein Rx=Cyclopentyloxycarbonyl, $R_1$=Phenyl, $R_2$=Phenyl and G=OH Step 7a.

The title compound was prepared with compound from step 2c of Example 2 and benzophenone via the similar conditions described in step 3a of Example 3.

MS (ESI): m/z=685.20 [M+H].

Step 7b.

The title compound was prepared with compound from step 7a via the similar conditions described in step 3b of Example 3.

MS (ESI): m/z=657.24 [M+H].

Example 8

Compound of Formula B, Wherein Rx=Cyclopentyloxycarbonyl, $R_1$=Thiophen-2-yl, $R_2$=Phenyl and G=OH Step 8a.

The title compound was prepared with compound from step 2c of Example 2 and 2-Benzoylthiophene via the similar conditions described in step 3a of Example-3.

MS (ESI): m/z=691.16 [M+H].

Step 8b.

The title compound was prepared with compound from step 8a via the similar conditions described in step 3b of Example 3.

MS (ESI): m/z=663.19 [M+H].

Example 9

Compound of Formula B, Wherein Rx=Cyclopentyloxycarbonyl, $R_1$=Isopropyl, $R_2$=Phenyl and G=OH Step 9a.

The title compound was prepared with compound from step 2c of Example 2 and isobutyrophenone via the similar conditions described in step 3a of Example 3.

MS (ESI): m/z=651.32 [M+H].

Step 9b.

The title compound was prepared with compound from step 9a via the similar conditions described in step 3b of Example 3.

MS (ESI): m/z=623.25 [M+H].

Example 10

Compound of Formula B, Wherein Rx=Cyclopentyloxycarbonyl, $R_1$=2-Methyl-Propan-1-yl, $R_2$=Phenyl and G=OH Step 10a.

The title compound was prepared with compound from step 2c of Example 2 and isovalerophenone via the similar conditions described in step 3a of Example 3.

MS (ESI): m/z=665.34 [M+H].

Step 10b.
The title compound was prepared with compound from step 10a via the similar conditions described in step 3b of Example 3.
MS (ESI): m/z=637.27 [M+H].

Example 11

Compound of Formula B, Wherein Rx=Cyclopentyloxycarbonyl, $R_1$=Cyclopentyl, $R_2$=Phenyl and G=OH Step 11a.
The title compound was prepared with compound from step 2c of Example 2 and Cyclopentyl phenyl ketone via the similar conditions described in step 3a of Example-3.
MS (ESI): m/z=677.32 [M+H].
Step 11b.
The title compound was prepared with compound from step 11a via the similar conditions described in step 3b of Example 3.
MS (ESI): m/z=649.28 [M+H].

Example 12

Compound of Formula B, Wherein Rx=Cyclopentyloxycarbonyl, $R_1$=Cyclohexyl, $R_2$=Phenyl and G=OH Step 12a.
The title compound was prepared with compound from step 2c of Example 2 and Cyclohexyl phenyl ketone via the similar conditions described in step 3a of Example-3.
MS (ESI): m/z=691.38 [M+H].
Step 12b.
The title compound was prepared with compound from step 12a via the similar conditions described in step 3b of Example 3.
MS (ESI): m/z=663.28 [M+H].

Example 13

Compound of Formula B, Wherein Rx=Cyclopentyloxycarbonyl, $R_1$=H, $R_2$=Phenyl and G=OH Step 13a.
The title compound was prepared with compound from step 2c of Example 2 and benzaldehyde via the similar conditions described in step 3a of Example 3.
MS (ESI): m/z=609 [M+H].
Step 13b.
The title compound was prepared with compound from step 13a via the similar conditions described in step 3b of Example 3.
MS (ESI): m/z=581.31 [M+H].

Example 14

Compound of Formula B, Wherein Rx=Cyclopentyloxycarbonyl, $R_1$=H, $R_2$=Biphenyl-2-yl and G=OH Step 14a.
The title compound was prepared with compound from step 2c of Example 2 and Biphenyl-2-carboxaldehyde via the similar conditions described in step 3a of Example 3.

Step 14b.
The title compound was prepared with compound from step 14a via the similar conditions described in step 3b of Example 3.
MS (ESI): m/z=657.24 [M+H].

Example 15

Compound of Formula B, Wherein Rx=Cyclopentyloxycarbonyl, $R_1$=H, $R_2$=Biphenyl-3-yl and G=OH Step 15a.
The title compound was prepared with compound from step 2c of Example 2 and Biphenyl-3-carboxaldehyde via the similar conditions described in step 3a of Example 3.
Step 15b.
The title compound was prepared with compound from step 15a via the similar conditions described in step 3b of Example 3.
MS (ESI): m/z=657.30 [M+H].

Example 16

Compound of Formula B, Wherein Rx=Cyclopentyloxycarbonyl, $R_1$=H, $R_2$=Biphenyl-4-yl and G=OH Step 16a.
The title compound was prepared with compound from step 2c of Example 2 and Biphenyl-4-carboxaldehyde via the similar conditions described in step 3a of Example 3.
Step 16b.
The title compound was prepared with compound from step 16a via the similar conditions described in step 3b of Example 3.
MS (ESI): m/z=657.24 [M+H].

Example 17

Compound of Formula B, Wherein Rx=Cyclopentyloxycarbonyl, $R_1$=H, $R_2$=Naphthalen-1-yl and G=OH Step 17a.
The title compound was prepared with compound from step 2c of Example 2 and Naphthalene-1-carboxaldehyde via the similar conditions described in step 3a of Example 3.
MS (ESI): m/z=659.21 [M+H].
Step 17b.
The title compound was prepared with compound from step 17a via the similar conditions described in step 3b of Example 3.
MS (ESI): m/z=631.26 [M+H].

Example 18

Compound of Formula B, Wherein Rx=Cyclopentyloxycarbonyl, $R_1$=H, $R_2$=Naphthalen-2-yl and G=OH Step 18a.
The title compound was prepared with compound from step 2c of Example 2 and Naphthalene-2-carboxaldehyde via the similar conditions described in step 3a of Example 3.
MS (ESI): m/z=659.21 [M+H].

Step 18b.
The title compound was prepared with compound from step 18a via the similar conditions described in step 3b of Example 3.
MS (ESI): m/z=631.26 [M+H].

Example 19

Compound of Formula B, Wherein Rx=Cyclopentyloxycarbonyl, $R_1$=Ethyl $R_2$=Biphenyl-2-yl and G=OH Step 19a.
The title compound was prepared with compound from step 2c of Example 2 and 1-Biphenyl-2-yl-propan-3-one via the similar conditions described in step 3a of Example 3.
MS (ESI): m/z=713 [M+H].
Step 19b.
The title compound was prepared with compound from step 19a via the similar conditions described in step 3b of Example 3.
MS (ESI): m/z=685.21 [M+H].

Example 20

Compound of Formula B, Wherein Rx=Cyclopentyloxycarbonyl, $R_1$=H, $R_2$=Pyridin-2-yl and G=OH Step 20a.
The title compound was prepared with compound from step 2c of Example 2 and Pyridine-2-carboxaldehyde via the similar conditions described in step 3a of Example 3.
Step 20b.
The title compound was prepared with compound from step 20a via the similar conditions described in step 3b of Example 3.
MS (ESI): m/z=582.23 [M+H].

Example 21

Compound of Formula B, Wherein Rx=Cyclopentyloxycarbonyl, $R_1$=H, $R_2$=Pyridin-3-yl and G=OH Step 21a.
The title compound was prepared with compound from step 2c of Example 2 and Pyridine-3-carboxaldehyde via the similar conditions described in step 3a of Example 3.
Step 21b.
The title compound was prepared with compound from step 21a via the similar conditions described in step 3b of Example 3.
MS (ESI): m/z=582.23 [M+H].

Example 22

Compound of Formula B, Wherein Rx=Cyclopentyloxycarbonyl, $R_1$=H, $R_2$=Pyridin-4-yl and G=OH Step 22a.
The title compound was prepared with compound from step 2c of Example 2 and Pyridine-4-carboxaldehyde via the similar conditions described in step 3a of Example 3.

Step 22b.
The title compound was prepared with compound from step 22a via the similar conditions described in step 3b of Example 3.
MS (ESI): m/z=582.24 [M+H].

Example 23

Compound of Formula B, Wherein Rx=Cyclopentyloxycarbonyl, $R_1$=H, $R_2$=Quinolin-4-yl and G=OH Step 23a.
The title compound was prepared with compound from step 2c of Example 2 and Quinoline-4-carboxaldehyde via the similar conditions described in step 3a of Example 3.
Step 23b.
The title compound was prepared with compound from step 23a via the similar conditions described in step 3b of Example 3.
MS (ESI): m/z=632.22 [M+H].

Example 24

Compound of Formula B, Wherein Rx=Cyclopentyloxycarbonyl, $R_1$=H, $R_2$=Quinolin-3-yl and G=OH Step 24a.
The title compound was prepared with compound from step 2c of Example 2 and Quinoline-3-carboxaldehyde via the similar conditions described in step 3a of Example 3.
MS (ESI): m/z=660.20 [M+H].
Step 24b.
The title compound was prepared with compound from step 24a via the similar conditions described in step 3b of Example 3.
MS (ESI): m/z=632.22 [M+H].

Example 25

Compound of Formula B, Wherein Rx=Cyclopentyloxycarbonyl, $R_1$=H, $R_2$=(2-Methoxy-phenyl) and G=OH Step 25a.
The title compound was prepared with compound from step 2c of Example 2 and 2-Methoxy-benzaldehyde via the similar conditions described in step 3a of Example 3.
Step 25b.
The title compound was prepared with compound from step 25a via the similar conditions described in step 3b of Example 3.
MS (ESI): m/z=611.27 [M+H].

Example 26

Compound of Formula B, Wherein Rx=Cyclopentyloxycarbonyl, $R_1$=H, $R_2$=(3-Methoxy-phenyl) and G=OH Step 26a.
The title compound was prepared with compound from step 2c of Example 2 and 3-Methoxy-benzaldehyde via the similar conditions described in step 3a of Example 3.

Step 26b.

The title compound was prepared with compound from step 26a via the similar conditions described in step 3b of Example 3.

MS (ESI): m/z=611.27 [M+H].

Example 27

Compound of Formula B, Wherein
Rx=Cyclopentyloxycarbonyl, $R_1$=H,
$R_2$=(4-Methoxy-phenyl) and G=OH Step 27a.

The title compound was prepared with compound from step 2c of Example 2 and 4-Methoxy-benzaldehyde via the similar conditions described in step 3a of Example 3.

Step 27b.

The title compound was prepared with compound from step 27a via the similar conditions described in step 3b of Example 3.

MS (ESI): m/z=611.25 [M+H].

Example 28

Compound of Formula B, Wherein
Rx=Cyclopentyloxycarbonyl, $R_1$=H,
$R_2$=(2-Fluoro-phenyl) and G=OH Step 28a.

The title compound was prepared with compound from step 2c of Example 2 and 2-Fluoro-benzaldehyde via the similar conditions described in step 3a of Example 3.

Step 28b.

The title compound was prepared with compound from step 28a via the similar conditions described in step 3b of Example 3.

MS (ESI): m/z=599.21 [M+H].

Example 29

Compound of Formula B, Wherein
Rx=Cyclopentyloxycarbonyl, $R_1$=H,
$R_2$=(3-Fluoro-phenyl) and G=OH Step 29a.

The title compound was prepared with compound from step 2c of Example 2 and 3-Fluoro-benzaldehyde via the similar conditions described in step 3a of Example-3.

Step 29b.

The title compound was prepared with compound from step 29a via the similar conditions described in step 3b of Example 3.

MS (ESI): m/z=599.27 [M+H].

Example 30

Compound of Formula B, Wherein
Rx=Cyclopentyloxycarbonyl, $R_1$=H,
$R_2$=(4-Fluoro-phenyl) and G=OH Step 30a.

The title compound was prepared with compound from step 2c of Example 2 and 4-Fluoro-benzaldehyde via the similar conditions described in step 3a of Example 3.

Step 30b.

The title compound was prepared with compound from step 30a via the similar conditions described in step 3b of Example 3.

MS (ESI): m/z=599.25 [M+H].

Example 31

Compound of Formula B, Wherein
Rx=Cyclopentyloxycarbonyl, $R_1$=H,
$R_2$=(2-Thiophen-2-yl-phenyl) and G=OH Step 31a.

The title compound was prepared with compound from step 2c of Example 2 and 2-Thiophen-2-yl-benzaldehyde via the similar conditions described in step 3a of Example 3.

MS (ESI): m/z 691.24 [M+H].

Step 31b.

The title compound was prepared with compound from step 31a via the similar conditions described in step 3b of Example 3.

MS (ESI): m/z=662.79 [M+H].

Example 32

Compound of Formula B, Wherein
Rx=Cyclopentyloxycarbonyl, $R_1$=H,
$R_2$=(2-Pyrazol-1-yl-phenyl) and G=OH Step 32a.

The title compound was prepared with compound from step 2c of Example 2 and 2-Pyrazol-1-yl-benzaldehyde via the similar conditions described in step 3a of Example 3.

MS (ESI): m/z=675.27 [M+H].

Step 32b.

The title compound was prepared with compound from step 32a via the similar conditions described in step 3b of Example 3.

MS (ESI): m/z=647.14 [M+H].

Example 33

Compound of Formula B, Wherein
Rx=Cyclopentyloxycarbonyl, $R_1$=H,
$R_2$=(2-[1,2,4]Triazol-1-yl-phenyl) and G=OH Step 33a.

The title compound was prepared with compound from step 2c of Example 2 and 2-[1,2,4]Triazol-1-yl-benzaldehyde via the similar conditions described in step 3a of Example 3.

MS (ESI): m/z=676.18 [M+H].

Step 33b.

The title compound was prepared with compound from step 33a via the similar conditions described in step 3b of Example 3.

MS (ESI): m/z=648.30 [M+H].

Example 34

Compound of Formula B, Wherein
Rx=Cyclopentyloxycarbonyl, $R_1$=H,
$R_2$=(2-Thiazol-2-yl-phenyl) and G=OH Step 34a.

The title compound was prepared with compound from step 2c of Example 2 and 2-Thiazol-2-yl-benzaldehyde via the similar conditions described in step 3a of Example 3.

MS (ESI): m/z=692.14 [M+H].

Step 34b.
The title compound was prepared with compound from step 34a via the similar conditions described in step 3b of Example 3.
MS (ESI): m/z=664.27 [M+H].

Example 35

Compound of Formula B, Wherein Rx=Cyclopentyloxycarbonyl, $R_1$=H, $R_2$=(2-Imidazol-1-yl-phenyl) and G=OH Step 35a.
The title compound was prepared with compound from step 2c of Example 2 and 2-Imidazol-1-yl-benzaldehyde via the similar conditions described in step 3a of Example 3.
MS (ESI): m/z=675.19 [M+H].
Step 35b.
The title compound was prepared with compound from step 35a via the similar conditions described in step 3b of Example 3.
MS (ESI): m/z=647.29 [M+H].

Example 36

Compound of Formula B, Wherein Rx=Cyclopentyloxycarbonyl, $R_1$=H, $R_2$=(5-Methoxy-2-thiophen-2-yl-phenyl) and G=OH Step 36a.
The title compound was prepared with compound from step 2c of Example 2 and 5-Methoxy-2-thiophen-2-yl-benzaldehyde via the similar conditions described in step 3a of Example 3.
MS (ESI): m/z=721.28 [M+H].
Step 36b.
The title compound was prepared with compound from step 36a via the similar conditions described in step 3b of Example 3.
MS (ESI): m/z=693.20 [M+H].

Example 37

Compound of Formula B, Wherein Rx=Cyclopentyloxycarbonyl, $R_1$=H, $R_2$=(5-Methoxy-2-thiazol-2-yl-phenyl) and G=OH Step 37a.
The title compound was prepared with compound from step 2c of Example 2 and 5-Methoxy-2-thiazol-2-yl-benzaldehyde via the similar conditions described in step 3a of Example 3.
MS (ESI): m/z=722.27 [M+H].
Step 37b.
The title compound was prepared with compound from step 37a via the similar conditions described in step 3b of Example 3.
MS (ESI): m/z=694.32 [M+H].

Example 38

Compound of Formula B, Wherein Rx=Cyclopentyloxycarbonyl, $R_1$=H, $R_2$=(5-Methoxy-2-thiophen-2-yl-phenyl) and G=NHSO$_2$-cyclopropyl To a solution of compound from step 36b of Example 36 in DMF was added CDI. The reaction mixture was stirred at 40° C. for 1 h and then added cyclopropylsulfonamide and DBU. The reaction mixture was stirred overnight at 40° C. The reaction mixture was extracted with EtOAc. The organic extracts were washed with 1M NaHCO$_3$, brine, dried over Na$_2$SO$_4$, filtered and concentrated. The residue was purified by silica gel chromatograph to give desired product.
MS (ESI): m/z=796.21 [M+H].

Example 39

Compound of Formula B, Wherein Rx=Cyclopentyloxycarbonyl, $R_1$=H, $R_2$=Biphenyl-2-yl and G=NHSO$_2$-cyclopropyl To a solution of compound from step 14b of Example 14 in DMF was added CDI. The reaction mixture was stirred at 40° C. for 1 h and then added cyclopropylsulfonamide and DBU. The reaction mixture was stirred overnight at 40° C. The reaction mixture was extracted with EtOAc. The organic extracts were washed with 1M NaHCO$_3$, brine, dried over Na$_2$SO$_4$, filtered and concentrated. The residue was purified by silica gel chromatograph to give desired product.
MS (ESI): m/z=760.35 [M+H].

Example 40

Compound of Formula B, Wherein Rx=Cyclopentyloxycarbonyl, $R_1$=H, $R_2$=(2-Thiophen-2-yl-phenyl) and G=NHSO$_2$-cyclopropyl To a solution of compound from step 31b of Example 31 in DMF was added CDI. The reaction mixture was stirred at 40° C. for 1 h and then added cyclopropylsulfonamide and DBU. The reaction mixture was stirred overnight at 40° C. The reaction mixture was extracted with EtOAc. The organic extracts were washed with 1M NaHCO$_3$, brine, dried over Na$_2$SO$_4$, filtered and concentrated. The residue was purified by silica gel chromatograph to give desired product.
MS (ESI): m/z=766.34 [M+H].

Example 41

Compound of Formula B, Wherein Rx=Cyclopentyloxycarbonyl, $R_1$=H, $R_2$=(2-Isoxazol-5-yl-5-methoxy-phenyl) and G=OH Step 41a.
The title compound was prepared with compound from step 2c of Example 2 and 2-Isoxazol-5-yl-5-methoxy-benzaldehyde via the similar conditions described in step 3a of Example 3.
MS (ESI): m/z=706.50 [M+H].
Step 41b.
The title compound was prepared with compound from step 41a via the similar conditions described in step 3b of Example 3.
MS (ESI): m/z=678.33 [M+H].

Example 42

Compound of Formula B, Wherein Rx=Cyclopentyloxycarbonyl, $R_1$=H, $R_2$=(2-Isoxazol-5-yl-5-methoxy-phenyl) and G=NHSO$_2$-cyclopropyl To a solution of compound from step 41b of Example 41 in DMF was added CDI. The reaction mixture was stirred at 40° C. for 1 h and then added cyclopropylsulfonamide and DBU. The reaction mixture was stirred overnight at 40° C. The reaction mixture was extracted with EtOAc. The organic extracts were washed with 1M NaHCO$_3$, brine, dried over Na$_2$SO$_4$, filtered and concentrated. The residue was purified by silica gel chromatograph to give desired product.

MS (ESI): m/z=781.22 [M+H].

Example 43

Compound of Formula B, Wherein Rx=Boc, $R_1$=Phenyl $R_2$=Phenyl and G=OH

Step 43a.

The title compound was prepared with compound from step 1f of Example 1 and benzophenone via the similar conditions described in step 3a of Example 3.

MS (ESI): m/z=673.46 [M+H].

Step 43b.

The title compound was prepared with compound from step 43a via the similar conditions described in step 3b of Example 3.

MS (ESI): m/z=645.06 [M+H].

Example 44

Compound of Formula B, Wherein Rx=Boc, $R_1$=CH, $R_2$=Phenyl and G=OH

Step 44a.

The title compound was prepared with compound from step 1f of Example 1 and acetophenone via the similar conditions described in step 3a of Example 3.

MS (ESI): m/z=611.35 [M+H].

Step 44b.

The title compound was prepared with compound from step 44a via the similar conditions described in step 3b of Example 3.

MS (ESI): m/z=583.31 [M+H].

Example 45

Compound of Formula B, Wherein Rx=Boc, $R_1$=H, $R_2$=Phenyl and G=OH

Step 45a.

The title compound was prepared with compound from step 1f of Example 1 and benzaldehyde via the similar conditions described in step 3a of Example 3.

MS (ESI): m/z=597.35 [M+H].

Step 45b.

The title compound was prepared with compound from step 45a via the similar conditions described in step 3b of Example 3.

MS (ESI): m/z=569.26 [M+H].

Example 46 to Example 115 (Formula B) are made following the procedures described in Examples 1, 3 or 38.

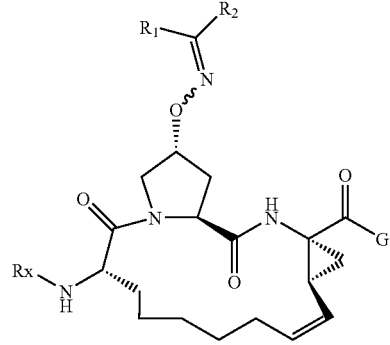

(B)

| Compound | Rx | $R_1$ | $R_2$ | G |
|---|---|---|---|---|
| (46) | cyclopentyl-O-C(O)- | —CH$_3$ | —Ph | —C(O)NHSO$_2$-cyclopropyl |
| (47) | cyclopentyl-O-C(O)- | —CH$_2$CH$_3$ | —Ph | —C(O)NHSO$_2$-cyclopropyl |
| (48) | cyclopentyl-O-C(O)- | —CH$_2$CH$_2$CH$_3$ | —Ph | —C(O)NHSO$_2$-cyclopropyl |

-continued
(B)
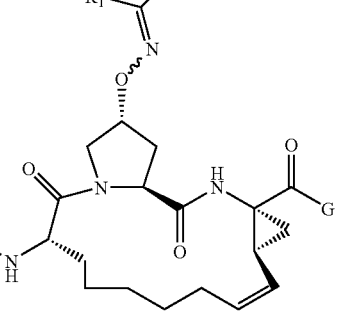
| Compound | Rx | R₁ | R₂ | G |
|---|---|---|---|---|
| (49) | 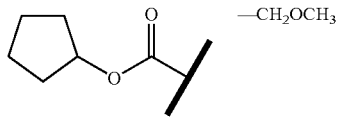 | —CH₂OCH₃ | —Ph | 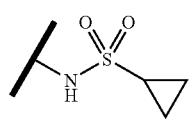 |
| (50) | 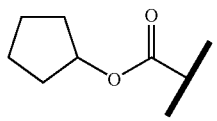 | —Ph | —Ph | 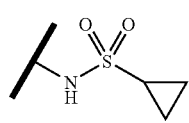 |
| (51) | 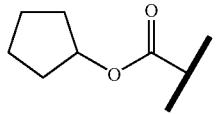 | —Ph | 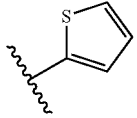 [SMILES: *c1cccs1] | 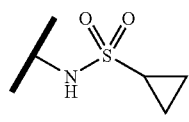 |
| (52) | 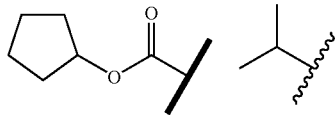 | | —Ph | 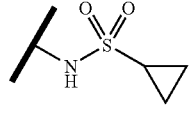 |
| (53) | 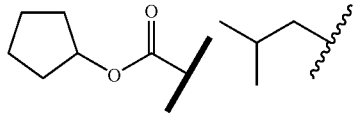 | | —Ph | 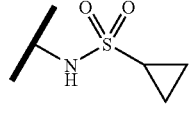 |
| (54) | 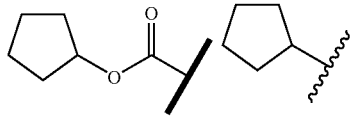 | | —Ph | 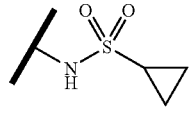 |
| (55) | 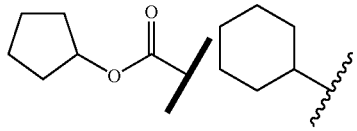 | | —Ph | 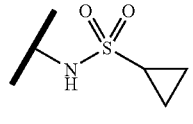 |
| (56) | 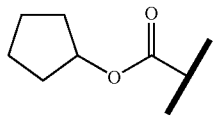 | —H | —Ph | 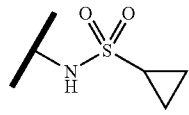 |

-continued (B)

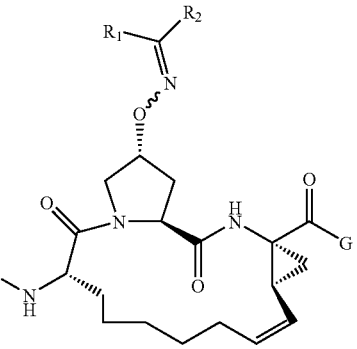

| Compound | Rx | R₁ | R₂ | G |
| --- | --- | --- | --- | --- |
| (57) | cyclopentyl ester | —H | 3-biphenyl | cyclopropylsulfonamide |
| (58) | cyclopentyl ester | —H | 4-biphenyl | cyclopropylsulfonamide |
| (59) | cyclopentyl ester | —H | 1-naphthyl | cyclopropylsulfonamide |
| (60) | cyclopentyl ester | —H | 2-naphthyl | cyclopropylsulfonamide |
| (61) | cyclopentyl ester | —CH₂CH₃ | 2-biphenyl | cyclopropylsulfonamide |
| (62) | cyclopentyl ester | —H | 2-pyridyl | cyclopropylsulfonamide |
| (63) | cyclopentyl ester | —H | 3-pyridyl | cyclopropylsulfonamide |

-continued
(B)
| Compound | Rx | R₁ | R₂ | G |
|---|---|---|---|---|
| (64) | 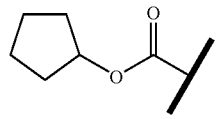 | —H | 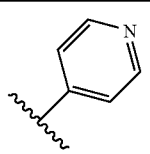 | 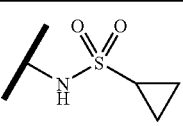 |
| (65) | 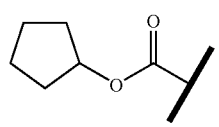 | —H | 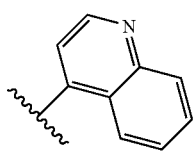 [SMILES: *c1ccnc2ccccc12] | 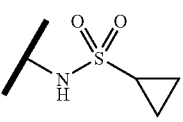 |
| (66) | 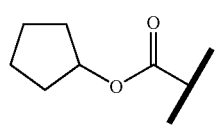 | —H | 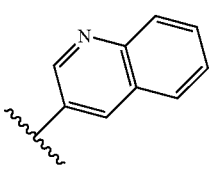 [SMILES: *c1cnc2ccccc2c1] | 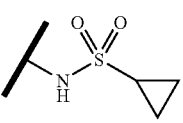 |
| (67) | 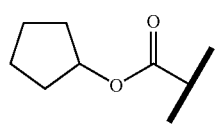 | —H | 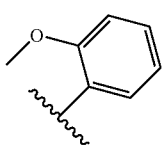 [SMILES: *c1ccccc1OC] | 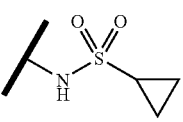 |
| (68) | 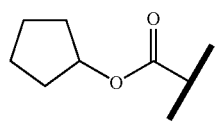 | —H | 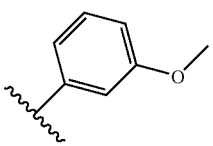 [SMILES: *c1cccc(OC)c1] | 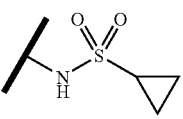 |
| (69) | 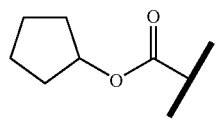 | —H | 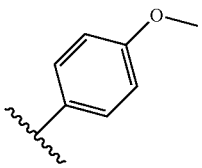 [SMILES: *c1ccc(OC)cc1] | 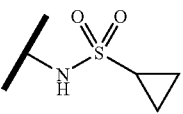 |
| (70) | 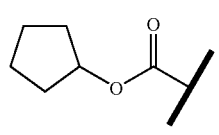 | —H | 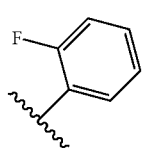 [SMILES: *c1ccccc1F] | 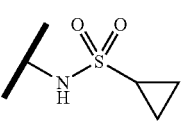 |

-continued (B)

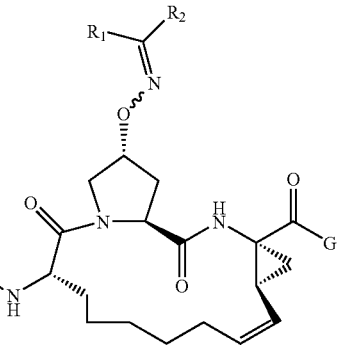

| Compound | Rx | R₁ | R₂ | G |
|---|---|---|---|---|
| (71) | cyclopentyl-O-C(=O)- | —H | 3-fluorophenyl | -NH-S(=O)₂-cyclopropyl |
| (72) | cyclopentyl-O-C(=O)- | —H | 4-fluorophenyl | -NH-S(=O)₂-cyclopropyl |
| (73) | cyclopentyl-O-C(=O)- | —H | 2-(pyrazol-1-yl)phenyl | -NH-S(=O)₂-cyclopropyl |
| (74) | cyclopentyl-O-C(=O)- | —H | 2-(1,2,4-triazol-1-yl)phenyl | -NH-S(=O)₂-cyclopropyl |
| (75) | cyclopentyl-O-C(=O)- | —H | 2-(thiazol-2-yl)phenyl | -NH-S(=O)₂-cyclopropyl |
| (76) | cyclopentyl-O-C(=O)- | —H | 2-(imidazol-1-yl)phenyl | -NH-S(=O)₂-cyclopropyl |
| (77) | cyclopentyl-O-C(=O)- | —H | 4-(thiazol-2-yl)-3-substituted phenyl-O- | -NH-S(=O)₂-cyclopropyl |

-continued

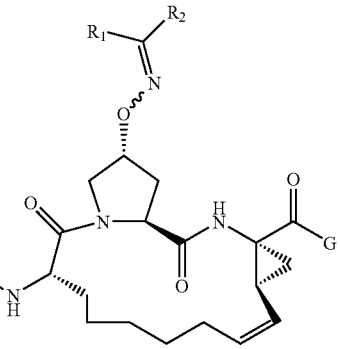

(B)

| Compound | Rx | R₁ | R₂ | G |
|---|---|---|---|---|
| (78) | cyclopentyl-O-C(O)-CH< | —Ph | —Ph | -NH-S(O)₂-cyclopropyl |
| (79) | cyclopentyl-O-C(O)-CH< | —CH₃ | —Ph | -NH-S(O)₂-cyclopropyl |
| (80) | cyclopentyl-O-C(O)-CH< | —H | —Ph | -NH-S(O)₂-cyclopropyl |
| (81) | cyclobutyl-O-C(O)-CH< | —CH₃ | —Ph | -NH-S(O)₂-cyclopropyl |
| (82) | cyclobutyl-O-C(O)-CH< | —CH₂CH₃ | —Ph | -NH-S(O)₂-cyclopropyl |
| (83) | cyclobutyl-O-C(O)-CH< | —CH₂CH₂CH₃ | —Ph | -NH-S(O)₂-cyclopropyl |
| (84) | cyclobutyl-O-C(O)-CH< | —CH₂OCH₃ | —Ph | -NH-S(O)₂-cyclopropyl |
| (85) | cyclobutyl-O-C(O)-CH< | —Ph | —Ph | -NH-S(O)₂-cyclopropyl |
| (86) | cyclobutyl-O-C(O)-CH< | —Ph | 2-thienyl | -NH-S(O)₂-cyclopropyl |

-continued
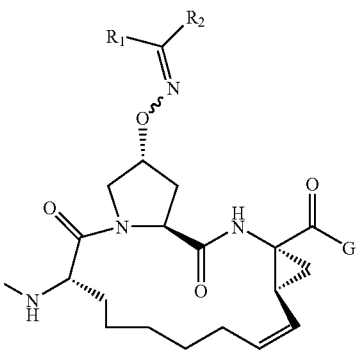
(B)
| Compound | Rx | R₁ | R₂ | G |
|---|---|---|---|---|
| (87) | 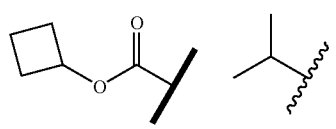 | 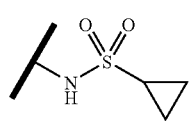 | —Ph | 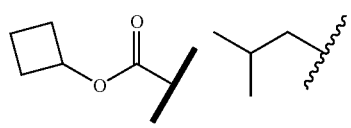 |
| (88) | 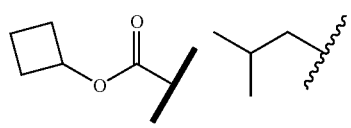 | 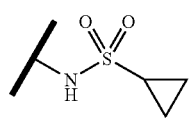 | —Ph | 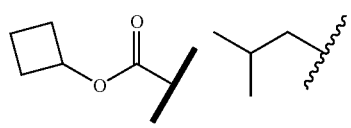 |
| (89) | 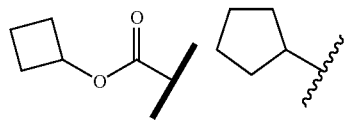 | 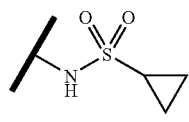 | —Ph | 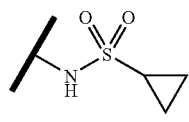 |
| (90) | 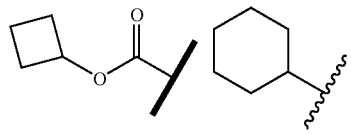 | 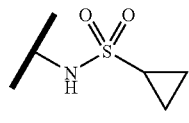 | —Ph | 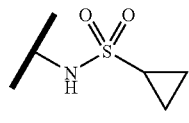 |
| (91) | 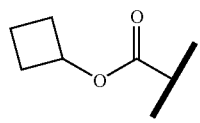 | —H | —Ph | 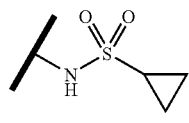 |
| (92) | 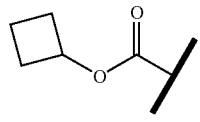 | —H | 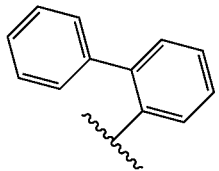 | 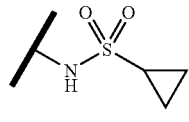 |
| (93) | 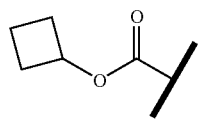 | —H | 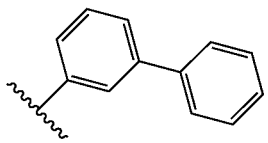 [SMILES: *c1cccc(-c2ccccc2)c1] | 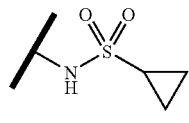 |

-continued

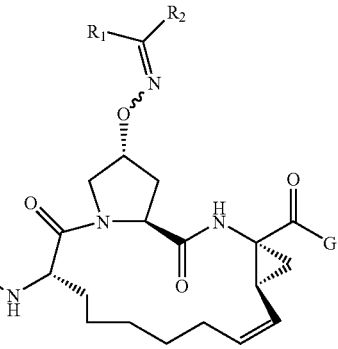

(B)

| Compound | Rx | R₁ | R₂ | G |
|---|---|---|---|---|
| (94) | cyclobutyl-O-C(=O)- | —H | 4-biphenyl | cyclopropylsulfonamide |
| (95) | cyclobutyl-O-C(=O)- | —H | 1-naphthyl | cyclopropylsulfonamide |
| (96) | cyclobutyl-O-C(=O)- | —H | 2-naphthyl | cyclopropylsulfonamide |
| (97) | cyclobutyl-O-C(=O)- | —CH₂CH₃ | 2-biphenyl | cyclopropylsulfonamide |
| (98) | cyclobutyl-O-C(=O)- | —H | 2-pyridyl | cyclopropylsulfonamide |
| (99) | cyclobutyl-O-C(=O)- | —H | 3-pyridyl | cyclopropylsulfonamide |
| (100) | cyclobutyl-O-C(=O)- | —H | 4-pyridyl | cyclopropylsulfonamide |

-continued
(B)
| Compound | Rx | R₁ | R₂ | G |
|---|---|---|---|---|
| (101) | 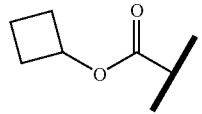 | —H | 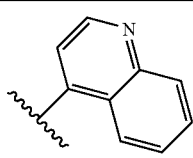 | 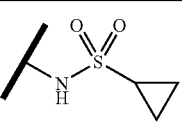 |
| (102) | 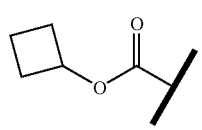 | —H | 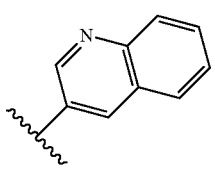 [SMILES: *c1cnc2ccccc2c1] | 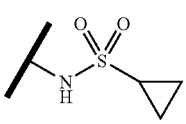 |
| (103) | 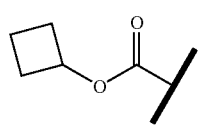 | —H | 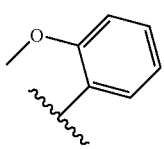 [SMILES: *c1ccccc1OC] | 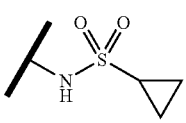 |
| (104) | 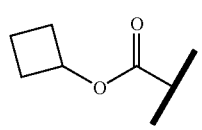 | —H | 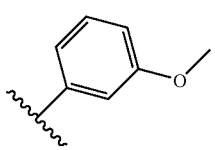 | 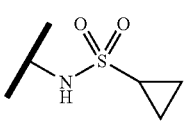 |
| (105) | 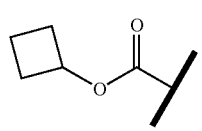 | —H | 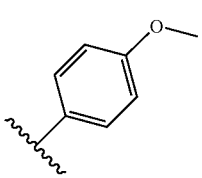 [SMILES: *c1ccc(OC)cc1] | 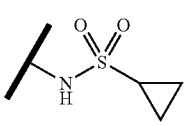 |
| (106) | 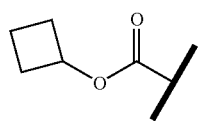 | —H | 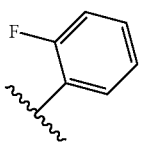 [SMILES: *c1ccccc1F] | 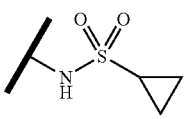 |
| (107) | 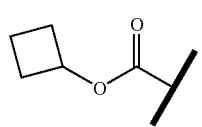 | —H | 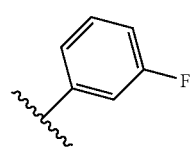 [SMILES: *c1cccc(F)c1] | 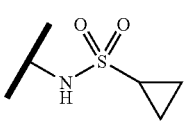 |

-continued
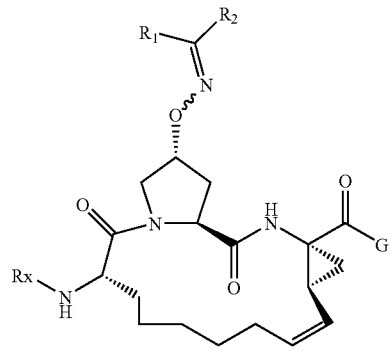
(B)
| Compound | Rx | R₁ | R₂ | G |
|---|---|---|---|---|
| (108) | 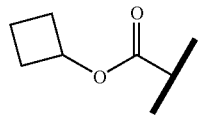 | —H | 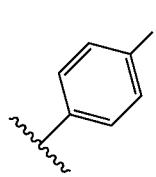 | 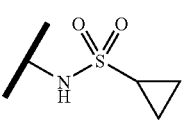 |
| (109) | 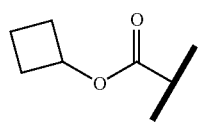 | —H | 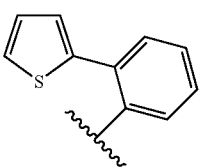 [SMILES: *c1ccccc1-c1cccs1] | 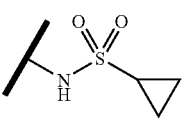 |
| (110) | 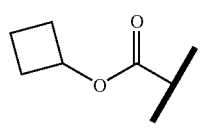 | —H | 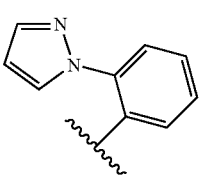 [SMILES: *c1ccccc1-n1cccn1] | 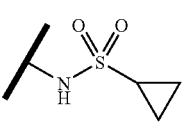 |
| (111) | 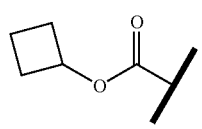 | —H | 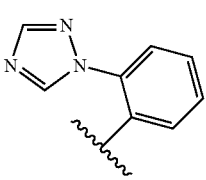 [SMILES: *c1ccccc1-n1cncn1] | 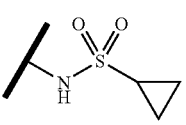 |
| (112) | 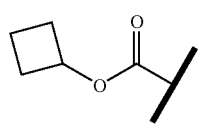 | —H | 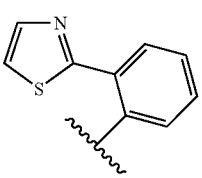 [SMILES: *c1ccccc1-c1nccs1] | 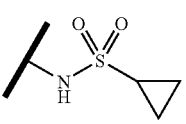 |
| (113) | 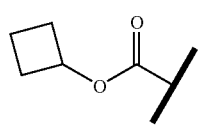 | —H | 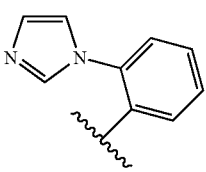 [SMILES: *c1ccccc1-n1ccnc1] | 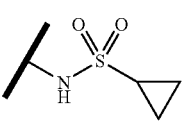 |

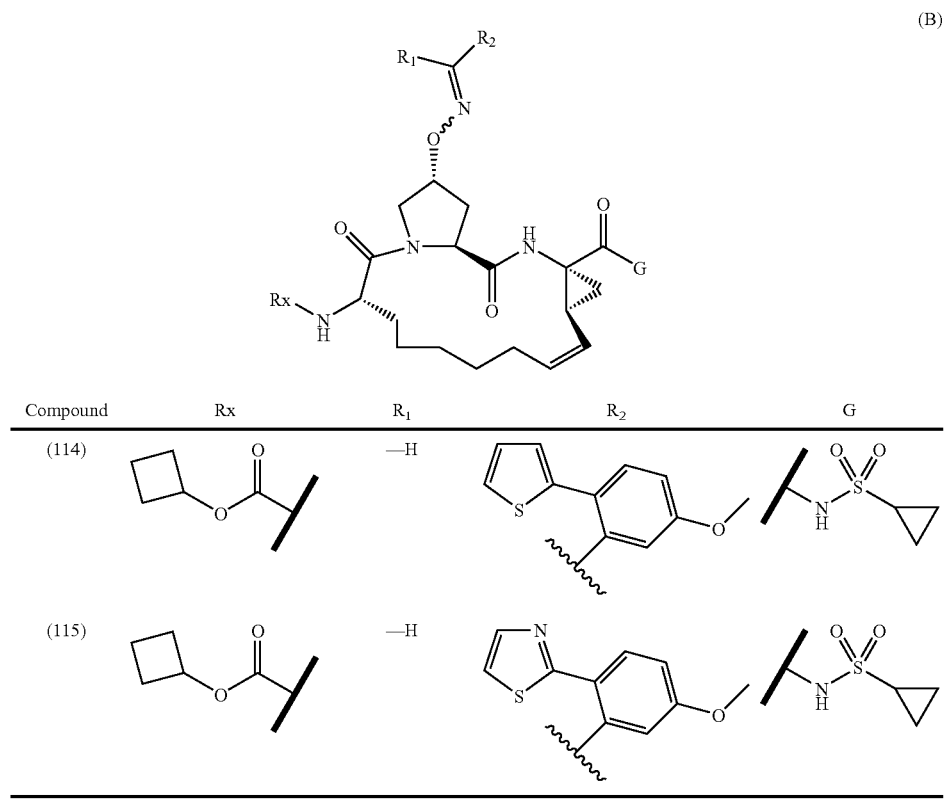

| Compound | Rx | R₁ | R₂ | G |
|---|---|---|---|---|
| (114) | cyclobutyloxycarbonyl | —H | 2-thienyl-methoxyphenyl | cyclopropylsulfonamide |
| (115) | cyclobutyloxycarbonyl | —H | 2-thiazolyl-methoxyphenyl | cyclopropylsulfonamide |

Example 116

Compound of Formula B, Wherein Rx=Cyclopentyloxycarbonyl, $R_1$ and $R_2$ Taken Together with the Carbon Atom to which they are Attached are

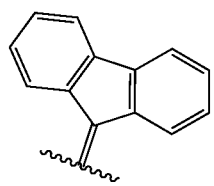 [SMILES: *=C1c2ccccc2-c2ccccc21]

and G=OH

Step 116a.

The title compound was prepared with compound from step 2c of Example 2 and 9-Fluorenone via the similar conditions described in step 3a of Example 3.

MS (ESI): m/z 683.20 [M+H].

Step 116b.

The title compound was prepared with compound from step 116a via the similar conditions described in step 3b of Example 3.

MS (ESI): m/z=655.20 [M+H].

Example 117

Compound of Formula B, Wherein Rx=Cyclopentyloxycarbonyl, $R_1$ and $R_2$ Taken Together with the Carbon Atom to which they are Attached are

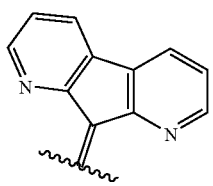 [SMILES: *=C1c2ncccc2-c2cccnc21]

and G=OH

Step 117a.

The title compound was prepared with compound from step 2c of Example 2 and 1,8-Diazafluoren-9-one via the similar conditions described in step 3a of Example 3.

MS (ESI): m/z=685.20 [M+H].

Step 117b.

The title compound was prepared with compound from step 117a via the similar conditions described in step 3b of Example 3.

MS (ESI): m/z=657.21 [M+H].

Example 118

Compound of Formula B, Wherein Rx=Cyclopentyloxycarbonyl, $R_1$ and $R_2$ Taken Together with the Carbon Atom to which they are Attached are

and G=OH

Step 118a.

The title compound was prepared with compound from step 2c of Example 2 and 4,5-Diazafluoren-9-one via the similar conditions described in step 3a of Example 3.

MS (ESI): m/z=685.30 [M+H].

Step 118b.

The title compound was prepared with compound from step 118a via the similar conditions described in step 3b of Example 3.

MS (ESI): m/z=657.33 [M+H].

Example 119

Compound of Formula B, Wherein Rx=Cyclopentyloxycarbonyl, $R_1$ and $R_2$ Taken Together with the Carbon Atom to which they are Attached are

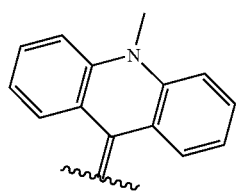 [SMILES: *=C1c2ccccc2N(C)c2ccccc21]

and G=OH

Step 119a.

The title compound was prepared with compound from step 2c of Example 2 and 10-Methyl-10H-acridin-9-one via the similar conditions described in step 3a of Example 3.

MS (ESI): m/z 712.40 [M+H].

Step 119b.

The title compound was prepared with compound from step 119a via the similar conditions described in step 3b of Example 3.

MS (ESI): m/z=684.22 [M+H].

Example 120

Compound of Formula B, Wherein Rx=Cyclopentyloxycarbonyl, $R_1$ and $R_2$ Taken Together with the Carbon Atom to which they are Attached are

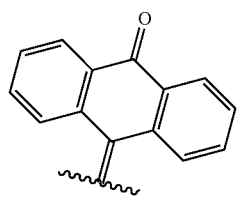 [SMILES: *=C1c2ccccc2C(=O)c2ccccc21]

and G=OH

Step 120a.

The title compound was prepared with compound from step 2c of Example 2 and Anthraquinone via the similar conditions described in step 3a of Example 3.

MS (ESI): m/z=711.27 [M+H].

Step 120b.

The title compound was prepared with compound from step 120a via the similar conditions described in step 3b of Example 3.

MS (ESI): m/z=683.26 [M+H].

Example 121

Compound of Formula B, Wherein Rx=Cyclopentyloxycarbonyl, $R_1$ and $R_2$ Taken Together with the Carbon Atom to which they are Attached are

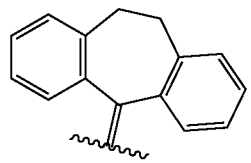 [SMILES: *=C1c2ccccc2CCc2ccccc21]

and G=OH

Step 121a.

The title compound was prepared with compound from step 2c of Example 2 and Dibenzosuberone via the similar conditions described in step 3a of Example 3.

MS (ESI): m/z=711.32 [M+H].

Step 121b.

The title compound was prepared with compound from step 121a via the similar conditions described in step 3b of Example 3.

MS (ESI): m/z=683.23 [M+H].

Example 122

Compound of Formula B, Wherein Rx=Cyclopentyloxycarbonyl, $R_1$ and $R_2$ Taken Together with the Carbon Atom to which they are Attached are

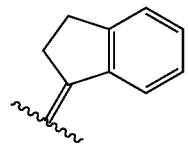 [SMILES: *=C1CCc2ccccc21]

and G=OH

Step 122a.

The title compound was prepared with compound from step 2c of Example 2 and Indan-1-one via the similar conditions described in step 3a of Example 3.

Step 122b.

The title compound was prepared with compound from step 122a via the similar conditions described in step 3b of Example 3.

MS (ESI): m/z=607.23 [M+H].

Example 123

Compound of Formula B, Wherein Rx=Cyclopentyloxycarbonyl, $R_1$ and $R_2$ Taken Together with the Carbon Atom to which they are Attached are

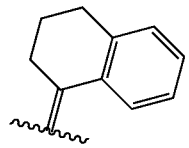 [SMILES: *=C1CCCc2ccccc21]

and G=OH

Step 123a.

The title compound was prepared with compound from step 2c of Example 2 and 1-Tetralone via the similar conditions described in step 3a of Example 3.

Step 123b.

The title compound was prepared with compound from step 123a via the similar conditions described in step 3b of Example 3.

MS (ESI): m/z=621.24 [M+H].

Example 124

Compound of Formula B, Wherein Rx=Cyclopentyloxycarbonyl, $R_1$ and $R_2$ Taken Together with the Carbon Atom to which they are Attached are

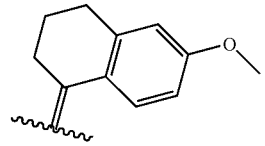

and G=OH

Step 124a.

The title compound was prepared with compound from step 2c of Example 2 and 6-Methoxy-1-tetralone via the similar conditions described in step 3a of Example 3.

MS (ESI): m/z=679.22 [M+H].

Step 124b.

The title compound was prepared with compound from step 124a via the similar conditions described in step 3b of Example 3.

MS (ESI): m/z=651.29 [M+H].

Example 125

Compound of Formula B, Wherein Rx=Cyclopentyloxycarbonyl, $R_1$ and $R_2$ Taken Together with the Carbon Atom to which they are Attached are

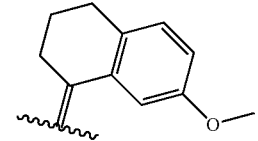 [SMILES: *=C1CCCc2ccc(OC)cc21]

and G=OH

Step 125a.

The title compound was prepared with compound from step 2c of Example 2 and 7-Methoxy-1-tetralone via the similar conditions described in step 3a of Example 3.

MS (ESI): m/z=679.22 [M+H].

Step 125b.

The title compound was prepared with compound from step 125a via the similar conditions described in step 3b of Example 3.

MS (ESI): m/z=651.29 [M+H].

Example 126

Compound of Formula B, Wherein
Rx=Cyclopentyloxycarbonyl, R₁ and R₂ Taken Together with the Carbon Atom to which they are Attached are

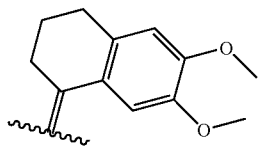

and G=OH

Step 126a.

The title compound was prepared with compound from step 2c of Example 2 and 6,7-Dimethoxy-1-tetralone via the similar conditions described in step 3a of Example 3.

MS (ESI): m/z=709.22 [M+H].

Step 126b.

The title compound was prepared with compound from step 126a via the similar conditions described in step 3b of Example 3.

MS (ESI): m/z=681.30 [M+H].

Example 127

Compound of Formula B, Wherein
Rx=Cyclopentyloxycarbonyl, R₁ and R₂ Taken Together with the Carbon Atom to which they are Attached are

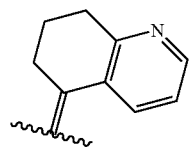

and G=OH

Step 127a.

The title compound was prepared with compound from step 2c of Example 2 and 5,6,7,8-Tetrahydroquinolinone-5 via the similar conditions described in step 3a of Example-3.

MS (ESI): m/z=650.23 [M+H].

Step 127b.

The title compound was prepared with compound from step 127a via the similar conditions described in step 3b of Example 3.

MS (ESI): m/z=622.29 [M+H].

Example 128

Compound of Formula B, Wherein
Rx=Cyclopentyloxycarbonyl, R₁ and R₂ Taken Together with the Carbon Atom to which they are Attached are

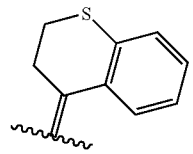 [SMILES: *=C1CCSc2ccccc21]

and G=OH

Step 128a.

The title compound was prepared with compound from step 2c of Example 2 and Thiochroman-4-one via the similar conditions described in step 3a of Example 3.

MS (ESI): m/z=667.18 [M+H].

Step 128b.

The title compound was prepared with compound from step 128a via the similar conditions described in step 3b of Example 3.

MS (ESI): m/z=639.23 [M+H].

Example 129

Compound of Formula B, Wherein
Rx=Cyclopentyloxycarbonyl, R₁ and R₂ Taken Together with the Carbon Atom to which they are Attached are

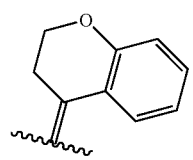 [SMILES: *=C1CCOc2ccccc21]

and G=OH

Step 129a.

The title compound was prepared with compound from step 2c of Example 2 and Chroman-4-one via the similar conditions described in step 3a of Example 3.

MS (ESI): m/z=651.31 [M+H].

Step 129b.

The title compound was prepared with compound from step 129a via the similar conditions described in step 3b of Example-3.

MS (ESI): m/z=623.36 [M+H].

Example 130

Compound of Formula B, Wherein Rx=Cyclopentyloxycarbonyl, $R_1$ and $R_2$ Taken Together with the Carbon Atom to which they are Attached are

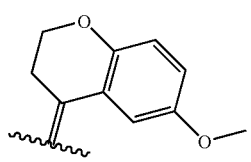 [SMILES: *=C1CCOc2ccc(OC)cc21]

and G=OH

Step 130a.

The title compound was prepared with compound from step 2c of Example 2 and 6-Methoxy-chroman-4-one via the similar conditions described in step 3a of Example 3.

MS (ESI): m/z=681.21[M+H].

Step 130b.

The title compound was prepared with compound from step 130a via the similar conditions described in step 3b of Example 3.

MS (ESI): m/z=653.24 [M+H].

Example 131

Compound of Formula B, Wherein Rx=Cyclopentyloxycarbonyl, $R_1$ and $R_2$ Taken Together with the Carbon Atom to which they are Attached are

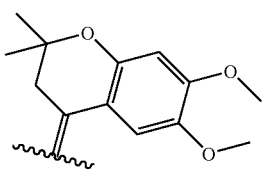

and G=OH

Step 131a.

The title compound was prepared with compound from step 2c of Example 2 and 6,7-Dimethoxy-2,2-dimethyl-chroman-4-one via the similar conditions described in step 3a of Example 3.

MS (ESI): m/z=739.32 [M+H].

Step 131b.

The title compound was prepared with compound from step 131a via the similar conditions described in step 3b of Example 3.

MS (ESI): m/z=711.31 [M+H].

Example 132

Compound of Formula B, Wherein Rx=Cyclopentyloxycarbonyl, $R_1$ and $R_2$ Taken Together with the Carbon Atom to which they are Attached are

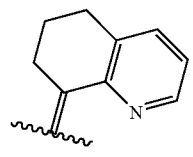 [SMILES: *=C1CCCc2cccnc21]

and G=OH

Step 132a.

The title compound was prepared with compound from step 2c of Example 2 and 6,7-dihydro-5H-quinolin-8-one via the similar conditions described in step 3a of Example 3.

MS (ESI): m/z=650.21 [M+H].

Step 132b.

The title compound was prepared with compound from step 132a via the similar conditions described in step 3b of Example 3.

MS (ESI): m/z=622.23 [M+H].

Example 133

Compound of Formula B, Wherein Rx=Cyclopentyloxycarbonyl, $R_1$ and $R_2$ Taken Together with the Carbon Atom to which they are Attached are

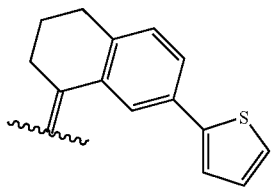 [SMILES: *=C1CCCc2ccc(-c3cccs3)cc21]

and G=OH

Step 133a.

The title compound was prepared with compound from step 2c of Example 2 and 7-Thiophen-2-yl-3,4-dihydro-2H-naphthalen-1-one via the similar conditions described in step 3a of Example 3.

MS (ESI): m/z=731.28 [M+H].

Step 133b.

The title compound was prepared with compound from step 133a via the similar conditions described in step 3b of Example 3.

MS (ESI): m/z=703.21 [M+H].

Example 134

Compound of Formula B, Wherein Rx=Cyclopentyloxycarbonyl, $R_1$ and $R_2$ Taken Together with the Carbon Atom to which they are Attached are

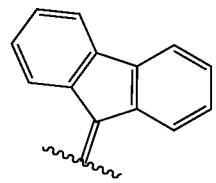

and G=NHSO$_2$-cyclopropyl

To a solution of compound from step 116b of Example 116 in DMF was added CDI. The reaction mixture was stirred at 40° C. for 1 h and then added cyclopropylsulfonamide and DBU. The reaction mixture was stirred overnight at 40° C. The reaction mixture was extracted with EtOAc. The organic extracts were washed with 1M NaHCO$_3$, brine, dried over Na$_2$SO$_4$, filtered and concentrated. The residue was purified by silica gel chromatograph to give desired product.

MS (ESI): m/z=758.14 [M+H].

Example 135

Compound of Formula B, Wherein Rx=Boc, $R_1$ and $R_2$ Taken Together with the Carbon Atom to which they are Attached are

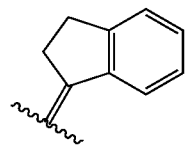 [SMILES: *=C1CCc2ccccc21]

and G=OH

Step 135a.

The title compound was prepared with compound from step 1f of Example 1 and 1-indanone via the similar conditions described in step 3a of Example 3.

MS (ESI): m/z=623.34 [M+H].

Step 135b.

The title compound was prepared with compound from step 135a via the similar conditions described in step 3b of Example 3.

MS (ESI): m/z=595.32 [M+H].

Example 136

Compound of Formula B, Wherein Rx=Boc, $R_1$ and $R_2$ Taken Together with the Carbon Atom to which they are Attached are

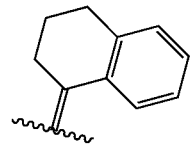 [SMILES: *=C1CCCc2ccccc21]

and G=OH

Step 136a.

The title compound was prepared with compound from step 1f of Example 1 and 1-tetralone via the similar conditions described in step 3a of Example 3.

MS (ESI): m/z=637.45 [M+H].

Step 136b.

The title compound was prepared with compound from step 136a via the similar conditions described in step 3b of Example 3.

MS (ESI): m/z=609.34 [M+H].

Example 137

Compound of Formula B, Wherein Rx=Cyclopentyloxycarbonyl, $R_1$ and $R_2$ Taken Together with the Carbon Atom to which they are Attached are

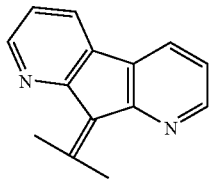 [SMILES: CC(C)=C1c2ncccc2-c2cccnc21]

and G=NHSO$_2$-cyclopropyl

To a solution of compound from step 117b of Example 117 in DMF was added CDI. The reaction mixture was stirred at 40° C. for 1 h and then added cyclopropylsulfonamide and DBU. The reaction mixture was stirred overnight at 40° C. The reaction mixture was extracted with EtOAc. The organic extracts were washed with 1M NaHCO$_3$, brine, dried over Na$_2$SO$_4$, filtered and concentrated. The residue was purified by silica gel chromatograph to give desired product.

MS (ESI): m/z=760.18 [M+H].

Example 138

Compound of Formula B, Wherein Rx=Cyclopentyloxycarbonyl, $R_1$ and $R_2$ Taken Together with the Carbon Atom to which they are Attached are

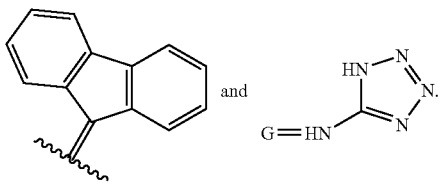

To a solution of compound from step 116b of Example 116 in DMF was added HATU and DIEA. The reaction mixture was stirred at 40° C. for 20 min and then added 5-aminotetrazole. The reaction mixture was stirred overnight at 90° C. The reaction mixture was directly purified by HPLC to give desired product.

MS (ESI): m/z=722.31 [M+H].

Example 139

Compound of Formula B, Wherein Rx=Boc, $R_1$ and $R_2$ Taken Together with the Carbon Atom to which they are Attached are

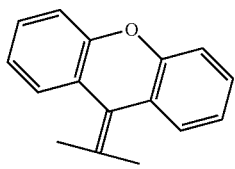 [SMILES: CC(C)=C1c2ccccc2Oc2ccccc21]

and G=OH

Step 139a.

The mixture of xanthone (1.0 g), hydroxylamine hydrochloride (1.77 g) and pyridine (12 ml) was heated to 110° C. for 2 days. The reaction mixture was concentrated and the residue was extracted with EtOAc. The organic layer was washed with 1% HCl, water, brine, dried over $Na_2SO_4$, filtered and concentrated. The residue was purified by silica gel chromatography to give desired product.

MS (ESI): m/z=212.08 [M+H].

Step 139b.

To a solution of the macrocyclic peptide precursor from step 1d of Example 1 (500 mg, 1.01 mmol) and DIEA (0.4 ml, 2 mmol) in 2.0 ml DCM, mesylate chloride (0.1 ml) was added slowly at 0° C. where the reaction was kept for 3 hours. 30 mL EtOAc was then added and followed by washing with 5% citric acid 2×10 ml, water 2×10 ml, 1M $NaHCO_3$ 2×10 ml and brine 2×10 ml, respectively. The organic phase was dried over anhydrous $Na_2SO_4$ and evaporated, yielding the title compound mesylate that was used for next step synthesis without need for further purification.

MS (ESI): m/z=572.34 [M+H].

Step 139c.

To a solution of the mesylate from step 139b (50 mg) in 2 mL DMF, was added 37 mg of the oxime from step 139a and anhydrous sodium carbonate (86 mg). The resulting reaction mixture was stirred vigorously at 60° C. for 12 hours. The reaction mixture was extracted with EtOAc. The organic layer was washed with 1M $NaHCO_3$, water, brine, dried over $Na_2SO_4$, filtered and concentrated. The residue was purified by silica gel chromatography to give 22 mg of desired product.

MS (ESI): m/z=687.39 [M+H].

Step 139d.

The title compound was prepared with compound from step 139c via the similar conditions described in step 3b of Example 3.

MS (ESI): m/z=659.33 [M+H].

Example 140

Compound of Formula B, Wherein Rx=Boc, $R_1$ and $R_2$ Taken Together with the Carbon Atom to which they are Attached are

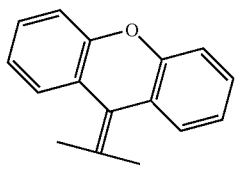 [SMILES: CC(C)=C1c2ccccc2Oc2ccccc21]

and G=NHSO$_2$-cyclopropyl

The title compound was prepared with compound from step 139d via the similar conditions described in Example 134.

MS (ESI): m/z=762.21 [M+H].

Example 141

Compound of Formula B, Wherein Rx=Cyclopentyloxycarbonyl, $R_1$ and $R_2$ Taken Together with the Carbon Atom to which they are Attached are

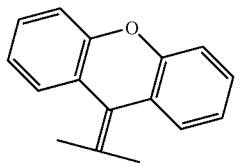 [SMILES: CC(C)=C1c2ccccc2Oc2ccccc21]

and G=NHSO$_2$-cyclopropyl

Step 141a.

The solution of the compound from Example 140 in 5 ml 4N HCl/Dioxne was stirred at RT for 1 h. The reaction mixture was concentrated in vacuum. The residue was evaporated twice with DCM. The desired product was carried out directly to the next step.

MS (ESI): m/z=662.19 [M+H].

Step 141b.

To the solution of the compound from Example 141a in 2 ml DCM was added DIEA (0.32 mmol) and cyclopentylchloroformate (0.096 mmol). The reaction mixture was stirred at RT for 1 h. The reaction mixture was extracted with EtOAc. The organic layer was washed with 1M NaHCO$_3$, water, brine, dried over Na$_2$SO$_4$, filtered and concentrated. The residue was purified by HPLC to give 16 mg of desired product.

MS (ESI): m/z=774.31 [M+H].

13C(CD3OD): 178.2, 173.5, 169.4, 156.6, 152.9, 151.4, 141.1, 135.6, 131.9, 131.6, 130.7, 124.9, 124.6, 123.6, 122.8, 119.1, 117.1, 116.5, 116.2, 83.0, 77.4, 59.8, 53.1, 52.5, 43.9, 34.4, 32.4, 32.3, 30.7, 29.9, 27.4, 27.1, 26.5, 23.2, 22.0, 21.0.

Example 142

Compound of Formula B, Wherein Rx=Boc, R$_1$ and R$_2$ Taken Together with the Carbon Atom to which they are Attached are

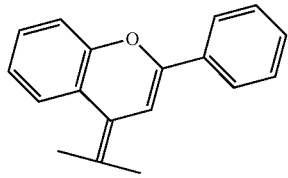 [SMILES: CC(C)=C1C=C(c2ccccc2)Oc2ccccc21]

and G=OH

Step 142a.

The oxime was prepared with flavanone via the similar conditions described in step 139a of Example 139.

MS (ESI): m/z=238.10 [M+H].

Step 142b.

To a solution of the cyclic precursor from step 1d 100 mg, oxime from step 142a (71 mg) and PPh$_3$ (105 mg) in THF was added DEAD (63 μL) at 0° C. The reaction mixture was stirred for overnight at room temperature. The mixture was then concentrated and purified by silica gel chromatography to give desired product.

MS (ESI): m/z=713.40 [M+H].

Step 142c.

The title compound was prepared with compound from step 142b via the similar conditions described in step 3b of Example 3.

MS (ESI): m/z=685.25 [M+H].

Example 143

Compound of Formula B, Wherein Rx=Boc, R$_1$ and R$_2$ Taken Together with the Carbon Atom to which they are Attached are

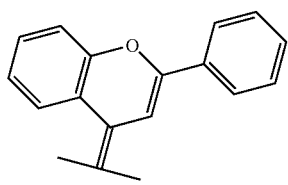 [SMILES: CC(C)=C1C=C(c2ccccc2)Oc2ccccc21]

and G=NHSO$_2$-cyclopropyl

The title compound was prepared with compound from step 142c of Example 142 via the similar conditions described in Example 134.

MS (ESI): m/z=788.37 [M+H].

Example 144

Compound of Formula B, Wherein Rx=Cyclopentyloxycarbonyl, R$_1$ and R$_2$ Taken Together with the Carbon Atom to which they are Attached are

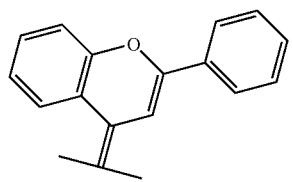 [SMILES: CC(C)=C1C=C(c2ccccc2)Oc2ccccc21]

and G=NHSO$_2$-cyclopropyl

The title compound was prepared with compound from Example 143 via the similar conditions described in Example 141.

MS (ESI): m/z=800.39 [M+H].

13C (CD3OD): 177.5, 173.8, 169.3, 166.4, 163.4, 157.1, 153.6, 135.6, 131.6, 129.9, 129.1, 129.0, 127.6, 126.9, 124.9, 121.7, 117.7, 114.0, 101.4, 77.7, 76.9, 59.5, 53.7, 52.9, 43.6, 34.5, 32.7, 31.8, 30.6, 30.0, 27.5, 27.4, 26.6, 23.2, 22.1, 20.9.

Example 145

Compound of Formula B, Wherein Rx=Boc, R$_1$ and R$_2$ Taken Together with the Carbon Atom to which they are Attached are

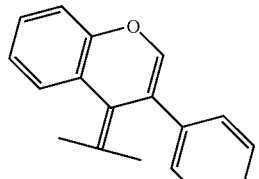

and G=OH

The title compound was prepared with isoflavanone via the similar conditions described in Example 142.

MS (ESI): m/z=685.20 [M+H].

Example 146

Compound of Formula B, Wherein Rx=Boc, $R_1$ and $R_2$ Taken Together with the Carbon Atom to which they are Attached are

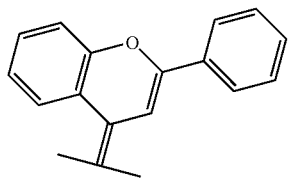 [SMILES: CC(C)=C1C=C(c2ccccc2)Oc2ccccc21]

and G=NHSO$_2$-cyclopropyl

The title compound was prepared with compound from Example 145 via the similar conditions described in Example 134.
MS (ESI): m/z=788.29 [M+H].
13C (CD3OD): 177.7, 173.3, 169.4, 165.7, 156.8, 154.4, 135.3, 132.8, 121.9, 131.0, 128.4, 128.1, 127.7, 126.8, 126.1, 125.0, 121.1, 120.5, 113.4, 90.4, 79.9, 76.3, 59.7, 52.5, 52.4, 43.6, 35.0, 32.2, 30.6, 30.1, 27.5, 27.3, 26.4, 21.7, 21.1.

Example 147

Compound of Formula B, Wherein Rx=Cyclopentyloxycarbonyl, $R_1$ and $R_2$ Taken Together with the Carbon Atom to which they are Attached are

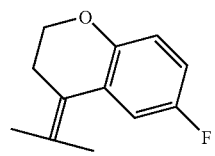

and G=OH

The title compound was prepared with 6-fluoro-4-chromanone via the similar conditions described in Example 3.
MS (ESI): m/z=641.26 [M+H].

Example 148

Compound of Formula B, Wherein Rx=Cyclopentyloxycarbonyl, $R_1$ and $R_2$ Taken Together with the Carbon Atom to which they are Attached are

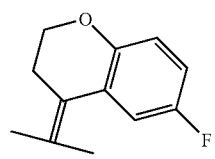

and G=NHSO$_2$-cyclopropyl

The title compound was prepared with compound from Example 147 via the similar conditions described in Example 134.
MS (ESI): m/z=744.36 [M+H].
13C (CD3OD): 176.9, 174.0, 168.1, 158.2, 156.3, 156.0, 152.9, 149.9, 136.3, 124.4, 118.9, 118.8, 118.5, 118.3, 110.1, 109.9, 81.3, 78.4, 65.0, 60.0, 53.4, 52.4, 44.4, 34.1, 32.6, 32.5, 31.0, 29.8, 27.1, 26.9, 26.0, 23.9, 23.5, 23.4, 22.0, 20.8.

Example 149

Compound of Formula B, Wherein Rx=Cyclopentyloxycarbonyl, $R_1$ and $R_2$ Taken Together with the Carbon Atom to which they are Attached are

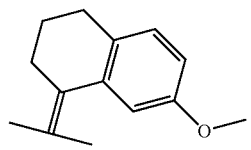

and G=NHSO$_2$-cyclopropyl

The title compound was prepared with compound from Example 125 via the similar conditions described in Example 134.
MS (ESI): m/z=754.39 [M+H].
13C (CD3OD): 176.9, 174.1, 168.2, 157.9, 156.2, 136.3, 132.5, 130.9, 129.6, 124.2, 116.9, 107.7, 80.8, 78.6, 60.2, 55.4, 53.6, 52.4, 44.3, 34.4, 32.6, 32.5, 31.0, 29.8, 28.8, 27.2, 26.9, 26.0, 24.3, 23.5, 23.4, 21.9, 21.5, 20.8.

Example 150

Compound of Formula B, Wherein Rx=Cyclopentyloxycarbonyl, $R_1$ and $R_2$ Taken Together with the Carbon Atom to which they are Attached are

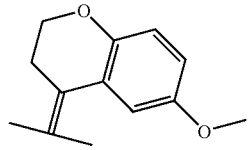

and G=NHSO$_2$-cyclopropyl

The title compound was prepared with compound from Example 130 via the similar conditions described in Example 134.
MS (ESI): m/z=756.35 [M+H].
13C (CD3OD): 177.1, 173.5, 168.1, 155.8, 153.9, 151.2, 150.5, 136.2, 124.4, 119.5, 118.6, 118.1, 106.4, 81.2, 78.1, 65.0, 59.9, 55.7, 53.3, 52.3, 44.4, 34.2, 32.7, 32.6, 32.5, 31.0, 29.7, 27.2, 26.0, 24.2, 23.5, 23.4, 22.0, 20.8.

Example 151 to Example 186 (Formula B) are Made Following the Procedures Described in Examples 1, 3, 134 or 141
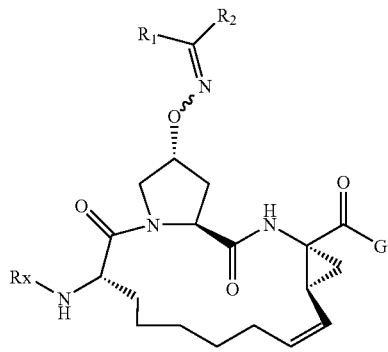

-continued
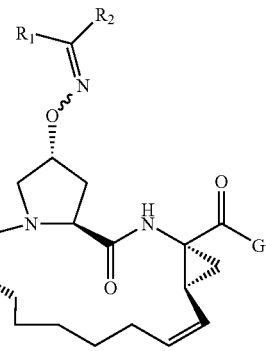
(B)
| Compound | Rx | R₁R₂ | G |
|---|---|---|---|
| (157) |  | 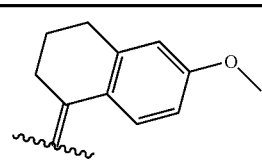 | 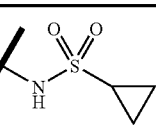 |
| (158) | 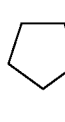 | 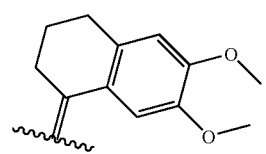 [SMILES: *=C1CCCc2cc(OC)c(OC)cc21] | 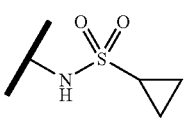 |
| (159) | 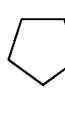 | 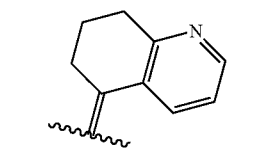 [SMILES: *=C1CCCc2ncccc21] | 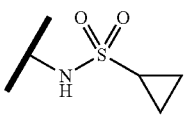 |
| (160) | 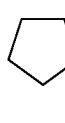 | 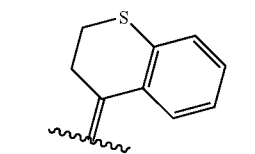 | 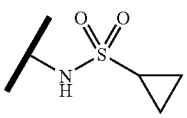 |
| (161) |  | 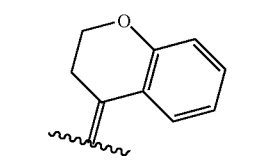 [SMILES: *=C1CCOc2ccccc21] | 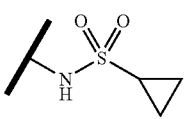 |
| (162) | 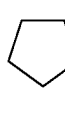 | 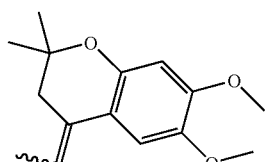 | 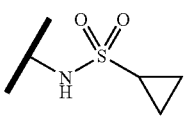 |
| (163) | 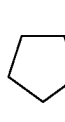 | 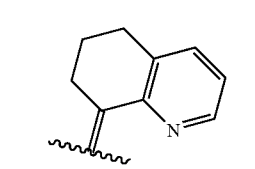 | 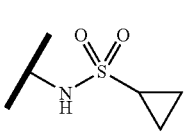 |

-continued

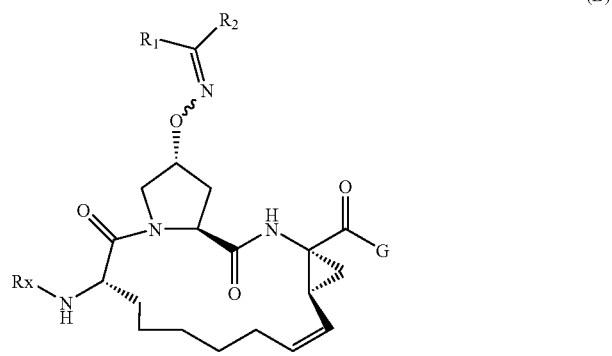

(B)

| Compound | Rx | R₁R₂ | G |
|---|---|---|---|
| (164) | cyclopentyl-O-C(=O)- | 6,7-dihydro-5H-naphthalen-8-ylidene with 2-thienyl substituent | -NH-S(O)₂-cyclopropyl |
| (165) | cyclobutyl-O-C(=O)- | 5H-indeno[1,2-b:3,4-b']dipyridin-5-ylidene | -NH-S(O)₂-cyclopropyl |
| (166) | cyclobutyl-O-C(=O)- | 10-methyl-10H-acridin-9-ylidene | -NH-S(O)₂-cyclopropyl |
| (167) | cyclobutyl-O-C(=O)- | 10-oxo-10H-anthracen-9-ylidene | -NH-S(O)₂-cyclopropyl |
| (168) | cyclobutyl-O-C(=O)- | 10,11-dihydro-5H-dibenzo[a,d]cyclohepten-5-ylidene | -NH-S(O)₂-cyclopropyl |
| (169) | cyclobutyl-O-C(=O)- | 2,3-dihydro-1H-inden-1-ylidene | -NH-S(O)₂-cyclopropyl |

-continued
(B)
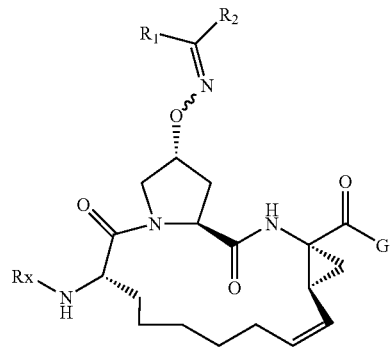
| Compound | Rx | R₁R₂ | G |
|---|---|---|---|
| (170) | | | |
| (171) | | | |
| (172) | | | |
| (173) | | | |
| (174) | | | |
| (175) | | | |
| (176) | | | |

-continued (B)

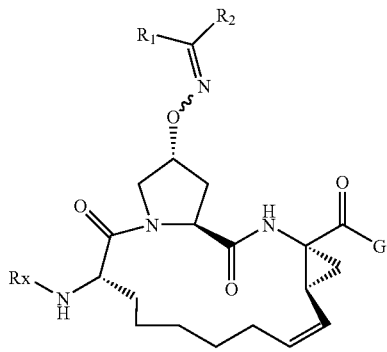

| Compound | Rx | R₁R₂ | G |
|---|---|---|---|
| (177) | cyclobutyl-O-C(=O)- | 5,6,7,8-tetrahydroquinolin-8-ylidene | -NHS(O)₂-cyclopropyl |
| (178) | cyclobutyl-O-C(=O)- | 6-(thiophen-2-yl)-3,4-dihydronaphthalen-1(2H)-ylidene | -NHS(O)₂-cyclopropyl |
| (179) | cyclobutyl-O-C(=O)- | 9H-fluoren-9-ylidene | -NHS(O)₂-cyclopropyl |
| (180) | cyclobutyl-O-C(=O)- | 5H-cyclopenta[2,1-b:3,4-b']dipyridin-5-ylidene | -NHS(O)₂-cyclopropyl |
| (181) | cyclobutyl-O-C(=O)- | 9H-xanthen-9-ylidene | -NHS(O)₂-cyclopropyl |
| (182) | cyclobutyl-O-C(=O)- | 2-phenyl-4H-chromen-4-ylidene | -NHS(O)₂-cyclopropyl |

-continued

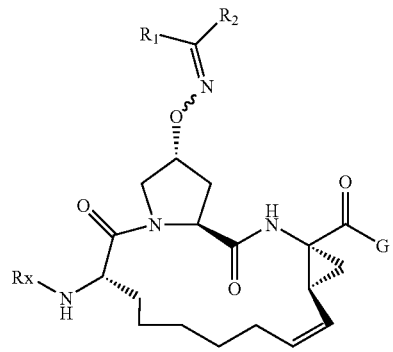

(B)

| Compound | Rx | R₁R₂ | G |
|---|---|---|---|
| (183) | cyclobutyl-O-C(=O)-CH- | (4-phenyl-chromen-4-ylidene)methyl | -NHS(=O)₂-cyclopropyl |
| (184) | cyclobutyl-O-C(=O)-CH- | (6-fluoro-chroman-4-ylidene)methyl | -NHS(=O)₂-cyclopropyl |
| (185) | cyclobutyl-O-C(=O)-CH- | (7-methoxy-tetralin-1-ylidene)methyl | -NHS(=O)₂-cyclopropyl |
| (186) | cyclobutyl-O-C(=O)-CH- | (6-methoxy-chroman-4-ylidene)methyl | -NHS(=O)₂-cyclopropyl |

The compounds of the present invention exhibit potent inhibitory properties against the HCV NS3 protease. The following examples describe assays in which the compounds of the present invention can be tested for anti-HCV effects.

Example 187

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluorescence is measured with a Molecular Devices Fluoromax (or equivalent) using an excitation wavelength of 355 nm and an emission wavelength of 485 nm.

The assay is run in Corning white half-area 96-well plates (VWR 29444-312 [Corning 3693]) with full-length NS3 HCV protease 1b tethered with NS4A cofactor (final enzyme concentration 1 to 15 nM). The assay buffer is complemented with 10 μM NS4A cofactor Pep 4A (Anaspec 25336 or in-house, MW 1424.8). RET S1 (Ac-Asp-Glu-Asp(EDANS)-Glu-Glu-Abu-[COO]Ala-Ser-Lys-(DABCYL)-$NH_2$, AnaSpec 22991, MW 1548.6) is used as the fluorogenic peptide substrate. The assay buffer contains 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH, [−20° C.] and HCV Inh 2 (Anaspec 25346, MW 913.1) Ac-Asp-Glu-Dif-Cha-Cys-OH, are used as reference compounds.

IC50 values are calculated using XLFit in ActivityBase (IDBS) using equation 205: $y = A + ((B-A)/(1+((C/x)^D)))$.

Example 188

Cell-Based Replicon Assay

Quantification of HCV replicon RNA (HCV Cell Based Assay) is accomplished using the Huh 11-7 cell line (Lohmann, et al Science 285:110-113, 1999). Cells are seeded at $4\times10^3$ cells/well in 96 well plates and fed media containing DMEM (high glucose), 10% fetal calf serum, penicillin-streptomycin and non-essential amino acids. Cells are incubated in a 7.5% $CO_2$ incubator at 37° C. At the end of the incubation period, total RNA is extracted and purified from cells using Ambion RNAqueous 96 Kit (Catalog No. AM1812). To amplify the HCV RNA so that sufficient material can be detected by an HCV specific probe (below), primers specific for HCV (below) mediate both the reverse transcription of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

HCV Forward primer "RBNS5bfor"
5'GCTGCGGCCTGTCGAGCT (SEQ ID NO: 1):
HCV Reverse primer "RBNS5Brev"
5'CAAGGTCGTCTCCGCATAC (SEQ ID NO 2).

Detection of the RT-PCR product is accomplished using the Applied Biosystems (ABI) Prism 7500 Sequence Detection System (SDS) that detects the fluorescence that is emitted when the probe, which is labeled with a fluorescence reporter dye and a quencher dye, is degraded during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a standard curve of HCV RNA standards with known copy number (ABI User Bulletin #2 Dec. 11, 1997).

The RT-PCR product was detected using the following labeled probe:

```
                                          (SEQ ID NO: 3)
5' FAM-CGAAGCTCCAGGACTGCACGATGCT-TAMRA
```

FAM=Fluorescence reporter dye.
TAMRA:=Quencher dye.

The RT reaction is performed at 48° C. for 30 minutes followed by PCR. Thermal cycler parameters used for the PCR reaction on the ABI Prism 7500 Sequence Detection System are: one cycle at 95° C., 10 minutes followed by 40 cycles each of which include one incubation at 95° C. for 15 seconds and a second incubation for 60° C. for 1 minute.

To normalize the data to an internal control molecule within the cellular RNA, RT-PCR is performed on the cellular messenger RNA glyceraldehyde-3-phosphate dehydrogenase (GAPDH). The GAPDH copy number is very stable in the cell lines used. GAPDH RT-PCR is performed on the same RNA sample from which the HCV copy number is determined. The GAPDH primers and probesare contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of Compounds as Inhibitors of HCV Replication (Cell Based Assay) in Replicon Containing Huh-7 Cell Lines.

The effect of a specific anti-viral compound on HCV replicon RNA levels in Huh-11-7 cells is determined by comparing the amount of HCV RNA normalized to GAPDH (e.g. the ratio of HCV/GAPDH) in the cells exposed to compound versus cells exposed to the DMSO vehicle (negative control). Specifically, cells are seeded at $4\times10^3$ cells/well in a 96 well plate and are incubated either with: 1) media containing 1% DMSO (0% inhibition control), or 2) media/1% DMSO containing a fixed concentration of compound. 96 well plates as described above are then incubated at 37° C. for 4 days (EC50 determination). Percent inhibition is defined as:

$$\% \text{ Inhibition} = 100 - 100 * S/C1$$

where
S=the ratio of HCV RNA copy number/GAPDH RNA copy number in the sample;
C1=the ratio of HCV RNA copy number/GAPDH RNA copy number in the 0% inhibition control (media/1% DMSO).

The dose-response curve of the inhibitor is generated by adding compound in serial, three-fold dilutions over three logs to wells starting with the highest concentration of a specific compound at 1.5 uM and ending with the lowest concentration of 0.23 nM. Further dilution series (500 nM to 0.08 nM for example) is performed if the EC50 value is not positioned well on the curve. EC50 is determined with the IDBS Activity Base program "XL Fit" using a 4-parameter, non-linear regression fit (model #205 in version 4.2.1, build 16).

In the above assays, representative compounds of the present invention are found to have HCV replication inhibitory activity and HCV NS3 protease inhibitory activity. For instance, representative compounds of formulae III, IV, VIII and IX, as depicted above, showed significant HCV replication inhibitory activity. These compounds were also effective in inhibiting HCV NS3 proteases of different HCV genotypes including genotypes 1, 2, 3 and 4. As a non-limiting example, representative compounds in the preferred examples of formulae III, IV, VIII and IX showed EC50s in the range of from less than 0.2 nM to about 10 nM using cell-based replicon assays. Representative compounds of these preferred examples also inhibited HCV NS3 proteases of different HCV genotypes, such as genotypes 1a, 1b, 2a, 2b, 3a, and 4a, with IC50s in the range of from less than 0.2 nM to about 50 nM.

What is claimed is:

1. A compound represented by the formula I:

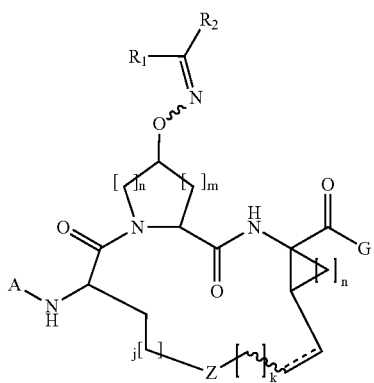

(I)

or a pharmaceutically acceptable salt thereof, wherein:

$R_1$ and $R_2$ are independently selected from the group consisting of:
a) hydrogen;
b) aryl;
c) substituted aryl;
d) heteroaryl;
e) substituted heteroaryl;
f) heterocyclic or substituted heterocyclic;
g) —$C_1$-$C_8$ alkyl, —$C_2$-$C_8$ alkenyl, or —$C_2$-$C_8$ alkynyl each containing 0, 1, 2, or 3 heteroatoms selected from O, S or N;
h) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
i) —$C_3$-$C_{12}$ cycloalkyl, or substituted —$C_3$-$C_{12}$ cycloalkyl;
j) —$C_3$-$C_{12}$ cycloalkenyl, or substituted —$C_3$-$C_{12}$ cycloalkenyl;
k) -B-$R_3$, where B is (CO), (CO)O, (CO)$NR_4$, (SO), ($SO_2$), ($SO_2$)$NR_4$; and $R_3$ and $R_4$ are independently selected from the group consisting of:
  (i) Hydrogen;
  (ii) aryl;
  (iii) substituted aryl;
  (iv) heteroaryl;
  (v) substituted heteroaryl;
  (vi) heterocyclic;
  (vii) substituted heterocyclic;
  (viii) —$C_1$-$C_8$ alkyl; —$C_2$-$C_8$ alkenyl, —$C_2$-$C_8$ alkynyl each containing 0, 1, 2, or 3 heteroatoms selected from O, S or N;
  (ix) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
  (x) —$C_3$-$C_{12}$ cycloalkyl; substituted —$C_3$-$C_{12}$ cycloalkyl;
  (xi) —$C_3$-$C_{12}$ cycloalkenyl, and substituted —$C_3$-$C_{12}$ cycloalkenyl;
alternatively, $R_1$ and $R_2$ taken together with the carbon atom to which they are attached form cyclic moiety consisting of: substituted or unsubstituted cycloalkyl, cycloalkenyl, or heterocyclic; substituted or unsubstituted cycloalkyl, cycloalkenyl, or heterocyclic each fused with one or more $R_3$; where $R_3$ is as previously defined;

G is -E-$R_3$ where E is absent, or E is O, CO, (CO)O, (CO)NH, NH, NH(CO), NH(CO)NH, NH($SO_2$)NH or $NHSO_2$; where $R_3$ is as previously defined;

Z is selected from the group consisting of $CH_2$, O, S, SO, or $SO_2$;

A is selected from the group consisting of $R_5$, (CO)$R_5$, (CO)$OR_5$, (CO)$NHR_5$, $SO_2R_5$, ($SO_2$)$OR_5$ and $SO_2NHR_5$;

$R_5$ is selected from the group consisting of:
1) aryl;
2) substituted aryl;

3) heteroaryl;
4) substituted heteroaryl;
5) heterocyclic;
6) substituted heterocyclic;
7) —$C_1$-$C_8$ alkyl; —$C_2$-$C_8$ alkenyl; —$C_2$-$C_8$ alkynyl each containing 0, 1, 2, or 3 heteroatoms selected from O, S or N;
8) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
9) —$C_3$-$C_{12}$ cycloalkyl;
10) substituted —$C_3$-$C_{12}$ cycloalkyl;
11) —$C_3$-$C_{12}$ cyclo alkenyl; and
12) substituted —$C_3$-$C_{12}$ cycloalkenyl;

j=0, 1, 2, or 3;
k=0, 1, 2, or 3;
m=0, 1, 2 or 3;
n=1, 2 or 3; and
h=0, 1, 2, or 3.

2. The compound according to claim 1 represented by formula II:

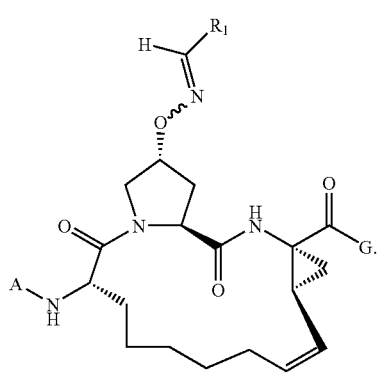

(II)

or a pharmaceutically acceptable salt thereof.

3. The compound according to claim 1 represented by formula III:

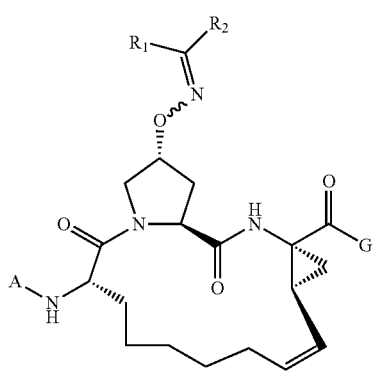

(III)

or a pharmaceutically acceptable salt thereof.

4. The compound according to claim 1 represented by formula IV:

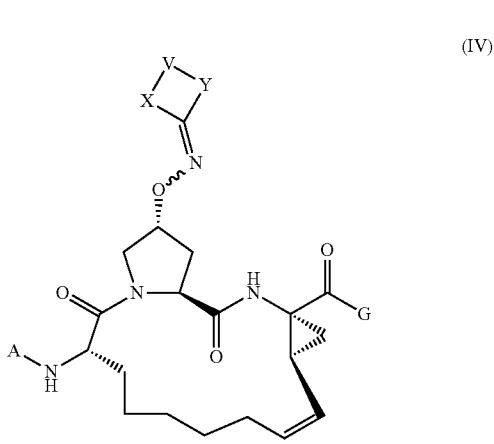

(IV)

or a pharmaceutically acceptable salt thereof,
wherein V is a direct bond, or V is CO, O, S, SO, $SO_2$, NH or $NCH_3$, or $(CH_2)_q$; where q is 1, 2, 3 or 4; and where X and Y are independently selected from the group consisting of: aryl; substituted aryl; heteroaryl; substituted heteroaryl; heterocyclic; and substituted heterocyclic.

5. The compound of claim 4, wherein

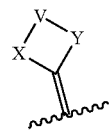

is selected from

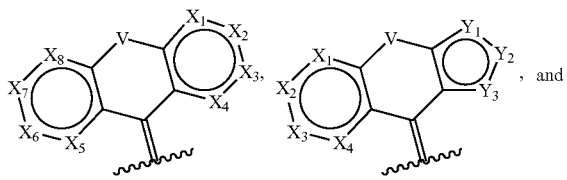

where $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is a direct bond, CO, O, S, NH, or $(CH_2)_q$, where q is 1, 2 or 3; A is selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; G is —O—$R_3$, —NH—C(O)—R$_3$, —NH—SO$_2$—NH—R$_3$ or —NHSO$_2$—R$_3$, where R$_3$ is selected from hydrogen, aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl.

6. The compound of claim 4, wherein

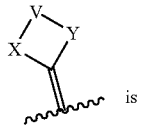 is 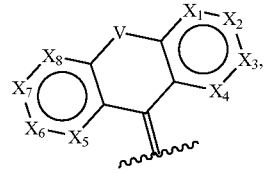

wherein X$_1$-X$_8$ are independently selected from CH and N and X$_1$-X$_8$ can be further substituted when it is a CH; V is a direct bond CO, O, S, NH, or (CH$_2$)$_q$, where q is 1, 2 or 3; A is —C(O)—O—R$_5$, where R$_5$ is —C$_3$-C$_{12}$ cycloalkyl or substituted —C$_3$-C$_{12}$ cycloalkyl; G is —NHSO$_2$—R$_3$, where R$_3$ is selected from —C$_3$-C$_{12}$ cycloalkyl and substituted —C$_3$-C$_{12}$ cycloalkyl.

7. The compound of claim 4, wherein

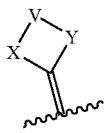

is

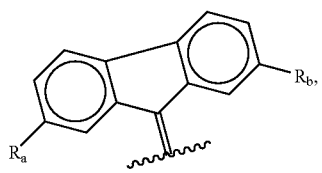

wherein Ra and Rb are each independently selected from hydrogen and halogen; A is —C(O)—O—R$_5$, where R$_5$ is —C$_3$-C$_{12}$ cycloalkyl or substituted —C$_3$-C$_{12}$ cycloalkyl; and G is —NHSO$_2$—R$_3$, where R$_3$ is selected from —C$_3$-C$_{12}$ cycloalkyl and substituted —C$_3$-C$_{12}$ cycloalkyl.

8. The compound according to claim 1 represented by formula V:

(V)

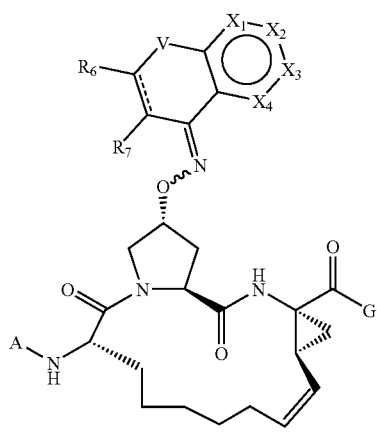

or a pharmaceutically acceptable salt thereof, where X$_1$-X$_4$ are independently selected from CO, CH, NH, O and N; where X$_1$-X$_4$ can be further substituted when any one of X$_1$-X$_4$ is CH or NH; where R$_6$ and R$_7$ are independently R$_3$.

9. The compound according to claim 1 represented by formula VI:

(VI)

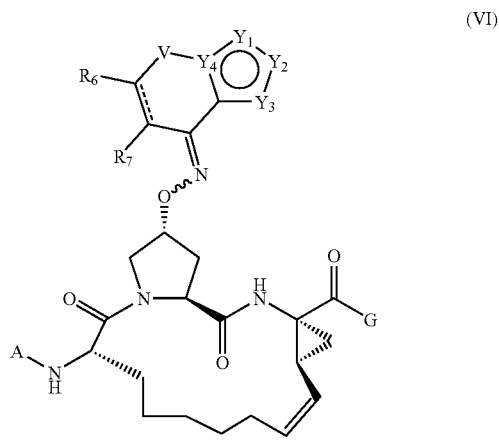

or a pharmaceutically acceptable salt, ester or prodrug thereof, where Y$_1$-Y$_3$ are independently selected from CO, CH, NH, N, S and O; and where Y$_1$-Y$_3$ can be further substituted when any one of Y$_1$-Y$_3$ is CH or NH; Y$_4$ is selected from C, CH and N.

10. The compound of claim 1 represented by formula VII:

(VII)

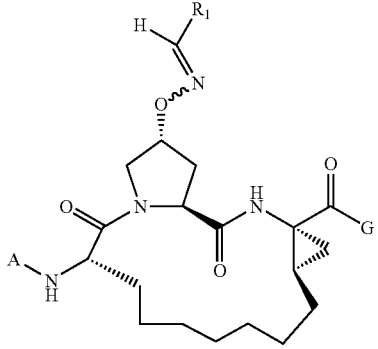

or a pharmaceutically acceptable salt thereof.

11. The compound of claim 1, represented by formula VIII:

(VIII)

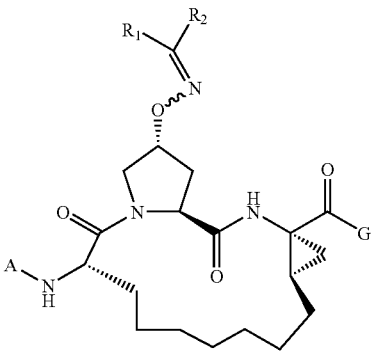

or a pharmaceutically acceptable salt thereof.

12. The compound according to claim 1 represented by formula IX:

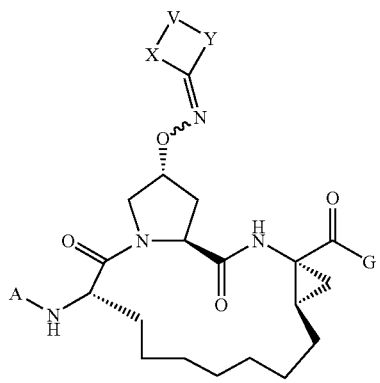

(IX)

or a pharmaceutically acceptable salt thereof, wherein V is a direct bond or V is CO, O, S, SO, SO$_2$, NH or NCH$_3$, or (CH$_2$)$_q$; where q is 1, 2, 3 or 4; and where X and Y are independently selected from the group consisting of: (i) aryl; substituted aryl; (ii) heteroaryl; substituted heteroaryl; and (iii) heterocyclic; substituted heterocyclic.

13. The compound of claim 12, wherein

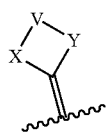

is selected from

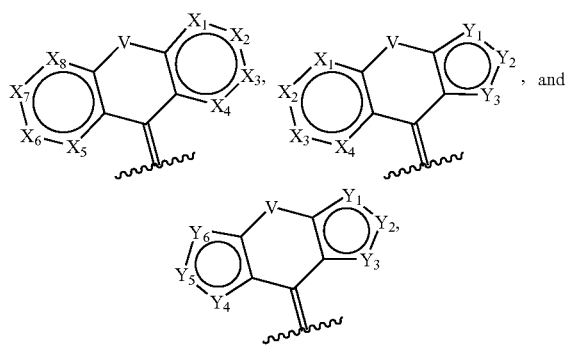

wherein X$_1$-X$_8$ are independently selected from CH and N and X$_1$-X$_8$ can be further substituted when it is a CH, and Y$_1$-Y$_3$ are independently selected from CH, N, NH, S and O and Y$_1$-Y$_3$ can be further substituted when it is CH or NH; V is a direct bond CO, O, S, NH, or (CH$_2$)$_q$, where q is 1, 2 or 3; A is —C(O)—O—R$_5$, where R$_5$ is —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl; G is —NHSO$_2$—R$_3$, where R$_3$ is selected from aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, and substituted —C$_3$-C$_{12}$ cycloalkenyl.

14. The compound of claim 12, wherein herein

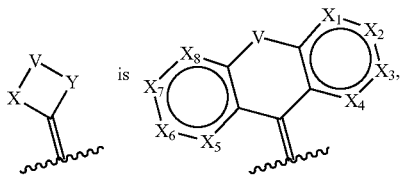

wherein X$_1$-X$_8$ are independently selected from CH and N and X$_1$-X$_8$ can be further substituted when it is a CH; V is a direct bond CO, O, S, NH, or (CH$_2$)$_q$, where q is 1, 2 or 3; A is —C(O)—O—R$_5$, where R$_5$ is —C$_3$-C$_{12}$ cycloalkyl or substituted —C$_3$-C$_{12}$ cycloalkyl; G is —NHSO$_2$—R$_3$, where R$_3$ is selected from —C$_3$-C$_{12}$ cycloalkyl and substituted —C$_3$-C$_{12}$ cycloalkyl.

15. The compound of claim 12, wherein

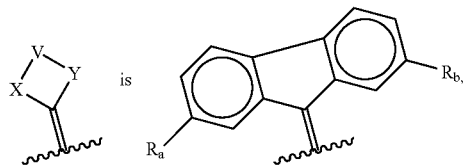

wherein Ra and Rb are each independently selected from hydrogen and halogen; A is —C(O)—O—R$_5$, where R$_5$ is —C$_3$-C$_{12}$ cycloalkyl or substituted —C$_3$-C$_{12}$ cycloalkyl; G is —NHSO$_2$—R$_3$, where R$_3$ is selected from —C$_3$-C$_{12}$ cycloalkyl and substituted —C$_3$-C$_{12}$ cycloalkyl.

16. The compound according to claim 1 represented by formula X:

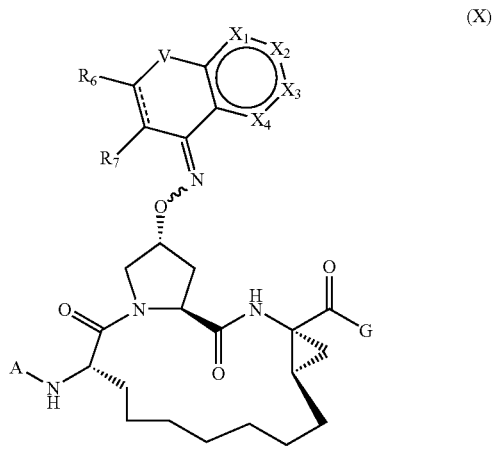

(X)

or a pharmaceutically acceptable salt thereof, where X$_1$-X$_4$ are independently selected from CO, CH, NH, O and N; and wherein X$_1$-X$_4$ can be further substituted when any one of X$_1$-X$_4$ is CH or NH; where R$_6$ and R$_7$ are independently R$_3$.

17. The compound according to claim 1 represented by formula XI:

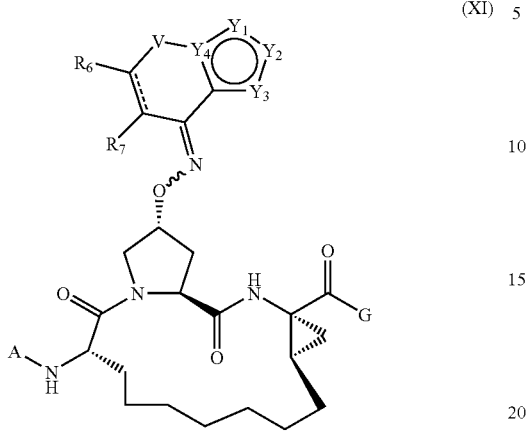

(XI)

or a pharmaceutically acceptable salt thereof, where $Y_1$-$Y_3$ are independently selected from CO, CH, NH, N, S and O; and where $Y_1$-$Y_3$ can be further substituted when any one of $Y_1$-$Y_3$ is CH or NH; $Y_4$ is selected from C, CH and N.

18. A compound of formula XII:

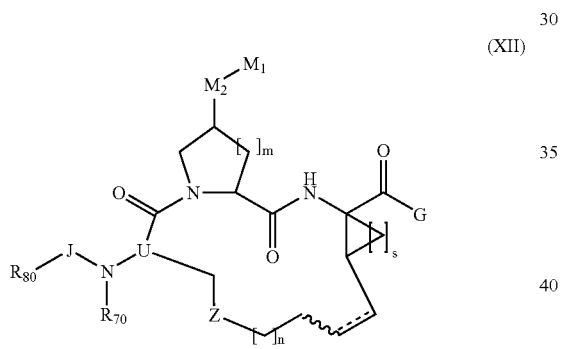

(XII)

or a pharmaceutically acceptable salt thereof, wherein:
$M_1$ is selected from the group consisting of:
(1) —N=$CR_{31}R_{32}$;
wherein $R_{31}$ and $R_{32}$ are independently selected from the group consisting of:
a) hydrogen;
b) aryl; substituted aryl;
c) heteroaryl; substituted heteroaryl;
d) —$C_1$-$C_8$ alkyl, —$C_2$-$C_8$ alkenyl, or —$C_2$-$C_8$ alkynyl containing 0, 1, 2, or 3 heteroatoms selected from O, S or N; optionally substituted with one or more substituents selected from halogen, aryl, substituted aryl, heteroaryl, or substituted heteroaryl;
e) —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic or substituted heterocyclic;
f) -A-$R_{30}$, where A is (CO), (CO)O, (CO)$NR_{40}$, (SO), ($SO_2$), ($SO_2$)$NR_{40}$; and $R_{30}$ and $R_{40}$ are independently selected from the group consisting of:
(i) Hydrogen;
(ii) aryl; substituted aryl; heteroaryl; substituted heteroaryl
(iii) —$C_1$-$C_8$ alkyl, —$C_2$-$C_8$ alkenyl, or —$C_2$-$C_8$ alkynyl containing 0, 1, 2, or 3 heteroatoms selected from O, S or N, optionally substituted with one or more substituents selected from halogen, aryl, substituted aryl, heteroaryl, or substituted heteroaryl; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic or substituted heterocyclic;

with added proviso that when A=CO, (CO)O, (SO), ($SO_2$), $R_{30}$ is not hydrogen; with added proviso that when $R_{31}$=hydrogen, $R_{32}$ is not hydrogen;

alternatively, $R_{31}$ and $R_{32}$ are taken together with the carbon atom to which they are attached to form the group consisting of:
a) —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl heterocyclic or substituted heterocyclic;
b) —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl; heterocyclic or substituted heterocyclic fused with one or more substituents selected from aryl, substituted aryl, heteroaryl, substituted heteroaryl, —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl; heterocyclic or substituted heterocyclic;
c)

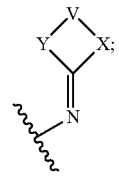

wherein V is a direct bond or V is O, S, SO, $SO_2$, $NR_{50}$, or $(CH_2)_q$; where $R_{50}$ is selected from H, OH, $OCH_3$, —O—$C_1$-$C_8$ alkyl, —$C_1$-$C_8$ alkyl, —O—$C_3$-$C_8$ cycloalkyl, —$C_3$-$C_8$ cycloalkyl, —O—$C_3$-$C_8$ cycloalkenyl; —$C_3$-$C_8$ cycloalkenyl; where q is 1, 2, 3 or 4; and
where X and Y are independently selected from the group consisting of:
(i) aryl; substituted aryl;
(ii) heteroaryl; substituted heteroaryl;
(iii) heterocyclic; substituted heterocyclic;
(2) $NR_{30}R_{40}$; $NR_5(CO)R_{30}$; $NR_{50}(CO)OR_{30}$; $NR_{50}$(CO)$NR_{30}R_{40}$; $NR_{50}(SO_2)OR_{30}$; $NR_{50}(SO_2)NR_{30}R_{40}$; where $R_{30}$, $R_{40}$ and $R_{50}$ are as previously defined; alternatively, for formula (I), $R_{30}$ and $R_{40}$ are taken together with the nitrogen atom to which they are attached to form the group consisting of: heterocyclic, or substituted heterocyclic; heteroaryl, or substituted heteroaryl;

$M_2$ is selected from the group consisting of:
(1) oxygen;
(2) sulfur;
(3) $NR_{60}$; where $R_{60}$ is selected from H, OH, $OCH_3$, —O—$C_1$-$C_8$ alkyl, —$C_1$-$C_5$ alkyl;

G is -E-$R_{30}$; and where E is absent, or E is O, CO, (CO)O, (CO)NH, NH, NH(CO), NH(CO)NH, NH($CNR_{50}$)NH, NH($SO_2$)NH or $NHSO_2$; where $R_{30}$ and $R_{50}$ are as previously defined;

Z is selected from the group consisting of $CH_2$, O, CO, (CO)O, (CO)NH, S, SO, $SO_2$, CF, $CF_2$, aryl, substituted aryl, heteroaryl and substituted heteroaryl;

n=0, 1, 2, 3 or 4;

U is CH, CF or N;

$R_{70}$ is selected from the group consisting of H, OH, $OCH_3$, —O—$C_1$-$C_8$ alkyl, —$C_1$-$C_8$ alkyl;

J is selected from the group consisting of CO, (CO)O, (CO)NR$_{50}$, $SO_2$, ($SO_2$)O or $SO_2NR_{50}$;

$R_{80}$ is selected from the group consisting of:
(1) hydrogen;
(2) aryl; substituted aryl; heteroaryl; substituted heteroaryl;
(3) —$C_1$-$C_8$ alkyl, —$C_2$-$C_8$ alkenyl, or —$C_2$-$C_8$ alkynyl containing 0, 1, 2, or 3 heteroatoms selected from O, S or N, optionally substituted with one or more substituents selected from halogen, aryl, substituted aryl, heteroaryl, or substituted heteroaryl; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic or substituted heterocyclic;

with added proviso that when J=CO, (CO)O, (SO) or ($SO_2$), $R_{80}$ is not hydrogen;

m=0, 1, 2 or 3; and s=0, 1, 2 or 3.

19. A compound of formula XX:

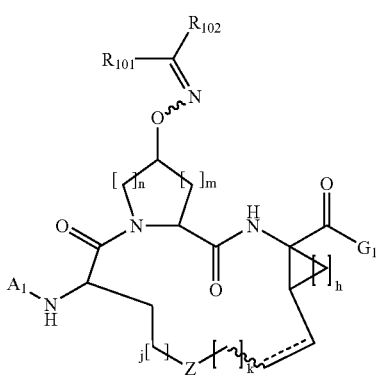

(XX)

or a pharmaceutically acceptable salt thereof, wherein:

$R_{101}$ and $R_{102}$ are independently selected from the group consisting of:
a) hydrogen;
b) aryl;
c) substituted aryl;
d) heteroaryl fused with 0, 1, 2, or 3 more group selected from heteroaryl and aryl;
e) substituted heteroaryl fused with 0, 1, 2 or 3 more group selected from heteroaryl, substituted heteroaryl, aryl and substituted aryl;
f) heterocyclic, substituted heterocyclic, or oxo substituted heterocyclic; wherein oxo refer to substituted by independent replacement of two of the hydrogen atoms thereon with =O;
g) —$C_1$-$C_8$ alkyl, —$C_2$-$C_8$ alkenyl, or —$C_2$-$C_8$ alkynyl each containing 0, 1, 2, or 3 heteroatoms selected from O, S or N;
h) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
i) —$C_3$-$C_{12}$ cycloalkyl, or —$C_3$-$C_{12}$ cycloalkenyl;
j) substituted —$C_3$-$C_{12}$ cycloalkyl, or substituted —$C_3$-$C_{12}$ cycloalkenyl;
k) oxo substituted —$C_3$-$C_{12}$ cycloalkyl, or oxo substituted —$C_3$-$C_{12}$ cycloalkenyl;
l) -B-$R_{103}$, where B is (CO), (CO)O, (CO)NR$_{104}$, (SO), ($SO_2$), ($SO_2$)NR$_{104}$; and $R_{103}$ and $R_{104}$ are independently selected from the group consisting of:
(i) hydrogen;
(ii) aryl;
(iii) substituted aryl;
(iv) heteroaryl fused with 0, 1, 2, or 3 more group selected from aryl and heteroaryl;
(v) substituted heteroaryl fused with 0, 1, 2 or 3 more group selected from heteroaryl, substituted heteroaryl, aryl and substituted aryl;
(vi) heterocyclic;
(vii) substituted heterocyclic;
(viii) oxo substituted heterocyclic;
(ix) —$C_1$-$C_8$ alkyl, —$C_2$-$C_8$ alkenyl, or —$C_2$-$C_8$ alkynyl each containing 0, 1, 2, or 3 heteroatoms selected from O, S or N;
(x) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
(xi) —$C_3$-$C_{12}$ cycloalkyl, or —$C_3$-$C_{12}$ cycloalkenyl;
(xii) substituted —$C_3$-$C_{12}$ cycloalkyl, substituted —$C_3$-$C_{12}$ cycloalkenyl, oxo substituted —$C_3$-$C_{12}$ cycloalkyl, or oxo substituted —$C_3$-$C_{12}$ cycloalkenyl;

or $R_{101}$ and $R_{102}$ taken together with the carbon atom to which they are attached form a cyclic moiety selected from: substituted or unsubstituted cycloalkyl, cycloalkenyl, or heterocyclic; substituted or unsubstituted cycloalkyl, cycloalkenyl, or heterocyclic each substituted with an oxo; substituted or unsubstituted cycloalkyl, cycloalkenyl, or heterocyclic each fused with one or more $R_{103}$; or oxo substituted or unsubstituted cycloalkyl, cycloalkenyl, or heterocyclic each fused with one or more $R_{103}$;

$G_1$ is -E-$R_{103}$, where E is absent or E is O, CO, (CO)O, (CO)NH, NH, NH(CO), NH(CO)NH, NH($SO_2$)NH or $NHSO_2$;

Z is selected from the group consisting of $CH_2$, O, S, SO, or $SO_2$;

A is selected from the group consisting of $R_{105}$, (CO)$R_{105}$, (CO)O$R_{105}$, (CO)NHR$_{105}$, $SO_2R_{105}$, ($SO_2$)OR$_{105}$ and $SO_2NHR_{105}$;

$R_{105}$ is selected from the group consisting of: aryl;
a) hydrogen
b) substituted aryl;
c) heteroaryl fused with 0, 1, 2, or 3 more group selected from heteroaryl and aryl;
d) substituted heteroaryl fused with 0, 1, 2 or 3 more group selected from heteroaryl, substituted heteroaryl, aryl and substituted aryl;
e) heterocyclic;
f) substituted heterocyclic;
g) oxo substituted heterocyclic;
h) —$C_1$-$C_8$ alkyl, —$C_2$-$C_8$ alkenyl, or —$C_2$-$C_8$ alkynyl each containing 0, 1, 2, or 3 heteroatoms selected from O, S or N;
i) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
j) —$C_3$-$C_{12}$ cycloalkyl, or —$C_3$-$C_{12}$ cycloalkenyl;
k) substituted —$C_3$-$C_{12}$ cycloalkyl, substituted —$C_3$-$C_{12}$ cycloalkenyl, oxo substituted —$C_3$-$C_{12}$ cycloalkyl, or oxo substituted —$C_3$-$C_{12}$ cycloalkenyl;

j=0, 1, 2, or 3;
k=0, 1, 2, or 3;
m=0, 1, 2 or 3;
n=1, 2 or 3 and
h=0, 1, 2, or 3.
20. A compound having the Formula A selected from compounds 1-2 of Table 1:
TABLE 1
(A)
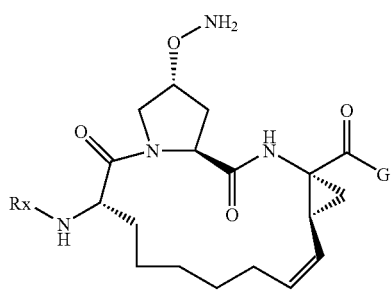
| Compound | Rx | G |
|---|---|---|
| (1) | 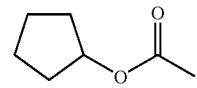 | OEt |
| (2) | 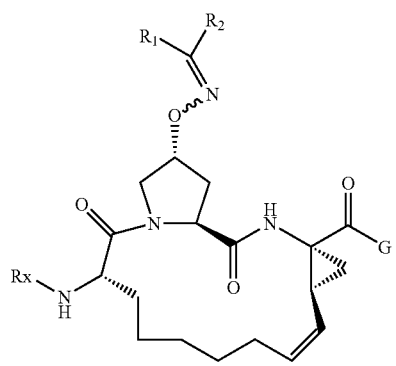 | OEt. |
21. The compound of claim 1 having the Formula B selected from compounds 3-115 of Table 2:
TABLE 2
(B)
| Compound | Rx | $R_1$ | $R_2$ | G |
|---|---|---|---|---|
| (3) | cyclopentyl ester | —CH$_3$ | —Ph | —OH |
| (4) | cyclopentyl ester | —CH$_2$CH$_3$ | —Ph | —OH |
| (5) | cyclopentyl ester | —CH$_2$CH$_2$CH$_3$ | —Ph | —OH |

TABLE 2-continued
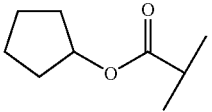
(B)
| Compound | Rx | R₁ | R₂ | G |
|---|---|---|---|---|
| (6) | 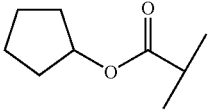 | —CH₂OCH₃ | —Ph | —OH |
| (7) | 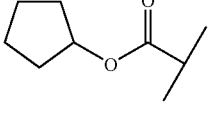 | —Ph | —Ph | —OH |
| (8) | 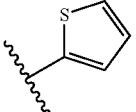 | —Ph | 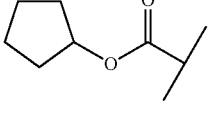 | —OH |
| (9) |  | 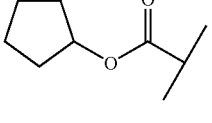 | —Ph | —OH |
| (10) |  | 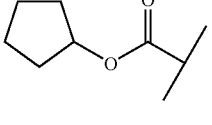 | —Ph | —OH |
| (11) | 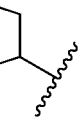 | 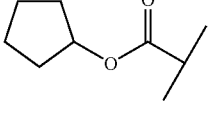 | —Ph | —OH |
| (12) | 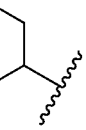 | 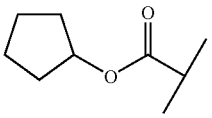 | —Ph | —OH |
| (13) |  | —H | —Ph | —OH |

TABLE 2-continued (B)

| Compound | Rx | R₁ | R₂ | G |
|---|---|---|---|---|
| (14) | cyclopentyl-O-C(=O)-CH(CH₃)- | —H | 2-biphenyl | —OH |
| (15) | cyclopentyl-O-C(=O)-CH(CH₃)- | —H | 3-biphenyl | —OH |
| (16) | cyclopentyl-O-C(=O)-CH(CH₃)- | —H | 4-biphenyl | —OH |
| (17) | cyclopentyl-O-C(=O)-CH(CH₃)- | —H | 1-naphthyl | —OH |
| (18) | cyclopentyl-O-C(=O)-CH(CH₃)- | —H | 2-naphthyl | —OH |
| (19) | cyclopentyl-O-C(=O)-CH(CH₃)- | —CH₂CH₃ | 2-biphenyl | —OH |

TABLE 2-continued
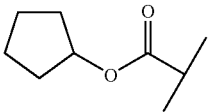
(B)
| Compound | Rx | R₁ | R₂ | G |
|---|---|---|---|---|
| (20) | 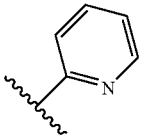 | —H | 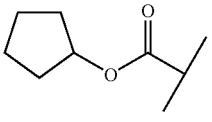 | —OH |
| (21) | 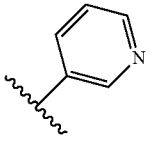 [SMILES: *c1cccnc1] | —H | 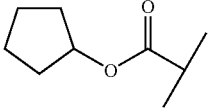 | —OH |
| (22) | 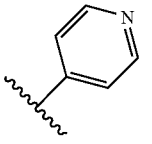 [SMILES: *c1ccncc1] | —H | 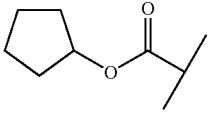 | —OH |
| (23) | 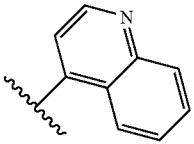 | —H | 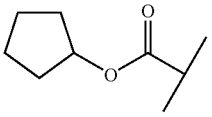 | —OH |
| (24) | 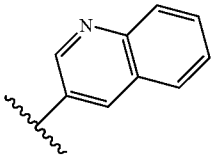 [SMILES: *c1cnc2ccccc2c1] | —H | 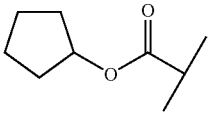 | —OH |
| (25) | 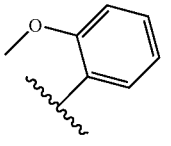 [SMILES: *c1ccccc1OC] | —H | 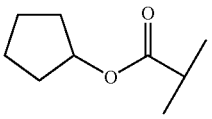 | —OH |
| (26) | 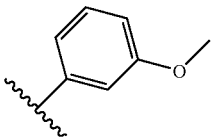 [SMILES: *c1cccc(OC)c1] | —H | | —OH |

TABLE 2-continued (B)

| Compound | Rx | R₁ | R₂ | G |
|---|---|---|---|---|
| (27) | cyclopentyl-O-C(O)-CH(CH₃)- | —H | 4-methoxyphenyl | —OH |
| (28) | cyclopentyl-O-C(O)-CH(CH₃)- | —H | 2-fluorophenyl | —OH |
| (29) | cyclopentyl-O-C(O)-CH(CH₃)- | —H | 3-fluorophenyl | —OH |
| (30) | cyclopentyl-O-C(O)-CH(CH₃)- | —H | 4-fluorophenyl | —OH |
| (31) | cyclopentyl-O-C(O)-CH(CH₃)- | —H | 2-(thiophen-2-yl)phenyl | —OH |
| (32) | cyclopentyl-O-C(O)-CH(CH₃)- | —H | 2-(1H-pyrazol-1-yl)phenyl | —OH |
| (33) | cyclopentyl-O-C(O)-CH(CH₃)- | —H | 2-(1H-1,2,4-triazol-1-yl)phenyl | —OH |

TABLE 2-continued (B)

| Compound | Rx | R₁ | R₂ | G |
|---|---|---|---|---|
| (34) | cyclopentyl-O-C(=O)-CH(CH₃)- | —H | 2-(thiazol-2-yl)phenyl | —OH |
| (35) | cyclopentyl-O-C(=O)-CH(CH₃)- | —H | 2-(imidazol-1-yl)phenyl | —OH |
| (36) | cyclopentyl-O-C(=O)-CH(CH₃)- | —H | 2-(thiophen-2-yl)-4-methoxyphenyl | —OH |
| (37) | cyclopentyl-O-C(=O)-CH(CH₃)- | —H | 2-(thiazol-2-yl)-4-methoxyphenyl | —OH |
| (38) | cyclopentyl-O-C(=O)-CH(CH₃)- | —H | 2-(thiophen-2-yl)-4-methoxyphenyl | cyclopropylsulfonylaminocarbonyl |
| (39) | cyclopentyl-O-C(=O)-CH(CH₃)- | —H | 2'-isopropylbiphenyl-2-yl | cyclopropylsulfonylaminocarbonyl |

TABLE 2-continued (B)

| Compound | Rx | R₁ | R₂ | G |
|---|---|---|---|---|
| (40) | cyclopentyl-O-C(O)-CH(CH₃)- | —H | 2-(2-isopropylphenyl)thiophene | —NHS(O)₂-cyclopropyl |
| (41) | cyclopentyl-O-C(O)-CH(CH₃)- | —H | 5-(2-isopropyl-4-methoxyphenyl)isoxazole | —OH |
| (42) | cyclopentyl-O-C(O)-CH(CH₃)- | —H | 5-(2-isopropyl-4-methoxyphenyl)isoxazole | —NHS(O)₂-cyclopropyl |
| (43) | tert-butyl-O-C(O)-CH(CH₃)- | —Ph | —Ph | —OH |
| (44) | tert-butyl-O-C(O)-CH(CH₃)- | —CH₃ | —Ph | —OH |
| (45) | tert-butyl-O-C(O)-CH(CH₃)- | —H | —Ph | —OH |
| (46) | cyclopentyl-O-C(O)-CH(CH₃)- | —CH₃ | —Ph | —NHS(O)₂-cyclopropyl |
| (47) | cyclopentyl-O-C(O)-CH(CH₃)- | —CH₂CH₃ | —Ph | —NHS(O)₂-cyclopropyl |

TABLE 2-continued
(B)
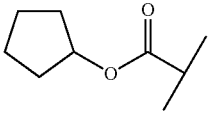
| Compound | Rx | R₁ | R₂ | G |
|---|---|---|---|---|
| (48) | 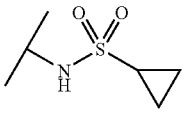 | —CH₂CH₂CH₃ | —Ph | 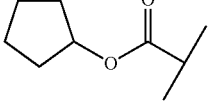 |
| (49) | 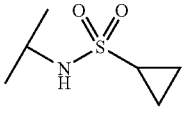 | —CH₂OCH₃ | —Ph | 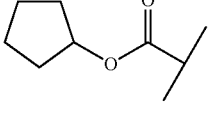 |
| (50) | 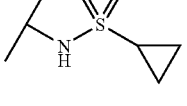 | —Ph | —Ph | 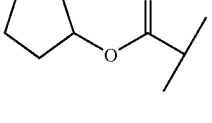 |
| (51) | 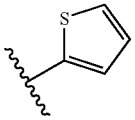 [SMILES: *c1cccs1] | —Ph | 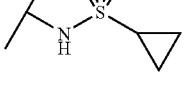 | 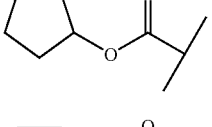 |
| (52) | 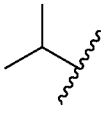 [SMILES: *C(C)C] | 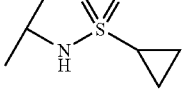 | —Ph | 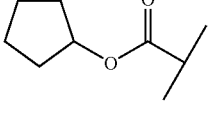 |
| (53) | 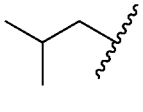 | 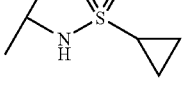 | —Ph | 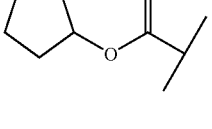 |
| (54) | 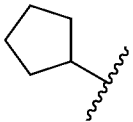 | 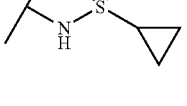 | —Ph | 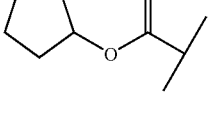 |
| (55) | 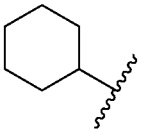 [SMILES: *C1CCCCC1] | 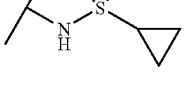 | —Ph | 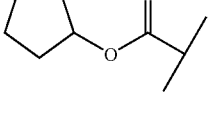 |
| (56) | 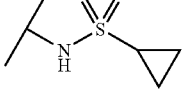 | —H | —Ph | |

TABLE 2-continued (B)

| Compound | Rx | R₁ | R₂ | G |
|---|---|---|---|---|
| (57) | cyclopentyl-O-C(O)-CH(CH₃)- | —H | 3-biphenyl | -C(CH₃)-NH-S(O)₂-cyclopropyl |
| (58) | cyclopentyl-O-C(O)-CH(CH₃)- | —H | 4-biphenyl | -C(CH₃)-NH-S(O)₂-cyclopropyl |
| (59) | cyclopentyl-O-C(O)-CH(CH₃)- | —H | 1-naphthyl | -C(CH₃)-NH-S(O)₂-cyclopropyl |
| (60) | cyclopentyl-O-C(O)-CH(CH₃)- | —H | 2-naphthyl | -C(CH₃)-NH-S(O)₂-cyclopropyl |
| (61) | cyclopentyl-O-C(O)-CH(CH₃)- | —CH₂CH₃ | 2-biphenyl | -C(CH₃)-NH-S(O)₂-cyclopropyl |
| (62) | cyclopentyl-O-C(O)-CH(CH₃)- | —H | 2-pyridyl | -C(CH₃)-NH-S(O)₂-cyclopropyl |
| (63) | cyclopentyl-O-C(O)-CH(CH₃)- | —H | 3-pyridyl | -C(CH₃)-NH-S(O)₂-cyclopropyl |

TABLE 2-continued (B)

| Compound | Rx | R₁ | R₂ | G |
|---|---|---|---|---|
| (64) | cyclopentyl-O-C(O)-CH(CH₃)- | —H | 4-pyridyl | -C(cyclopropyl)(H)-NH-S(O)₂-cyclopropyl |
| (65) | cyclopentyl-O-C(O)-CH(CH₃)- | —H | 4-quinolinyl | -C(cyclopropyl)(H)-NH-S(O)₂-cyclopropyl |
| (66) | cyclopentyl-O-C(O)-CH(CH₃)- | —H | 3-quinolinyl | -C(cyclopropyl)(H)-NH-S(O)₂-cyclopropyl |
| (67) | cyclopentyl-O-C(O)-CH(CH₃)- | —H | 2-methoxyphenyl | -C(cyclopropyl)(H)-NH-S(O)₂-cyclopropyl |
| (68) | cyclopentyl-O-C(O)-CH(CH₃)- | —H | 3-methoxyphenyl | -C(cyclopropyl)(H)-NH-S(O)₂-cyclopropyl |
| (69) | cyclopentyl-O-C(O)-CH(CH₃)- | —H | 4-methoxyphenyl | -C(cyclopropyl)(H)-NH-S(O)₂-cyclopropyl |
| (70) | cyclopentyl-O-C(O)-CH(CH₃)- | —H | 2-fluorophenyl | -C(cyclopropyl)(H)-NH-S(O)₂-cyclopropyl |

TABLE 2-continued (B)

| Compound | Rx | R₁ | R₂ | G |
|---|---|---|---|---|
| (71) | cyclopentyl-O-C(O)-CH(CH₃)- | —H | 3-fluorophenyl | -NHS(O)₂-cyclopropyl |
| (72) | cyclopentyl-O-C(O)-CH(CH₃)- | —H | 4-fluorophenyl | -NHS(O)₂-cyclopropyl |
| (73) | cyclopentyl-O-C(O)-CH(CH₃)- | —H | 2-(pyrazol-1-yl)phenyl | -NHS(O)₂-cyclopropyl |
| (74) | cyclopentyl-O-C(O)-CH(CH₃)- | —H | 2-(1,2,4-triazol-1-yl)phenyl | -NHS(O)₂-cyclopropyl |
| (75) | cyclopentyl-O-C(O)-CH(CH₃)- | —H | 2-(thiazol-2-yl)phenyl | -NHS(O)₂-cyclopropyl |
| (76) | cyclopentyl-O-C(O)-CH(CH₃)- | —H | 2-(imidazol-1-yl)phenyl | -NHS(O)₂-cyclopropyl |
| (77) | cyclopentyl-O-C(O)-CH(CH₃)- | —H | 2-(thiazol-2-yl)-4-methoxyphenyl | -NHS(O)₂-cyclopropyl |

TABLE 2-continued (B)

| Compound | Rx | R₁ | R₂ | G |
|---|---|---|---|---|
| (78) | cyclopentyl-O-C(=O)-CH(CH₃)- | —Ph | —Ph | —NH-S(=O)₂-cyclopropyl |
| (79) | cyclopentyl-O-C(=O)-CH(CH₃)- | —CH₃ | —Ph | —NH-S(=O)₂-cyclopropyl |
| (80) | cyclopentyl-O-C(=O)-CH(CH₃)- | —H | —Ph | —NH-S(=O)₂-cyclopropyl |
| (81) | cyclobutyl-O-C(=O)-CH(CH₃)- | —CH₃ | —Ph | —NH-S(=O)₂-cyclopropyl |
| (82) | cyclobutyl-O-C(=O)-CH(CH₃)- | —CH₂CH₃ | —Ph | —NH-S(=O)₂-cyclopropyl |
| (83) | cyclobutyl-O-C(=O)-CH(CH₃)- | —CH₂CH₂CH₃ | —Ph | —NH-S(=O)₂-cyclopropyl |
| (84) | cyclobutyl-O-C(=O)-CH(CH₃)- | —CH₂OCH₃ | —Ph | —NH-S(=O)₂-cyclopropyl |
| (85) | cyclobutyl-O-C(=O)-CH(CH₃)- | —Ph | —Ph | —NH-S(=O)₂-cyclopropyl |
| (86) | cyclobutyl-O-C(=O)-CH(CH₃)- | —Ph | 2-thienyl | —NH-S(=O)₂-cyclopropyl |

TABLE 2-continued (B)

| Compound | Rx | R₁ | R₂ | G |
|---|---|---|---|---|
| (87) | cyclobutyl-O-C(O)-CH(CH₃)- | isopropyl | —Ph | —NH-S(O)₂-cyclopropyl |
| (88) | cyclobutyl-O-C(O)-CH(CH₃)- | isobutyl | —Ph | —NH-S(O)₂-cyclopropyl |
| (89) | cyclobutyl-O-C(O)-CH(CH₃)- | cyclopentyl | —Ph | —NH-S(O)₂-cyclopropyl |
| (90) | cyclobutyl-O-C(O)-CH(CH₃)- | cyclohexyl | —Ph | —NH-S(O)₂-cyclopropyl |
| (91) | cyclobutyl-O-C(O)-CH(CH₃)- | —H | —Ph | —NH-S(O)₂-cyclopropyl |
| (92) | cyclobutyl-O-C(O)-CH(CH₃)- | —H | 2-biphenyl | —NH-S(O)₂-cyclopropyl |
| (93) | cyclobutyl-O-C(O)-CH(CH₃)- | —H | 3-biphenyl | —NH-S(O)₂-cyclopropyl |

TABLE 2-continued (B)

| Compound | Rx | R₁ | R₂ | G |
|---|---|---|---|---|
| (94) | cyclobutyl-O-C(=O)-CH(CH₃)- | —H | biphenyl-4-yl | -CH(iPr)-NH-S(=O)₂-cyclopropyl |
| (95) | cyclobutyl-O-C(=O)-CH(CH₃)- | —H | naphthalen-1-yl | -CH(iPr)-NH-S(=O)₂-cyclopropyl |
| (96) | cyclobutyl-O-C(=O)-CH(CH₃)- | —H | naphthalen-2-yl | -CH(iPr)-NH-S(=O)₂-cyclopropyl |
| (97) | cyclobutyl-O-C(=O)-CH(CH₃)- | —CH₂CH₃ | biphenyl-2-yl | -CH(iPr)-NH-S(=O)₂-cyclopropyl |
| (98) | cyclobutyl-O-C(=O)-CH(CH₃)- | —H | pyridin-2-yl | -CH(iPr)-NH-S(=O)₂-cyclopropyl |
| (99) | cyclobutyl-O-C(=O)-CH(CH₃)- | —H | pyridin-3-yl | -CH(iPr)-NH-S(=O)₂-cyclopropyl |

TABLE 2-continued (B)

| Compound | Rx | R₁ | R₂ | G |
|---|---|---|---|---|
| (100) | cyclobutyl-O-C(=O)-CH(CH₃)- | —H | pyridin-4-yl | -C(cyclopropyl)-NH-S(=O)₂-cyclopropyl |
| (101) | cyclobutyl-O-C(=O)-CH(CH₃)- | —H | quinolin-4-yl | -C(cyclopropyl)-NH-S(=O)₂-cyclopropyl |
| (102) | cyclobutyl-O-C(=O)-CH(CH₃)- | —H | quinolin-3-yl | -C(cyclopropyl)-NH-S(=O)₂-cyclopropyl |
| (103) | cyclobutyl-O-C(=O)-CH(CH₃)- | —H | 2-methoxyphenyl | -C(cyclopropyl)-NH-S(=O)₂-cyclopropyl |
| (104) | cyclobutyl-O-C(=O)-CH(CH₃)- | —H | 3-methoxyphenyl | -C(cyclopropyl)-NH-S(=O)₂-cyclopropyl |
| (105) | cyclobutyl-O-C(=O)-CH(CH₃)- | —H | 4-methoxyphenyl | -C(cyclopropyl)-NH-S(=O)₂-cyclopropyl |
| (106) | cyclobutyl-O-C(=O)-CH(CH₃)- | —H | 2-fluorophenyl | -C(cyclopropyl)-NH-S(=O)₂-cyclopropyl |

TABLE 2-continued (B)

| Compound | Rx | R₁ | R₂ | G |
|---|---|---|---|---|
| (107) | cyclobutyl-O-C(O)-CH(CH₃)- | —H | 3-fluorophenyl | -CH(CH₃)-NH-S(O)₂-cyclopropyl |
| (108) | cyclobutyl-O-C(O)-CH(CH₃)- | —H | 4-fluorophenyl | -CH(CH₃)-NH-S(O)₂-cyclopropyl |
| (109) | cyclobutyl-O-C(O)-CH(CH₃)- | —H | 2-(thiophen-2-yl)phenyl | -CH(CH₃)-NH-S(O)₂-cyclopropyl |
| (110) | cyclobutyl-O-C(O)-CH(CH₃)- | —H | 2-(pyrazol-1-yl)phenyl | -CH(CH₃)-NH-S(O)₂-cyclopropyl |
| (111) | cyclobutyl-O-C(O)-CH(CH₃)- | —H | 2-(1,2,4-triazol-1-yl)phenyl | -CH(CH₃)-NH-S(O)₂-cyclopropyl |
| (112) | cyclobutyl-O-C(O)-CH(CH₃)- | —H | 2-(thiazol-2-yl)phenyl | -CH(CH₃)-NH-S(O)₂-cyclopropyl |

TABLE 2-continued (B)

| Compound | Rx | R₁ | R₂ | G |
|---|---|---|---|---|
| (113) | cyclobutyl-O-C(=O)-CH(CH₃)- | —H | 1-phenyl-imidazol-2-yl (attached via phenyl ortho) | cyclopropylsulfonyl-NH-C(cyclopropyl)- |
| (114) | cyclobutyl-O-C(=O)-CH(CH₃)- | —H | 2-(thiophen-2-yl)-4-methoxyphenyl | cyclopropylsulfonyl-NH-C(cyclopropyl)- |
| (115) | cyclobutyl-O-C(=O)-CH(CH₃)- | —H | 2-(thiazol-2-yl)-4-methoxyphenyl | cyclopropylsulfonyl-NH-C(cyclopropyl)- | or a pharmaceutically acceptable salt thereof.

22. A compound having the Formula B,

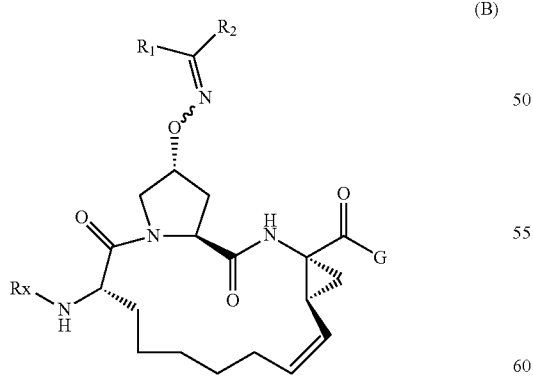

(B)

wherein $R_1$ and $R_2$ are taken together with the carbon to which they are attached to form $R_1R_2$, selected from compounds 116-204 of Table 3:

TABLE 3
| Compound | Rx | R₁R₂ | G |
|---|---|---|---|
| (116) | 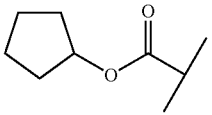 | 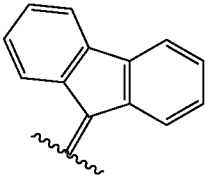 [SMILES: *=C1c2ccccc2-c2ccccc21] | —OH |
| (117) | 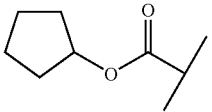 | 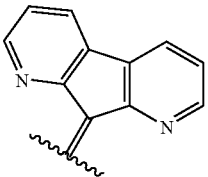 [SMILES: *=C1c2ncccc2-c2cccnc21] | —OH |
| (118) | 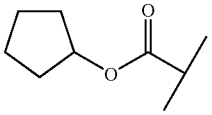 | 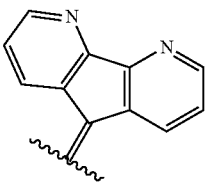 [SMILES: *=C1c2cccnc2-c2ncccc21] | —OH |
| (119) | 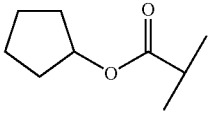 | 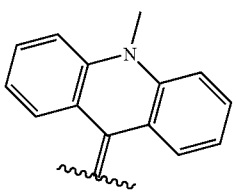 [SMILES: *=C1c2ccccc2N(C)c2ccccc21] | —OH |
| (120) | 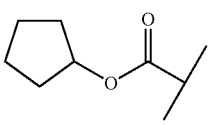 | 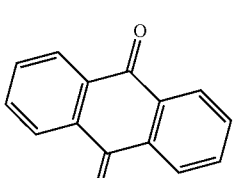 | —OH |
| (121) | 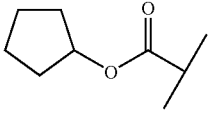 | 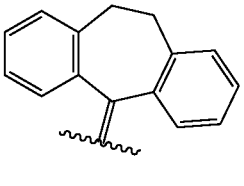 [SMILES: *=C1c2ccccc2CCc2ccccc21] | —OH |
| (122) | 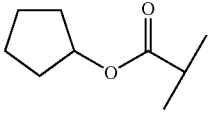 | 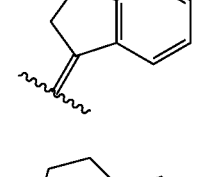 | —OH |
| (123) | 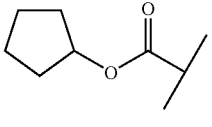 | 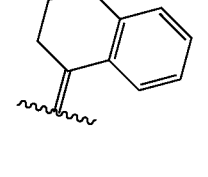 | —OH |

TABLE 3-continued
| Compound | Rx | R₁R₂ | G |
|---|---|---|---|
| (124) | 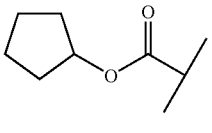 | 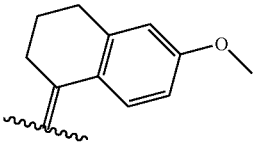 [SMILES: *=C1CCCc2cc(OC)ccc21] | —OH |
| (125) | 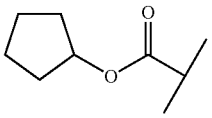 | 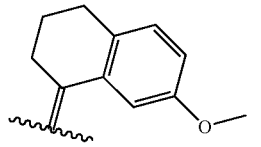 [SMILES: *=C1CCCc2ccc(OC)cc21] | —OH |
| (126) | 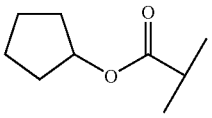 | 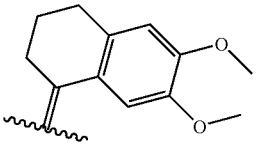 [SMILES: *=C1CCCc2cc(OC)c(OC)cc21] | —OH |
| (127) | 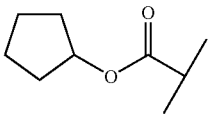 | 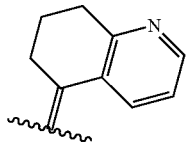 [SMILES: *=C1CCCc2ncccc21] | —OH |
| (128) | 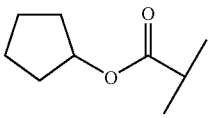 | 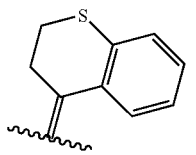 | —OH |
| (129) | 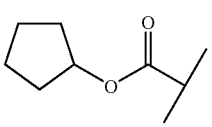 | 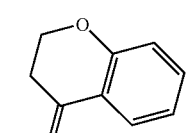 | —OH |
| (130) | 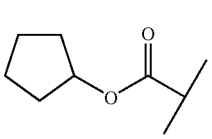 | 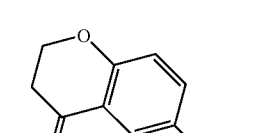 | —OH |
| (131) | 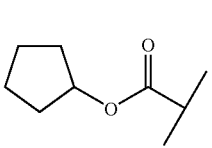 | 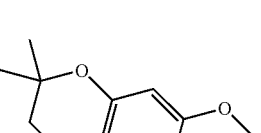 | —OH |
| (132) | 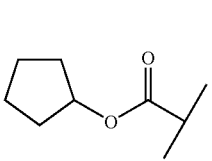 | 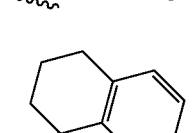 | —OH |

TABLE 3-continued

| Compound | Rx | R₁R₂ | G |
|---|---|---|---|
| (133) | cyclopentyl ester | tetrahydronaphthalene with thiophene | —OH |
| (134) | cyclopentyl ester | fluorene | cyclopropanesulfonamide |
| (135) | tert-butyl ester | indane | —OH |
| (136) | tert-butyl ester | tetrahydronaphthalene | —OH |
| (137) | cyclopentyl ester | diazafluorene | cyclopropanesulfonamide |
| (138) | cyclopentyl ester | fluorene | tetrazole-NH |
| (139) | tert-butyl ester | xanthene with ethylidene | —OH |
| (140) | tert-butyl ester | xanthene with ethylidene | cyclopropanesulfonamide |

TABLE 3-continued

| Compound | Rx | R₁R₂ | G |
|---|---|---|---|
| (141) | cyclopentyl isobutyrate ester | xanthene with ethylidene | cyclopropanesulfonamide |
| (142) | tert-butyl isobutyrate ester | 2-phenyl-4-ethylidene-4H-chromene | —OH |
| (143) | tert-butyl isobutyrate ester | 2-phenyl-4-ethylidene-4H-chromene | cyclopropanesulfonamide |
| (144) | cyclopentyl isobutyrate ester | 2-phenyl-4-ethylidene-4H-chromene | cyclopropanesulfonamide |
| (145) | tert-butyl isobutyrate ester | 3-phenyl-4-ethylidene-4H-chromene | —OH |
| (146) | tert-butyl isobutyrate ester | 3-phenyl-4-ethylidene-4H-chromene | cyclopropanesulfonamide |
| (147) | cyclopentyl isobutyrate ester | 6-fluoro-4-ethylidene-chromane | —OH |
| (148) | cyclopentyl isobutyrate ester | 6-fluoro-4-ethylidene-chromane | cyclopropanesulfonamide |

TABLE 3-continued
| Compound | Rx | R₁R₂ | G |
|---|---|---|---|
| (149) | 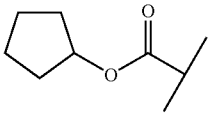 | 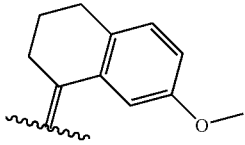 [SMILES: *=C1CCCc2ccc(OC)cc21] | 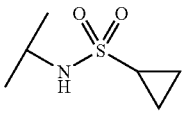 |
| (150) | 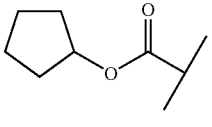 | 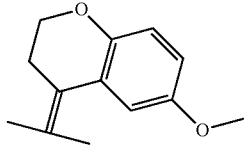 | 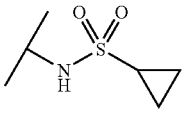 |
| (151) | 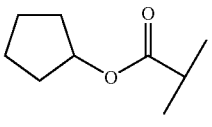 | 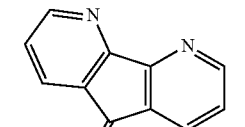 | 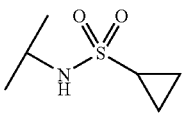 |
| (152) | 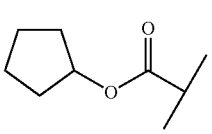 | 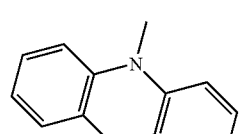 | 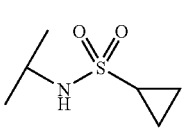 |
| (153) | 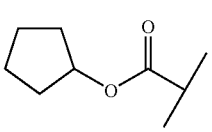 | 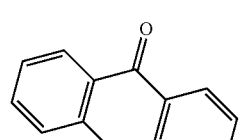 | 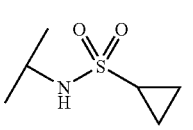 |
| (154) | 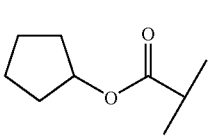 | 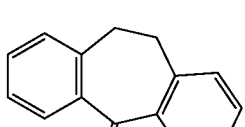 | 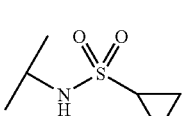 |
| (155) | 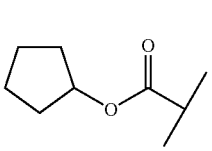 | 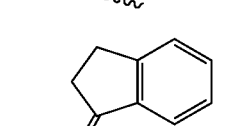 | 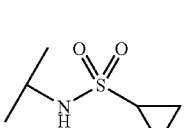 |
| (156) | 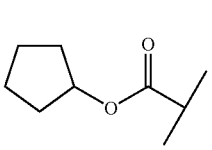 | 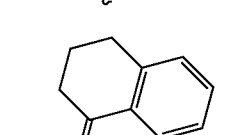 | 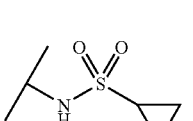 |
| (157) | 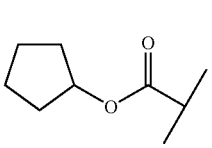 | 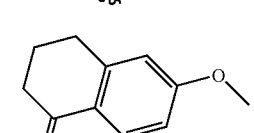 | 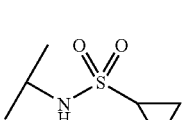 |

TABLE 3-continued

| Compound | Rx | R₁R₂ | G |
|---|---|---|---|
| (158) | | | |
| (159) | | | |
| (160) | | | |
| (161) | | | |
| (162) | | | |
| (163) | | | |
| (164) | | | |
| (165) | | | |
| (166) | | | |

TABLE 3-continued

| Compound | Rx | R₁R₂ | G |
|---|---|---|---|
| (167) | | | |
| (168) | | | |
| (169) | | | |
| (170) | | | |
| (171) | | | |
| (172) | | | |
| (173) | | | |
| (174) | | | |
| (175) | | | |

TABLE 3-continued

| Compound | Rx | R₁R₂ | G |
|---|---|---|---|
| (176) | | | |
| (177) | | | |
| (178) | | | |
| (179) | | | |
| (180) | | | |
| (181) | | | |
| (182) | | | |
| (183) | | | |

TABLE 3-continued

| Compound | Rx | R₁R₂ | G |
|---|---|---|---|
| (184) | | | |
| (185) | | | |
| (186) | | | |
| (187) | | | |
| (188) | | | |
| (189) | | | |
| (190) | | | |
| (191) | | | |
| (192) | | | |

US 9,526,769 B2
233                                                                                                                     234
TABLE 3-continued
| Compound | Rx | R₁R₂ | G |
|---|---|---|---|
| (193) | 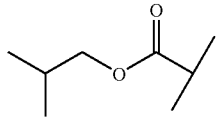 | 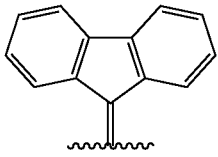 [SMILES: *=C1c2ccccc2-c2ccccc21] | 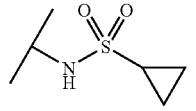 |
| (194) | 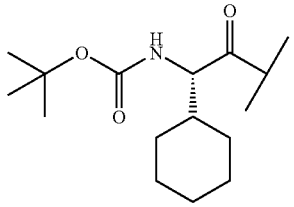 | 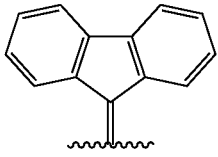 [SMILES: *=C1c2ccccc2-c2ccccc21] | 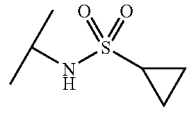 |
| (195) | 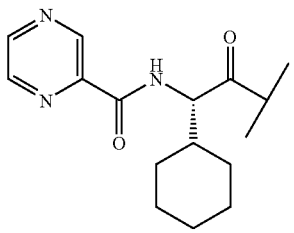 | 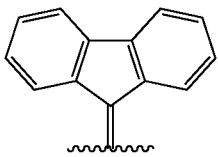 [SMILES: *=C1c2ccccc2-c2ccccc21] | 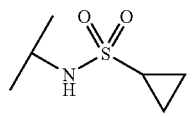 |
| (196) | 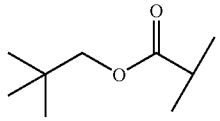 | 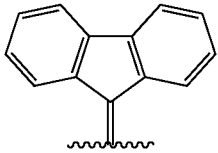 [SMILES: *=C1c2ccccc2-c2ccccc21] | 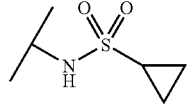 |
| (197) | 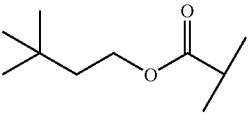 | 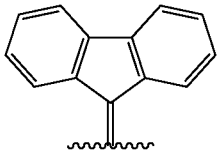 [SMILES: *=C1c2ccccc2-c2ccccc21] | 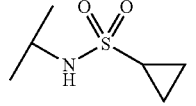 |
| (198) | 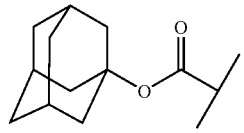 | 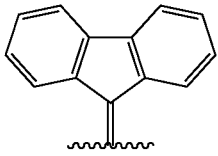 [SMILES: *=C1c2ccccc2-c2ccccc21] | 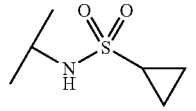 |
| (199) | 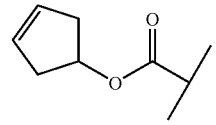 | 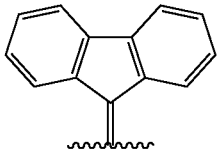 [SMILES: *=C1c2ccccc2-c2ccccc21] | 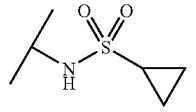 |
| (200) | 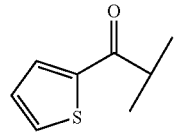 | 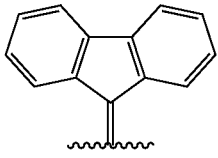 [SMILES: *=C1c2ccccc2-c2ccccc21] | 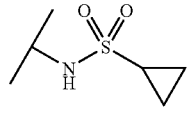 |

TABLE 3-continued

| Compound | Rx | R₁R₂ | G |
|---|---|---|---|
| (201) | 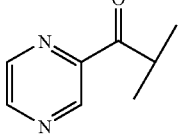 | 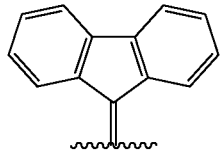 [SMILES: *=C1c2ccccc2-c2ccccc21] | 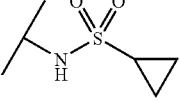 |
| (202) | 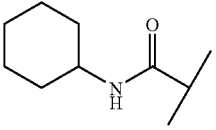 | 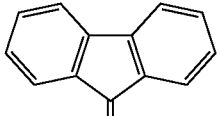 | 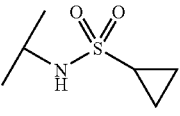 |
| (203) | 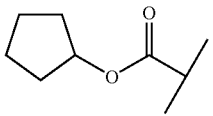 | 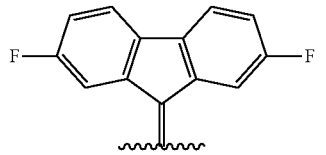 [SMILES: *=C1c2cc(F)ccc2-c2ccc(F)cc21] | 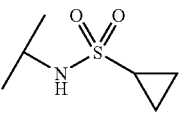 |
| (204) | 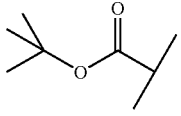 | 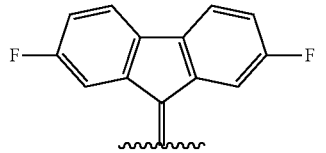 | 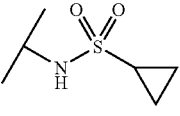 | or pharmaceutically acceptable salt thereof.

23. A pharmaceutical composition comprising a therapeutically effective amount of a compound according to claim 1 or a pharmaceutically acceptable salt thereof, in combination with a pharmaceutically acceptable carrier or excipient.

24. A method of treating a hepatitis C viral infection in a subject, comprising administering to the subject the pharmaceutical composition according to claim 23.

25. A method of inhibiting the replication of hepatitis C virus, the method comprising contacting a hepatitis C virus with an effective amount of a compound of claim 1.

26. A method of claim 24 further comprising administering an additional anti-hepatitis C virus agent.

27. The method of claim 26, wherein said additional anti-hepatitis C virus agent is selected from the group consisting of α-interferon, β-interferon, ribavarin, and adamantine.

28. The method of claim 27, wherein said additional anti-hepatitis C virus agent is an inhibitor of other targets in the hepatitis C virus life cycle which is selected from the group consisting of helicase, polymerase, metalloprotease, and IRES.

29. The compound according to claim 1 having the formula D:

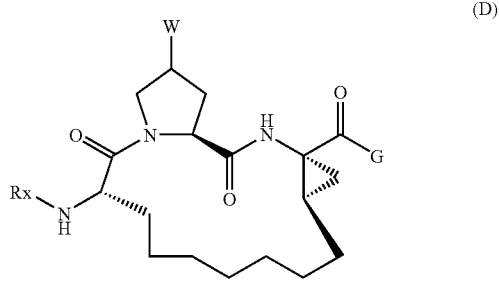

W, Rx and G are delineated for each example in TABLE 4:

TABLE 4

| Compound | Rx | W | G |
|---|---|---|---|
| (205) | tert-butyl 2-methylpropanoate group | fluoren-9-ylidene | N-H cyclopropanesulfonamide |
| (206) | cyclopentyl 2-methylpropanoate group | fluoren-9-ylidene | N-H cyclopropanesulfonamide |
| (207) | tert-butyl 2-methylpropanoate group | 2,7-difluorofluoren-9-ylidene | N-H cyclopropanesulfonamide |
| (208) | cyclopentyl 2-methylpropanoate group | 2,7-difluorofluoren-9-ylidene | N-H cyclopropanesulfonamide | or a pharmaceutically acceptable salt thereof.

* * * * *

UNITED STATES PATENT AND TRADEMARK OFFICE
CERTIFICATE OF CORRECTION

PATENT NO. : 9,526,769 B2
APPLICATION NO. : 11/759080
DATED : December 27, 2016
INVENTOR(S) : Ying Sun et al.

It is certified that error appears in the above-identified patent and that said Letters Patent is hereby corrected as shown below:

In the Claims

At Column 174
In Claim 9, Line 26, delete "ester or prodrug".

At Column 178
In Claim 18, Line 63, after alkyl, delete "-$C_1$-$C_5$" and insert -- -$C_1$-$C_8$ --.

At Columns 237 and 238

In Claim 29, Table 4, Compound (205), Column W, delete " 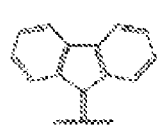 " and insert -- 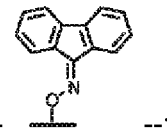 --;

In Claim 29, Table 4, Compound (206), Column W, delete " 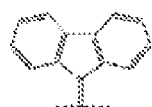 " and insert -- 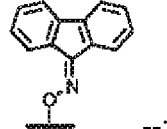 --;

in Claim 29, Table 4, Compound (207), Column W, delete " 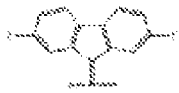 " and insert -- 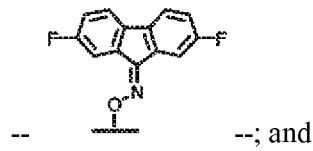 --; and Signed and Sealed this
Twenty-first Day of March, 2017

Michelle K. Lee
*Director of the United States Patent and Trademark Office*

In Claim 29, Table 4, Compound (208), Column W, delete " " and insert -- --.